US006965060B2

(12) United States Patent
Yang

(10) Patent No.: US 6,965,060 B2
(45) Date of Patent: Nov. 15, 2005

(54) PRODUCTION OF SILK-LIKE PROTEINS IN PLANTS

(75) Inventor: Jianjun Yang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 352 days.

(21) Appl. No.: 10/414,760

(22) Filed: Apr. 16, 2003

(65) Prior Publication Data

US 2003/0192077 A1 Oct. 9, 2003

Related U.S. Application Data

(62) Division of application No. 09/863,859, filed on May 23, 2001, now Pat. No. 6,608,242.
(60) Provisional application No. 60/206,968, filed on May 25, 2000.

(51) Int. Cl.[7] ................................................ A01H 9/00
(52) U.S. Cl. ...................................................... 800/295
(58) Field of Search ........................................ 800/295

(56) References Cited

U.S. PATENT DOCUMENTS

| 5,245,012 | A | 9/1993 | Lombari et al. |
| 5,728,810 | A | 3/1998 | Lewis et al. |
| 5,770,697 | A | 6/1998 | Ferrari et al. |
| 6,268,169 | B1 | 7/2001 | Fahnestock |
| 6,280,747 | B1 | 8/2001 | Philippe et al. |

FOREIGN PATENT DOCUMENTS

| EP | 0320702 A1 | 6/1989 |
| EP | 0452925 B1 | 10/1991 |
| WO | WO 9116351 A1 | 10/1991 |
| WO | WO 9411516 A1 | 5/1994 |
| WO | WO 9429450 A2 | 12/1994 |
| WO | WO 9708315 A1 | 3/1997 |
| WO | WO 9816650 A1 | 4/1998 |
| WO | WO 99/47661 A2 | 9/1999 |
| WO | WO 0194393 A2 | 12/2001 |

OTHER PUBLICATIONS

Depicker, A, Stachel, S., Dhaese P., Zambryski, P., and Goodman H. M. (1982) J. Mol. Appl. Genet. 1: 561–573.Nopaline Synthase: Transcript Mapping and DNA Sequence.
Cappello, J., Crissman, J. W., Dorman, M., Mikolajczak, M., Textor, G., Marqurt, M., Ferrari, F. (1990) Biotechnol. Prog. 6: 198–202. Genetic Engineering of Structural Protein Polymers.
Hinman, M. B., and Lewis, R. V. (1992) J. Biol. Chem. 267: 19320–19324.Isolation of a Clone Encoding a Second Dragline Silk Fibroin.
Ohshima, Y., and Suzuki, Y. (1977) Proc. Natl. Acad. Sci. USA 74:5363–5367.Cloning of the Silk Fibroin Gene and its Flanking Sequences.
Koncz, C., and Schell, J. (1986) Mol. Gen. Genet. 204: 383–396. The promoter of $T_1$–DNA gene 5 controls the tissue–specific expression of chimaeric genes carried by a novel type of Agrobacterium binary vector.
Foelix, R.F. (1992) Biology of Spiders. Cambridge, MA. Harvard University Press.Biology of Spiders.
Fahnestock, S. R., and Bedzyk, L. A. (1997) Appl. Microbiol. Biotechnol. 47: 33–39.Production of synthetic spider dragline silk protein in Pichia pastoris.
Cappello, J., Crissman, J. W. (1990) Polymer Preprints 31: 193–194. The design and production of bioactive protein polymers for biomedical applications.
Franken, E., Twuschel, U., and Hain, R. (1997) Curr. Opin. Biotechnol. 8: 411–416. Recombinant proteins from transgenic plants.
Whitelam, G. C., Cockburn, B., Gandecha, A. R., and Owen, M. R. (1993) Biotechnol. Genet. Eng. Rev. 11: 1–29. Heterologus Protein Production in Transgenic Plants.
Zhang, Z, Urry, D. W., and Daniell, H. (1996) Plant Cell Rep. (1996) 16: 174–179 Expression of an environmentally friendly synthetic protein–based polymer gene in transgenic tobacco plants.
Prince, J. T., McGrath, K. P., DiGriolamo, C. M., and Kaplan, D. L. (1995) Biochemistry 34: 10879–10885. Construction, Cloning, and Expression of Synthetic Genes Encoding Spider Dragline Silk.
Fahnestock, S.R., and Irwin, S. L. (1997) Appl. Microbiol. Biotechnol. 47: 23–32. Synthetic spider dragline silk proteins and their production in *Escherichia coli*.
Xu, M., and Lewis, R. V. (1990) Proc. Natl. Acad. Sci. USA 87: 7120–7124. Structure of a protein superfiber: Spider dragline silk.
Kaplan, D. L., Mello, C. M., Arcidiacono, S., Fossey, S., Senecal, K., and Muller, W. (1997) in Protein–Based Materials, McGrath, K. and Kaplan, D. Eds. Birkhauser, Boston pp 104–131.
Larkins, Abraham Marcus, Edt. The Biochemistry of Plants, a comprehensive Treatise. vol. 6. Protein and nucleic Acids. 1981, Academic Press. pp. 449–489.Seed Storage Proteins: Characterization and Biosynthesis.
Ausubel, F.M., Brent, R., Kingston, R. E., Moore, D. D., Seldman, J. G., Smith, J. A. and Struhl, K. Eds. (1987) Current Protocols in Molecular Biology. Greene Publishing Assoc. and Wiley–Interscience. Supplement 39 Unit 10.8.1–10.8.21.Immunoblotting and Immunodetection.

*Primary Examiner*—Karen Cochrane Carlson

(57) ABSTRACT

The invention provides methods for the production of silks and silk-like proteins (SLP's) in green plants. Expression of SLP's has been achieved in both seed and leaf tissue in green plants.

11 Claims, 22 Drawing Sheets

PRODUCTION OF SILK-LIKE PROTEINS IN PLANTS

PRIORITY DATA

This application is a divisional of Ser. No. 09/863,859, filed May 23, 2001, now U.S. Pat. No. 6,608,242, and claims priority to provisional application Ser. No. 60/206,968, filed May 25, 2000.

FIELD OF THE INVENTION

The invention relates to the field of molecular biology and plant genetics. More specifically, this invention describes a technique to produce silk-like proteins plant expression systems.

BACKGROUND OF THE INVENTION

Increasing demands for materials and fabrics that are both light-weight and flexible without compromising strength and durability has created a need for new fibers possessing higher tolerances for such properties as elasticity, denier, tensile strength and modulus. The search for a better fiber has led to the investigation of fibers produced in nature, some of which possess remarkable qualities. One of those fibers is silk, a group of externally spun fibrous protein secretions.

Silks are produced by over 30,000 species of spiders and by many other insects particularly in the order Lepidoptera (Foelix, R. F. (1992) Biology of Spiders, Cambridge, Mass. Harvard University Press). Few of these silks have been studied in detail. The cocoon silk of the domesticated silkworm Bombyx mori and the dragline silk of the orb-weaving spider Nephila clavipes are among the best characterized. Although the structural proteins from the cocoon silk and the dragline silk are quite different from each other in their primary amino acid sequences, they share remarkable similarities in many aspects. They are extremely glycine and alanine-rich proteins. Fibroin, a structural protein of the cocoon silk, contains 42.9% glycine and 30% alanine. Spidroin 1, a major component of the dragline silk, contains 37.1% glycine and 21.1% alanine. They are also highly repetitive proteins. The conserved crystalline domains in the heavy chain of the Fibroin and a stretch of polyalanine in Spidroin 1, are repeated numerous times throughout entire molecules. These crystalline domains are surrounded by larger non-repetitive amorphous domains in every 1 to 2 kilobases in the heavy chain of Fibroin, and by shorter repeated GXG amorphous domains in tandem in Spidroin 1. They are also shear sensitive due to their high copy number of the crystalline domains. During fiber spinning, the crystalline repeats are able to form anti-parallel β-pleated sheets, so that silk protein is turned into semi-crystalline fiber with amorphous flexible chains reinforced by strong and stiff crystals (Kaplan et al., (1997) in Protein-Based Materials, McGrath, K., and Kaplan, D. Eds, Birkhauser, Boston, pp 104–131).

Traditional silk production from silkworm involves growing mulberry leaves, raising silkworm, harvesting cocoons, and processing of silk fibers. It is labor intensive and time consuming and therefore prohibitively expensive. The natural defects of the silkworm silk, such as the tendency to wrinkle and the irregularity of fiber diameter further limits its application. Similarly, the mass production of the dragline silk from spiders is not plausible because only small amounts are available from each spider. Furthermore, multiple forms of spider silks are produced simultaneously by any given spider. The resulting mixture has less application than a single isolated silk because the different spider silk proteins have different properties and are not easily separated. Thus, the prospect of producing commercial quantities of spider silk from a natural source is not a practical one and there remains a need for an alternate mode of production.

By using molecular recombination techniques, one can introduce foreign genes or artificially synthesized DNA fragments into different host organisms for the purpose of expressing desired protein products in commercially useful quantities. Such methods usually involve joining appropriate fragments of DNA to a vector molecule, which is then introduced into a recipient organism by transformation. Transformants are selected using a selectable marker on the vector, or by a genetic or biochemical screen to identify the cloned fragment.

While the techniques of foreign gene expression in the host cell are well known in the art and widely practiced, the synthesis of fiber forming foreign polypeptides containing high numbers of repeating units poses unique problems. Genes encoding proteins of this type are prone to genetic instability due to the repeating sequences which result in truncated product instead of the full size protein.

In spite of the above mentioned difficulties, the expression of fiber forming proteins is known in the art. Ferrari et al. (U.S. Pat. No. 5,770,697) disclose methods and compositions for the production of polypeptides having repetitive oligomeric units such as those found in silk-like proteins (SLPs) and elastin-like proteins by the synthetic structural genes. The DNA sequences of Ferrari encode peptides containing an oligopeptide repeating units which contains at least 3 different amino acids and a total of 4–30 amino acids, there being at least 2 repeating units in the peptide and at least 2 identical amino acids in each repeating unit.

The cloning and expression of silk proteins of B. mori are also known. Ohshima et al. (Proc, Natl. Acad. Sci. USA, 74, 5363 (1977)) reported the cloning of the silk Fibroin gene complete with flanking sequences of B. mori into E. coli. Petty-Saphon et al. (EP 320702) disclose the recombinant production of silk Fibroin and silk Sericin from a variety of host including E. coli, Sacchromyces cerevisiae, Pseudomonas sp., Rhodopseudomonas sp., Bacillus sp., and Strepomyces sp.

Progress has also been made in the cloning and expression of spider silk proteins. Xu et al. (Proc, Natl. Acad. Sci. USA, 87, 7120 (1990)) report the determination of the sequence for a portion of the repetitive sequence of a dragline like protein, Spidroin 1, from the spider Nephila clavipes, based on a partial cDNA clone.

Lewis et al. (EP 452925) disclose the expression of spider silk proteins (Spidroin 1 and 2) including protein fragment and variants, of Nephila clavipes from transformed E. coli.

Lombardi et al. (U.S. Pat. No. 5,245,012) teach the production of recombinant spider silk protein comprising an amorphous domain or subunit a crystalline domain or subunit where the domain or subunit refers to a portion of the protein containing a repeating amino acid sequence that provides a particular mechanostructural property.

The recent advances in cDNA sequencing of cocoon silk and dragline silk have permitted the synthesis of artificial genes for silk-like proteins (SLPs) with sequence and structural similarity to the native proteins. These artificial genes mimicked sequence arrays of natural cocoon silk from B. mori and dragline silk from N. clavipes, and had been introduced into microorganisms such as Escherichia coli, Pichia pastoris, and Saccharomyces cerevisiae. SLPs had been produced in these microorganisms through fermentation [Cappello, J., Crissman, J. W. (1990) *Polymer Preprints* 31:193–194; Cappello et al., (1990) *Biotechnol. Prog.* 6:198–202; Fahnestock and Irwin, *Appl. Microbiol. Biotechnol.* (1997), 47(1), 23–32; Prince et al, (1995) *Biochemistry* 34:10879–10885; Fahnestock and Bedzyk, 1997, *Appl. Microbiol. Biotechnol.* (1997), 47(1), 33–39 and commonly owned WO 9429450].

Plants are becoming a favorite host for foreign gene expression. Many recombinant proteins have been produced in transgenic plants (Franken et al., *Curr. Opin. Biotechnol.* 8:411–416, (1997); Whitelam et al., *Biotechnol. Genet. Eng. Rev.* 11:1–29, (1993). Plant genetic engineering combines modern molecular recombination technology and agricultural crop production. Although a variety of silk-like and fiber forming proteins have been expressed in microbial systems, similar expression systems have not been developed in plants. Zhang et al. teach the expression of an elastin-based protein polymer in transgenic tobacco plants (Zhang et al., *Plant Cell Rep.* (1996), 16(3–4), 174–179). Although this represents the expression of a repetitive sequence in plants, the elastin polypeptide bears little resemblance to silk-like peptides and thus the feasibility of SLP expression in plants can not be predicted based on this work.

To date, there are no reported examples of recombinant silk or SLP production in plants. One possible explanation for this lies in the the striking compositional and structural differences between Silks and SLP's and native plant proteins. For example, SLP proteins are very glycine and alanine-rich, highly repetitive, and semi-crystalline in structure. These are characteristics not found in most plant proteins. Thus, introduction and expression of SLP genes in plant cells may pose a number of difficulties. For example, the repetitive sequence of SLP gene may be a target for DNA deletion and rearrangement in plant cells. Alternatively, translation of glycine and alanine-rich SLP might prematurely exhaust glycine and alanine and tRNAs pools in plant cells. Finally, accumulation of semicrystalline SLP may be recognized and degraded by the house-keeping mechanisms in the plant.

The methods recited above for the expression of silk and SLP are useful for production in microbial systems, however fail to teach the production of silk or SLP in plants. The use of a plant platform for the production of silk and silk-like proteins has several advantages over a microbial platform. For example, as a renewable resource, a plant platform requires far less energy and materiel consumption than microbial methods. Similarly, a plant platform represents a far greater available biomass for protein production than a microbial system. Finally, the fact that silks are natural proteins suggests production of high levels of silk will not be toxic to the host.

The problem to be solved, therefore is to provide a method to produce synthetic silk or SLP in commercially useful quantities at relatively low cost. Applicants have solved the stated problem by providing a method to express and produce silk or SLP using plant expression systems.

SUMMARY OF THE INVENTION

The present invention provides a method for the production of silk-like proteins in a green plant comprising:
  a) providing a, green plant containing a SLP expression cassette having the following structure:

P-SLP-T wherein:
  P is a promoter suitable for driving the expression of a silk-like protein gene;
  SLP is a transgene encoding a mature silk-like protein; and
  T is a 5' terminator;
  wherein each of P, SLP and T are operably linked such that expression of the cassette results in translation of the silk-like protein;
  b) growing said green plant under conditions whereby said transgene is expressed and the silk-like protein is produced; and
  c) optionally recovering said silk-like protein.

Additionally the invention provides plants comprising an expression cassette expressing a silk-like protein derived from the silks produced by *Bombyx mori* and *Nephila clavipes*. Specifically the silks and silk-like proteins of the present invention may be natural or variants and will have the general formula:

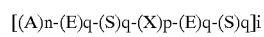

wherein:
  A or E are different non-crystalline soft segments of about 10 to 25 amino acids having at least 55% Gly;
  S is a semi-crystalline segment of about 6 to 12 amino acids having at least 33% Ala, and 50% Gly;
  X is a crystalline hard segment of about 6–12 amino acids having at least 33% Ala, and 50% Gly; and
wherein,
  n=2, 4, 8, 16, 32, 64, or 128;
  q=0, 1, 2, 4, 8, 16, 32, 64, or 128;
  p=2, 4, 8,16, 32, 64, or 128;
  i=1–128; and
where $p \geq n$ or q.

BRIEF DESCRIPTION OF THE DRAWINGS

Sequence Descriptions and Deposits

Figure 1:
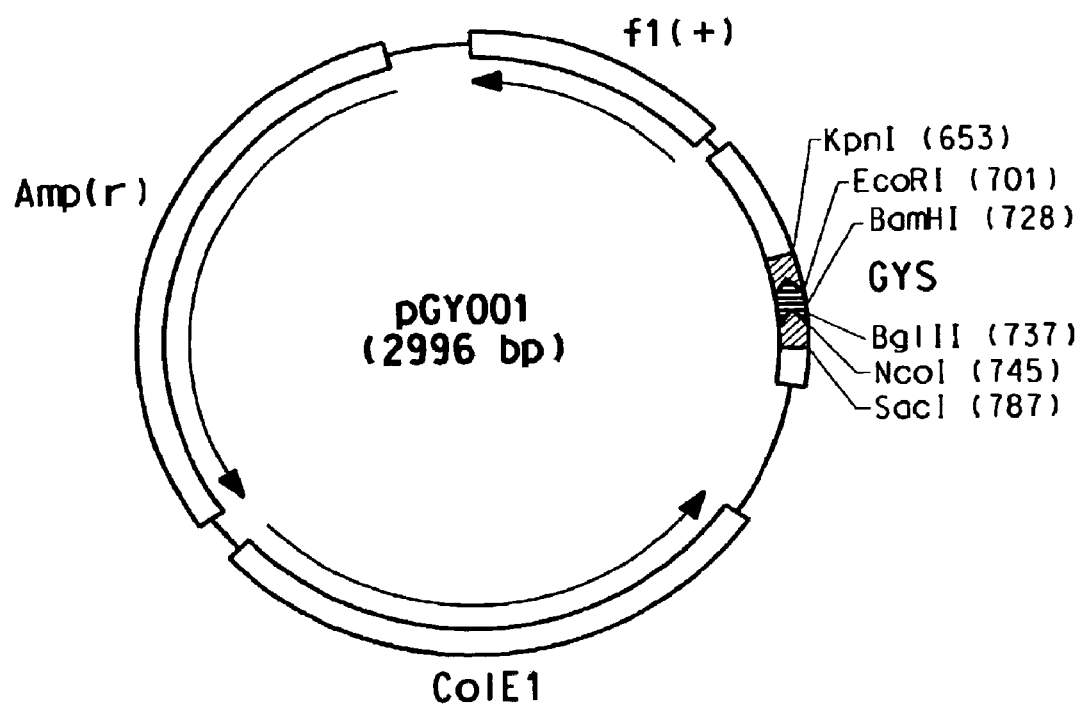
FIG. 1 is a plasmid map of pGY001 carrying the GYS adapter.

The terms "peptide", "polypeptide" and "protein" are used interchangeably.

The term "spider silk variant protein" will refer to a designed protein, the amino acid sequence of which is based on repetitive sequence motifs and variations thereof that are found in a known a natural spider silk.

The term "DP-1B" will refer to any spider silk variant derived from the amino acid sequence of the natural Protein 1 (Spidroin 1) of *Nephila calvipes* as set forth in SEQ ID NO:1.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene or "transgene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"Regulated promoter" refers to promoters that direct gene expression not constitutively but in a temporally- and/or spatially-regulated manner and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered; numerous examples may be found in the compilation by Okamuro et al., *Biochemistry of Plants* 15:1–82, 1989. Since in most cases the exact boundaries of regulatory sequences have not been completely defined, DNA fragments of different lengths may have identical promoter activity.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

The term "complementary" is used to describe the relationship between nucleotide bases that are capable to hybridizing to one another. For example, with respect to DNA, adenosine is complementary to thymine and cytosine is complementary to guanine.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific) vector containing a foreign gene and having elements in addition to the foreign gene that allow for enhanced expression of that gene in a foreign host.

As used herein the following abbreviations will be used to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

Expression Cassette

The present invention provides a method for the production of silk-like proteins in plants. The method proceeds by providing a plant expression cassette having a DNA construct comprising a promoter, a transgene encoding a silk-like protein and a 5' terminator region. Expression of the transgene may be constitutive or regulated.

Promoters useful for driving the expression of foreign genes in plant hosts are common and well known in the art. It may be useful to have the present SLP transgene expressed constitutively or in a regulated fashion. Constitutive plant promoters are well known. Some suitable promoters include but are not limited to the nopaline synthase promoter, the octopine synthase promoter, CaMV 35S promoter, the ribulose-1,5-bisphosphate carboxylase promoter, Adh1-based pEmu, Act1, the SAM synthase promoter and Ubi promoters and the promoter of the chlorophyll a/b binding protein.

Alternatively it may be desired to have the SLP transgene expressed in a regulated fashion. Regulated expression of the SLP's is possible by placing the coding sequence of the silk-like protein under the control of promoters that are tissue-specific, developmental-specific, or inducible.

Several tissue-specific regulated genes and/or promoters have been reported in plants. These include genes encoding the seed storage proteins (such as napin, cruciferin, .beta.-conglycinin, glycinin and phaseolin), zein or oil body proteins (such as oleosin), or genes involved in fatty acid biosynthesis (including acyl carrier protein, stearoyl-ACP desaturase, and fatty acid desaturases (fad 2- 1)), and other genes expressed during embryo development (such as Bce4, see, for example, EP 255378 and Kridl et al., *Seed Science Research* (1991) 1:209–219). Particularly useful for seed-specific expression is the pea vicilin promoter [Czako et al., *Mol. Gen. Genet.* (1992), 235(1), 33–40]. Other useful promoters for expression in mature leaves are those that are switched on at the onset of senescence, such as the SAG promoter from *Arabidopsis* [Gan et al., Inhibition of leaf senescence by autoregulated production of cytokinin, *Science* (Washington, D.C.) (1995), 270 (5244), 1986–8].

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated [John et al., Gene expression in cotton (*Gossypium hirsutum L.*) fiber: cloning of the mRNAs, *Proc. Natl. Acad. Sci. U.S.A.* (1992), 89 (13), 5769–73]. cDNA clones from tomato displaying differential expression during fruit development have been isolated and characterized [Mansson et al., *Mol. Gen. Genet.* (1985) 200:356–361; Slater et al., *Plant Mol. Biol.* (1985) 5:137–147]. The promoter for polygalacturonase gene is active in fruit ripening. The polygalacturonase gene is described in U.S. Pat. No. 4,535,060 (issued Aug. 13, 1985), U.S. Pat. No. 4,769, 061 (issued Sep. 6, 1988), U.S. Pat. No. 4,801,590 (issued Jan. 31, 1989) and U.S. Pat. No. 5,107,065 (issued Apr. 21, 1992), which disclosures are incorporated herein by reference.

Mature plastid mRNA for psbA (one of the components of photosystem II) reaches its highest level late in fruit development, in contrast to plastid MRNAs for other components of photosystem I and II which decline to nondetectable levels in chromoplasts after the onset of ripening [Piechulla et al., *Plant Mol. Biol.* (1986) 7:367–376]. Recently, cDNA clones representing genes apparently involved in tomato pollen [McCormick et al., *Tomato Bio-* technology (1987) Alan R. Liss, Inc., New York) and pistil (Gasser et al., *Plant Cell* (1989), 1:15–24] interactions have also been isolated and characterized.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 [John et al., Gene expression in cotton (*Gossypium hirsutum L.*) fiber: cloning of the mRNAs, *Proc. Natl. Acad. Sci. U.S.A.* (1992), 89(13), 5769–73]). The E6 gene is most active in fiber, although low levels of transcripts are found in leaf, ovule and flower.

The termination region used in the expression cassette will be chosen primarily for convenience, since the termination regions appear to be relatively interchangeable. The termination region which is used may be native with the transcriptional initiation region, may be native with the DNA sequence of interest, or may be derived from another source. The termination region may be naturally occurring, or wholly or partially synthetic. Convenient termination regions are available from the Ti-plasmid of *A. tumefaciens*, such as the octopine synthase and nopaline synthase termination regions or from the genes for β-phaseolin, the chemically inducible lant gene, pIN (Hershey et al., Isolation and characterization of cDNA clones for RNA species induced by substituted benzenesulfonamides in corn. *Plant Mol. Biol.* (1991), 17(4), 679–90; U.S. Pat. No. 5,364,780).

The transgene encoding the silk or SLP protein may be naturally occurring or may be synthetic. The present transgenes will generally be derived from silk producing organisms such as insects in the order *Lepidoptera* including *Bombyx mori* and *Nephila clavipes*. Genes encoding the subject polypeptides will generally be at least about 900 nucleotides in length, usually at least 1200 nucleotides in length, preferably at least 1500 nucleotides in length. The genes of the subject invention generally comprise concatenated monomers of DNA encoding the same amino acid sequence, where only one repeating unit is present to form a homopolymer, where all or a part of two or more different monomers encoding different amino acid repeating units may be joined together to form a new monomer encoding a block or random copolymer. The individual amino acid repeating units will have from 3 to 20 amino acids (9 to 60 nucleotides), generally 3 to 15 amino acids (9 to 45 nucleotides), usually 3 to 12 amino acids (9 to 36 nucleotides), more usually 3 to 9 amino acids (9 to 27 nucleotides) amino acids, usually having the same amino acid appear at least twice in the same unit, generally separated by at least one amino acid. In some instances, the minimum number of amino acids will be 4. Within a monomer, dsDNA encoding the same amino acid repeating unit may involve two or more nucleotide sequences, relying on the codon redundancy to achieve the same amino acid sequence.

The genes of the subject invention comprise regions comprising repeats of the repetitive units, usually a block of at least 2 units, and up to the entire region of repetitive units. Blocks of repetitive units maybe interspersed with individual or blocks of other repetitive units, or intervening sequences. The repeating units may have the same sequence or there may be 2 or more different sequences employed to encode the repeating unit, using the codon redundancy for a particular amino acid to vary the sequence.

A silk-like-protein (SLP) gene may be produced by providing oligomers or multimers of from about 5 to 25 repeat units as described above, more usually of about 6 to 15 repeat units. By having different cohesive ends, the oligomers may be concatemerized to provide for the polymer having 2 or more of the oligomeric units, usually not more than about 50 oligomeric units, more usually not more than about 30 oligomeric units, and frequently not more than about 25 oligomeric units.

Silk and SLP Polypeptides

The present invention provides various silk and silk-like proteins for expression from a plant platform. Of particular interest are polypeptides which have as a repeating unit SGAGAG (SEQ ID NO:2) and GAGAGS (SEQ ID NO:3). This repeating unit is found in a naturally occurring silk fibroin protein, which can be represented as GAGAG (SGAGAG)$_8$ SGAAGY (SEQ ID NO:4). Particularly suitable in the present invention are silk-like protein having the general formula:

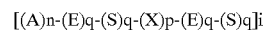

wherein:

A or E are different non-crystalline soft segments of about 10 to 25 amino acids having at least 55% Gly;

S is a semi-crystalline segment of about 6 to 12 amino acids having at least 33% Ala, and 50% Gly;

X is a crystalline hard segment of about 6–12 amino acids having at least 33% Ala, and 50% Gly; and wherein, n=2, 4, 8, 16, 32, 64, 128;

q=0, 1, 2, 4, 8, 16, 32, 64, 128;

p=2, 4, 8, 16, 32, 64, 128;

i=1–128; and where p≧n or q.

Preferred combinations of the non-crystalline, semi-crystalline or hard segments will include, but are not limited to [(A)$_4$-(X)$_8$]$_8$, [(A)$_4$-(X)$_8$-(S)]$_8$, [(A)$_4$-(X)$_8$-(E)]$_8$, [(A)$_8$-(X)$_8$]$_8$, [(A)$_4$-(S)-(X)$_8$]$_8$, [(A)$_4$-(S)$_2$-(X)$_8$]$_8$, [(A)$_4$-(E)-(X)$_8$-(E)]$_8$, [(A)$_4$-(E)-(X)$_8$]$_8$, [(A)$_4$-(S)-(X)$_8$-(E)]$_8$, and [(A)$_4$-(S)$_2$-(X)$_8$-(E)]$_8$. Most preferred combinations are these in which the non-crystalline, semi-crystalline or hard segments are defined as follows: A=SGGAGGAGG (SEQ ID NO:5), E=GPGQQGPGGY (SEQ ID NO:6), S=GAGAGY (SEQ ID NO:7), and X=SGAGAG (SEQ ID NO:2).

In a preferred embodiment the silk or SLP may be derived form spider silk. There are a variety of spider silks which may be suitable for expression in plants. Many of these are derived from the orb-weaving spiders such as those belonging to the genus *Nephila*. Silks from these spiders may be divided into major ampullate, minor ampullate, and flagelliform silks, each having different physical properties. For a review of suitable spider silks see Hayashi et al., *Int. J. Biol. Macromol.* (1999), 24(2,3), 271–275, for example. Those of the major ampullate are the most completely characterized and are often refereed to as spider dragline silk. Natural spider dragline consists of two different proteins that are co-spun from the spider's major ampullate gland. The amino acid sequence of both dragline proteins has been disclosed by Xu et al., *Proc. Natl, Acad. Sci. U.S.A.,* 87, 7120, (1990) and Hinman and Lewis, *J. Biol. Chem.* 267, 19320 (1992), and will be identified hereinafter as Dragline Protein 1 (DP-1) and Dragline Protein 2 (DP-2). Within the context of the present invention Dragline Protein 1 (DP-1) and Dragline Protein 2 (DP-2) were the focus for spider silk variant design.

The design of the spider silk variant proteins was based on consensus amino acid sequences derived from the fiber forming regions of the natural spider silk dragline proteins of *Nephila clavipes*. The amino acid sequence of a fragment of DP-1 is repetitive and rich in glycine and alanine, but is otherwise unlike any previously known amino acid sequence. The "consensus" sequence of a single repeat, viewed in this way, is:

A GQG GYG GLG XQG A GRG GLG GQG A GAAAAAAGG
(SEQ ID NO:8)

where X may be S,G, or N.

Individual repeats differ from the consensus according to a pattern which can be generalized as follows: (1) The poly-alanine sequence varies in length from zero to seven residues. (2) When the entire poly-alanine sequence is deleted, so also is the surrounding sequence encompassing AGRGGLGGQGAGA$_n$GG (SEQ ID NO:9). (3) Aside from the poly-alanine sequence, deletions generally encompass integral multiples of three consecutive residues. (4) Deletion of GYG is generally accompanied by deletion of GRG in the same repeat. (5) A repeat in which the entire poly-alanine sequence is deleted is generally preceded by a repeat containing six alanine residues.

Synthetic analogs of DP-1 were designed to mimic both the repeating consensus sequence of the natural protein and the pattern of variation among individual repeats. Two analogs of DP-1 were designed and designated DP-1A and DP-1B. DP-1A is composed of a tandemly repeated 101-amino acid sequence listed in SEQ ID NO10. The 101-amino acid "monomer" comprises four repeats which differ according to the pattern (1)–(5) above. This 101-amino acid long peptide monomer is repeated from 1 to 16 times in a series of analog proteins. DP-1B was designed by reordering the four repeats within the monomer of DP-1A. This monomer sequence, shown in SEQ ID NO:11, exhibits all of the regularities of (1)–(5) above. In addition, it exhibits a regularity of the natural sequence which is not shared by DP-1A, namely that a repeat in which both GYG and GRG are deleted is generally preceded by a repeat lacking the entire poly-alanine sequence, with one intervening repeat. The sequence of DP-1B matches the natural sequence more closely over a more extended segment than does DP-1A.

Thus it is an object of the present invention to provide a spider dragline variant protein wherein the full length variant protein is defined by the formula:

[ACGQGGYGGLGXQGAGRGGLGGQGAGAnGG]$_z$ (SEQ ID NO:12)

wherein X=S, G or N; n=0–7 and z=1–75, and wherein the value of z determines the number of repeats in the variant protein and wherein the formula encompasses variations selected from the group consisting of:

(a) when n=0 the sequence encompassing AGRGGLG-GQGAGAnGG (SEQ ID NO:9) is deleted;

(b) deletions other than the poly-alanine sequence, limited by the value of n will encompass integral multiples of three consecutive residues;

(c) the deletion of GYG in any repeat is accompanied by deletion of GRG in the same repeat; and (d) where a first repeat where n=0 is deleted, the first repeat is preceded by a second repeat where n=6; and wherein the full-length protein is encoded by a gene or genes and wherein said gene or genes are not endogenous to the *Nephila clavipes* genome.

The silk variants and SLP's of the present invention will have physical properties commonly associated with natural proteins. So for example, the silks and SLP's will be expected to have tenacities (g/denier) of about 2.8 to about 5.2, tensile strengths (psi) of about 45,000 to about 83,000 and elongations (%) of about 13 to about 31.

Plant Hosts

Virtually any plant capable of supporting the expression of a silk or SLP gene is suitable as a host in the present invention. Suitable plants will be either monocots or dicots and will preferably be of the sort that are hardy and permit several harvests per year. Suitable green plants will included but are not limited to soybean, rapeseed, sunflower, cotton, corn, tobacco, alfalfa, wheat, barley, oats, sorghum, rice, *Arabidopsis,* sugar beet, sugar cane, canola, millet, beans, peas, rye, flax, grasses, and banana.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. [See for example, EP 295959 and EP 138341]. It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice [Pacciotti et al. (1985) *Bio/Technology* 3:241; Byrne et al. (1987) *Plant Cell, Tissue and Organ Culture* 8:3; Sukhapinda et al. (1987) *Plant Mol. Biol.* 8:209–216; Lorz et al. (1985) *Mol. Gen. Genet.* 199:178; Potrykus (1985) *Mol. Gen. Genet.* 199:183; Park et al., *J. Plant Biol.* (1995), 38(4), 365–71; Hiei et al., *Plant J.* (1994), 6:271–282]. The use of T-DNA to transform plant cells has received extensive study and is amply described [EP 120516; Hoekema, In: *The Binary Plant Vector System,* Offset-drukkerij Kanters B. V.; Alblasserdam (1985), Chapter V, Knauf, et al., *Genetic Analysis of Host Range Expression by Agrobacterium* In: *Molecular Genetics of the Bacteria-Plant Interaction,* Puhler, A. ed., Springer-Verlag, N.Y., 1983, p. 245; and An, et al., *EMBO J.* (1985) 4:277–284]. For introduction into plants, the chimeric genes of the invention can be inserted into binary vectors as described in the examples.

Other transformation methods are available to those skilled in the art, such as direct uptake of foreign DNA constructs [see EP 295959], techniques of electroporation [see Fromm et al. (1986) *Nature* (London) 319:791] or high-velocity ballistic bombardment with metal particles coated with the nucleic acid constructs [see Kline et al. (1987) *Nature* (London) 327:70, and see U.S. Pat. No. 4,945,050]. Once transformed, the cells can be regenerated by those skilled in the art. Of particular relevance are the recently described methods to transform foreign genes into commercially important crops, such as rapeseed [see De Block et al. (1989) *Plant Physiol.* 91:694–701], sunflower [Everett et al. (1987) *Bio/Technology* 5:1201], soybean [McCabe et al. (1988) *Bio/Technology* 6:923; Hinchee et al. (1988) *Bio/Technology* 6:915; Chee et al. (1989) *Plant Physiol.* 91:1212–1218; Christou et al. (1989) *Proc. Natl. Acad. Sci USA* 86:7500–7504; EP 301749], rice [Hiei et al., *Plant J.* (1994), 6:271–282], and corn [Gordon-Kamm et al. (1990) *Plant Cell* 2:603–618; Fromm et al. (1990) *Biotechnology* 8:833–839].

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a polymerase chain reaction (PCR) amplication or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Recovery Methods

The SLP's of the present invention may be extracted and purified from the plant tissue by a variety of methods. Preferred in the present invention is a method involving removal of native plant proteins from homogenized plant tissue by lowering pH and heating, followed by ammonium sulfate fractionation. Briefly, total soluble proteins are extracted from the transgenic plants by homogenizing plant tissues such as seeds and leaves. Native plant proteins are removed by precipitation at pH 4.7 and then at 60° C. The resulting supernatant is then fractionated with ammonium sulfate at 40% saturation. The resulting protein will be on the order of 95% pure. Additional purification may be achieved with conventional gel or affinity chromatography.

DESCRIPTION OF THE PREFERRED EMBODIMENTS

In this invention, plants are utilized as a production platform for the production of SLPs. Dragline silk-based SLPs are of particular interest because (1) the structural features of dragline silk represent those of SLPs in general so that its expression should reflect the fate of other similar SLP genes in plants, and (2) the fibers of dragline silk possesses many excellent properties which fit well with criteria of the next generation of fibers.

The present invention was demonstrated in two plant systems, Arabidopsis and soy embryo tissue culture. Genes encoding either 8mer or 16mers of a DP-1B spider dragline variant were engineered into an expression cassette under the control of either a 35S constitutive promoter or a β-Conglycine seed specific promoter and having a NOS terminator region. The cassette was transformed into Agrobacterium, which was then used to infect Arabidopsis. The presence of both the 8mer and 18mer spider silk was confirmed immunologically. Protein determination indicated average expression levels at 0.34% of total soluble protein (approximately 0.07% of dry weight) for the 8mer in leaf tissue and at 0.03% of total soluble protein (approximately 0.006% of dry weight) for the 16mer in leaf tissue. Similarly the 8mer was expressed at an average levels of 1.2% of total protein (approximately 0.24% of dry weight) in seeds and the 16mer was expressed at an average level of 0.78% of total protein (approximately 0.16% of dry weight) in seeds.

The same 8mer and 16mer constructs were used for the transformation of soy embryo tissue culture. SLP expression in soybean is extremely attractive since soybean is one of the major crops globally and it itself is a higher efficient and low cost protein synthesis machine. Because gene expression in soy somatic embryos is equivalent to in soybean seeds, the expression of the SLP genes in the embryos demonstrated the feasibility that SLP can be produced in the transgenic soybean seeds. Transformation was effected by ballistic bombardment. Average expression level of 8-mer SLP in the soy embryo system was 1.0% of total soluble protein (approximately 0.4% of dry weight).

Industrial-scale SLP production from transgenic plants requires a purification scheme mostly based on simple methods such as precipitation, filtration, and centrifugation. Due to their special structure and amino acid composition, DP-1B proteins are very stable in water solution; thus they may be possible to be purified from other plant proteins by utilizing simple methods discussed above. Toward this goal, a pGY401 transgenic *Arabidopsis* plant expressing higher level of DP-1B.8P protein was used in developing the purification scheme. To obtain a large amount of starting material, homozygous transgenic plant was selected for direct soil growth. T4 homozygous seeds were germinated and grown. The plants were harvested and total protein was fractionated. Each fraction was checked for the presence of DP-1B protein. The majority of DP-1B protein was found to be in $(NH_4)_2SO_4$ precipitation fraction. This simple method can remove approximately 95% of plant proteins while concentrating DP-1B protein.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual:* Cold Spring Harbor Laboratory Press: Cold Spring Harbor, (1989) (Maniatis) and by T. J. Silhavy, M. L. Bennan, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology,* Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Materials and methods suitable for the transformation and growth of plants are well known in the art. Techniques suitable for use in the following examples may be found as set out in *Plant Molecular Biology, A Laboratory Manual* (Melody S. Clark, eds., Springer-Verlag, Berlin, Heidelberg, 1997), *Methods in Plant Molecular Biology, A Laboratory Course Manual* (Pal Maliga, Daniel F. Flessing, Anthony R. Cashmore, Wilhelm Cruissem, Joseph E. Varner, eds., Cold Spring Harbor Laboratory Press, 1995), and *Methods in Molecular Biology, Volume* 82, *Arabidopsis Protocols* (Jose M. Martinez-Zapater, Julio Salinas, eds., Humana Press, Totowa, N.J. 1998). All reagents, restriction enzymes and materials used for the growth and maintenance of transgenic plants were obtained from Aldrich Chemicals (Milwaukee, Wis), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Example 1

Construction of Plasmids Containing Synthetic Genes for Analogs of *Nephila clavipes* Spidroin 1 for Expression in Arabidopsis Synthetic genes of 8-mer and 16-mer DP-1B.33 were obtained from the DuPont Company (Wilmington, Del. 19898) (WO 9429450). These genes encode for 809 (SEQ ID NO:13) and 1617 (SEQ ID NO:14) amino acid protein sequences, respectively, that represent essential structural element and repetitive pattern in *Nephila clavipes* Spidroin 1. Plasmid pFP717 and pFP723 (fully described in WO 9429450), which carry those synthetic genes, were obtained for these experiments.

To add a start codon at the N-terminus, and a 6-histidine coding sequence followed by a stop codon at C-terminus of the synthetic genes, adapter GYS was made. Oligonucleotide sequences GYS[+] (5' GAT CTC CAT GGC TAG ATC TAG AGG ATC CCA TCA CCA TCA CCA TCA CTA AG 3') (SEQ ID NO: 15) and GYS[−] (5' AAT TCT TAG TGA TGG TGA TGG TGA TGG GAT CCT CTA GAT CTA GCC ATG GA 3')(SEQ ID NO:16) were synthesized by standard methods. The oligonucleotides were diluted to 1 μg/μL with TE (10 m tris, 1 m EDTA, pH 8.0) and mixed into a tube in equal volumes. The mixture was boiled for 5 min and then slowly cooled to room temperature. Adapter GYS formed in this process is shown below. The adapter has sticky ends complementary to BamHI and EcoRI digestion sites, respectively, and encodes for a small peptide including a start codon, ARSRGS (SEQ ID NO:17) 6-istidine tag, and a stop codon. It also introduces a few restriction sites such as NcoI, Bagll, XbaI, and BamHI. The adapter was cloned into pBluescript-SK(+) (Stratagene, La Jolla, Calif.) between restriction sites BamH1 and EcoR1 by T4 ligase (Life Technologies, Gaithersburg, Md.). The resultant plasmid, called pGY001 (FIG. 1) was amplified in XL1-Blue *E. coli* cells (Stratagene, La Jolla, Calif.) and prepared using QIAprep Spin Miniprep Kit (Qiagen, Valencia, Calif.). The sequence of the adapter was confirmed by standard sequencing.

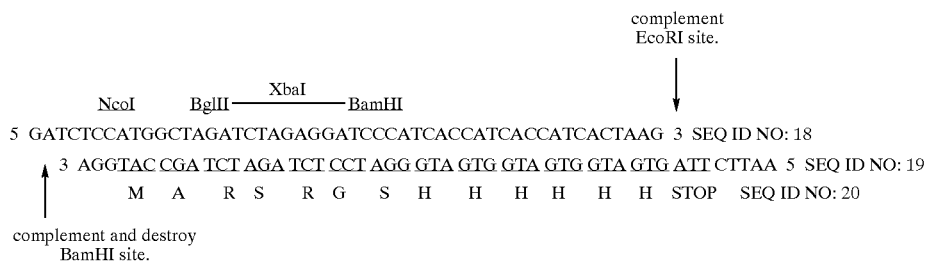

complement EcoRI site.

NcoI BglII XbaI BamHI

5 GATCTCCATGGCTAGATCTAGAGGATCCCATCACCATCACCATCACTAAG 3 SEQ ID NO: 18

3 AGGTAC CGA TCT AGA TCT CCT AGG GTA GTG GTA GTG GTA GTG ATT CTTAA 5 SEQ ID NO: 19

M A R S R G S H H H H H H STOP SEQ ID NO: 20 complement and destroy BamHI site.

Figure 2A:
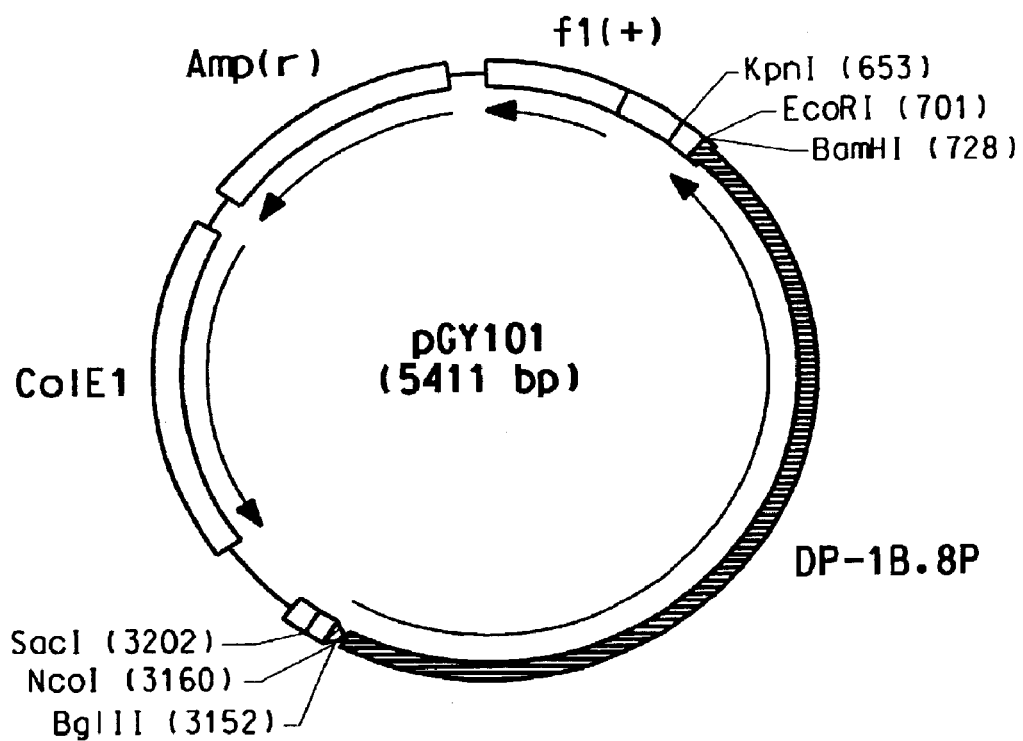
FIG. 2A is a plasmid map of pGY101 carrying the DP-1B.8P gene.
Figure 2B:
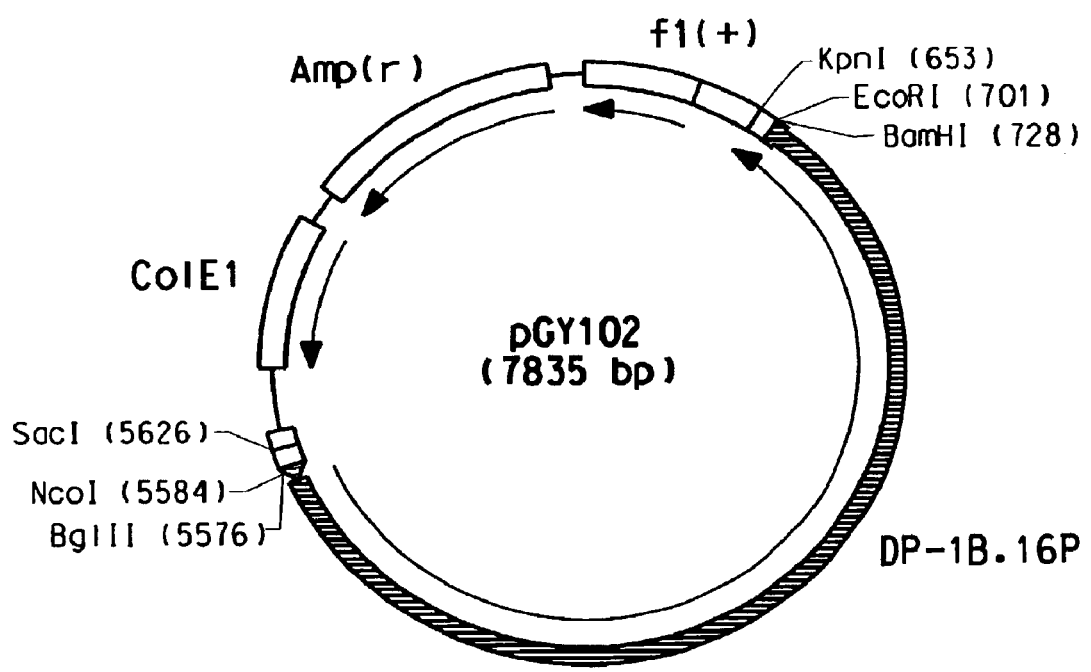
FIG. 2B is a plasmid map of pGY102 carrying the DP-1B.16P gene.

Two μg of Plasmid Pfp717 and Pfp723 were subjected to 37° C. restriction digestion of BglII and BamHI for 2 hrs. 8-mer and 16-mer DP-1B.33 genes were separated on a 0.8% agarose gel and purified using QIAquick Gel Extract Kit (Qiagen, Valencia, Calif.). Two μg of pGY001 was also digested in a 50 μL reaction by the same enzymes. To make dephosphorylated pGY001, 10 μL of dephosphorylation buffer and 2 μL of CIAP (Life Technologies, Gaithersburg, Md.) were added to the reaction and filled with water to a final volume of 100 μL. The reaction mixture was placed at 37° C. for 30 min and additional 2 μL of CIAP was added for another 30 min incubation. The DNA was cleaned up by using QIAquick PCR Purification Kit (Qiagen, Valencia, Calif.). 8-mer and 16-mer DP-1B.33 from pFP717 and pFP723 were then cloned into pGY001 between BglII and BamHI sites using T4 ligase, resulting in pGY101 and pGY102, respectively (FIGS. 2A and 2B). Plasmids (pGY101, pGY102) were amplified in XL1-Blue *E. coli* and purified using QIAprep Spin Miniprep Kit. These two plasmids, contain the coding regions for the 8-mer (in pGY101) and 16-mer (in pGY102) DP-1B.33 with a N-terminal start codon and a C-terminal 6-histidine coding sequence and a subsequent stop codon added. Thus the plasmids contained two complete synthetic genes, DP-1B 8-mer for plants (SEQ ID NO:21) encoding an 818 amino acid residue polypeptide (SEQ ID NO:22) and DP-1B 16-mer for plants (SEQ ID NO:23) encoding a 1626 amino acid residue polypeptide (SEQ ID NO:24). Accuracy of the insertions was confirmed by DNA sequencing.

Example 2

Construction of Expression Cassettes

To build cassettes with appropriate 5' promoters and 3' terminators (polyadenylation sequences) for constitutive and seed-specific expression of DP-1B genes, plasmids pML63 and pCW 109 were provided by DuPont Agricultural Products (Wilmington, Del., 19898). pCW109 is fully described in U.S. Pat. No. 5,955,650 and WO 94/11516. Vector pML63 contains the uidA gene (which encodes the GUS enzyme) operably linked to the CaMV35S promoter and 3' NOS sequence. pML63 is modified from pMH40 to produce a minimal 3' NOS terminator fragment. pMH 40 is described in WO 98/16650, the disclosure of which is hereby incorporated by reference. Using standard techniques familiar to those skilled in the art, the 770 base pair terminator sequence contained in pMH40 was replaced with a new 3' NOS terminator sequence comprising nucleotides 1277 to 1556 of the sequence published by Depicker et al. (1982, *J. Appl. Genet.* 1:561–574).

Figure 3A:
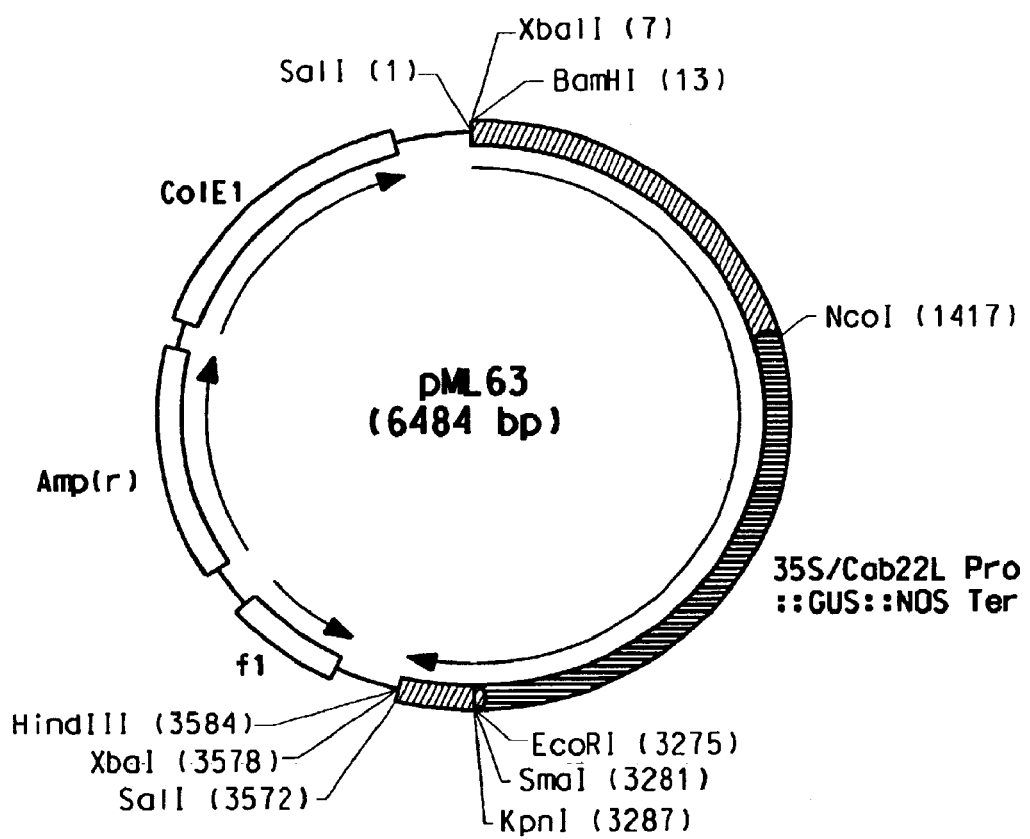
FIG. 3A is a plasmid map of pML63 carrying a 35S/Cab221 promoter driving a GUS reporter.
Figure 4A:
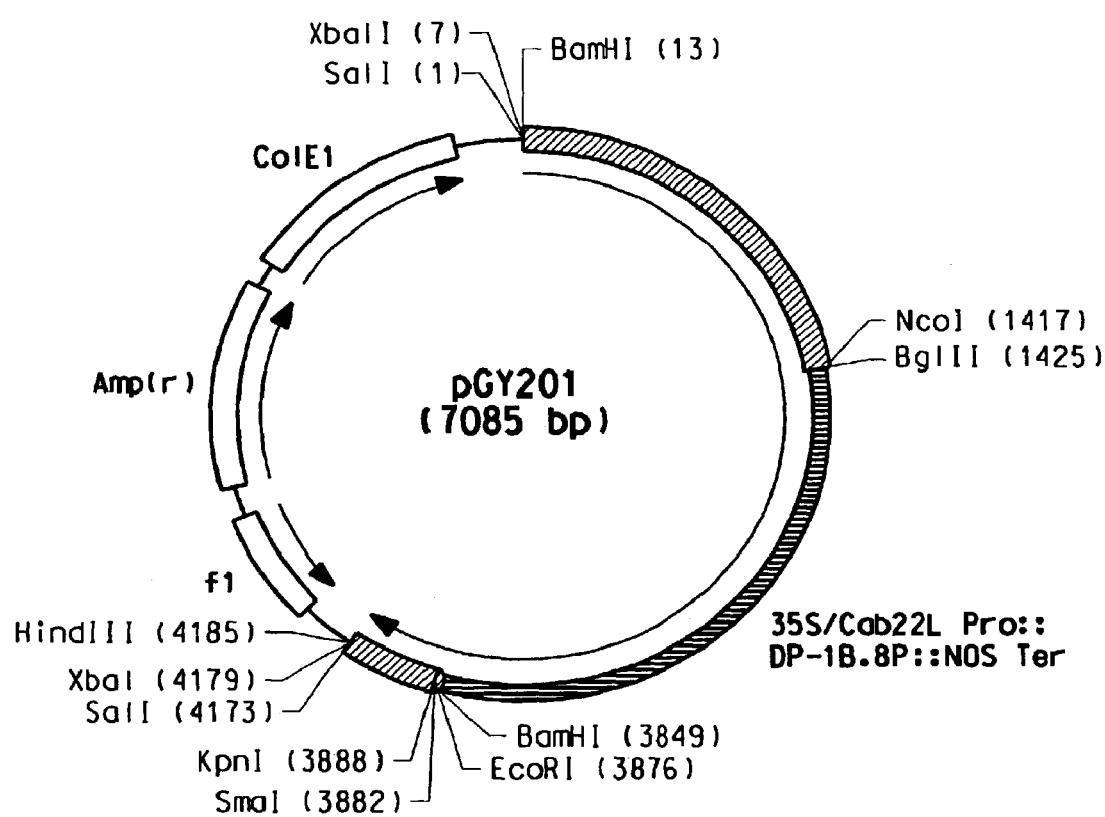
FIG. 4A is a plasmid map of pGY201 carrying the DP-1B.8P gene under the control of the 35S/Cab221 promoter.
Figure 4B:
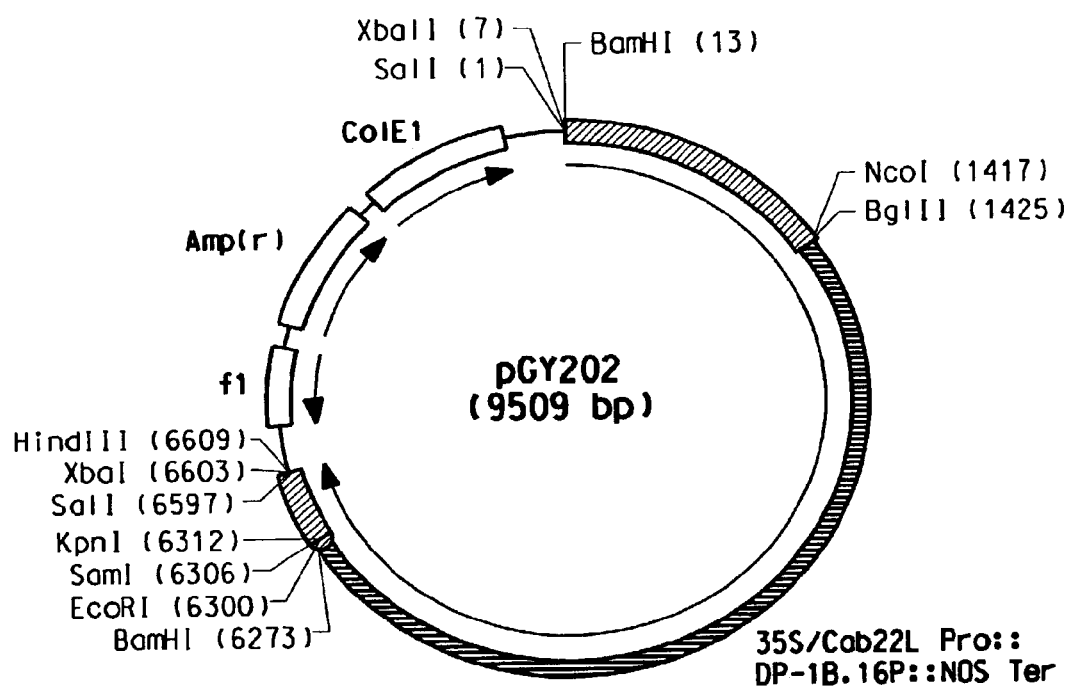
FIG. 4B is a plasmid map of pGY202 carrying the DP-1B.16P gene under the control of the 35S/Cab221 promoter.

As shown in FIG. 3A, pML63 includes a GUS expression cassette with a 5' CaMV 35S/Cab22L promoter and a 3' NOS terminator (35S/Cab22L Pro::GUS::NOS Ter). To replace GUS with DP-1B.8P, pML63 and pGY101 were digested by restriction the enzymes NcoI and EcoRI. The DNA fragment containing DP-1B.8P from pGY101 was cloned into pML63 by the method described earlier. The resultant plasmid was named pGY201 and contained an expression cassette of 35S/Cab22L Pro::DP-1B.8P::NOS Ter. The DP-1B.16P was also substituted for GUS in pML63, in which pGY 102 was used instead of pGY101. The plasmid containing an expression cassette of 35S/Cab22L Pro::DP-1B.16P::NOS Ter was designated as pGY202. The detailed structures of both pGY201 and pGY202 are shown in FIGS. 4A and 4B.

Figure 3B:
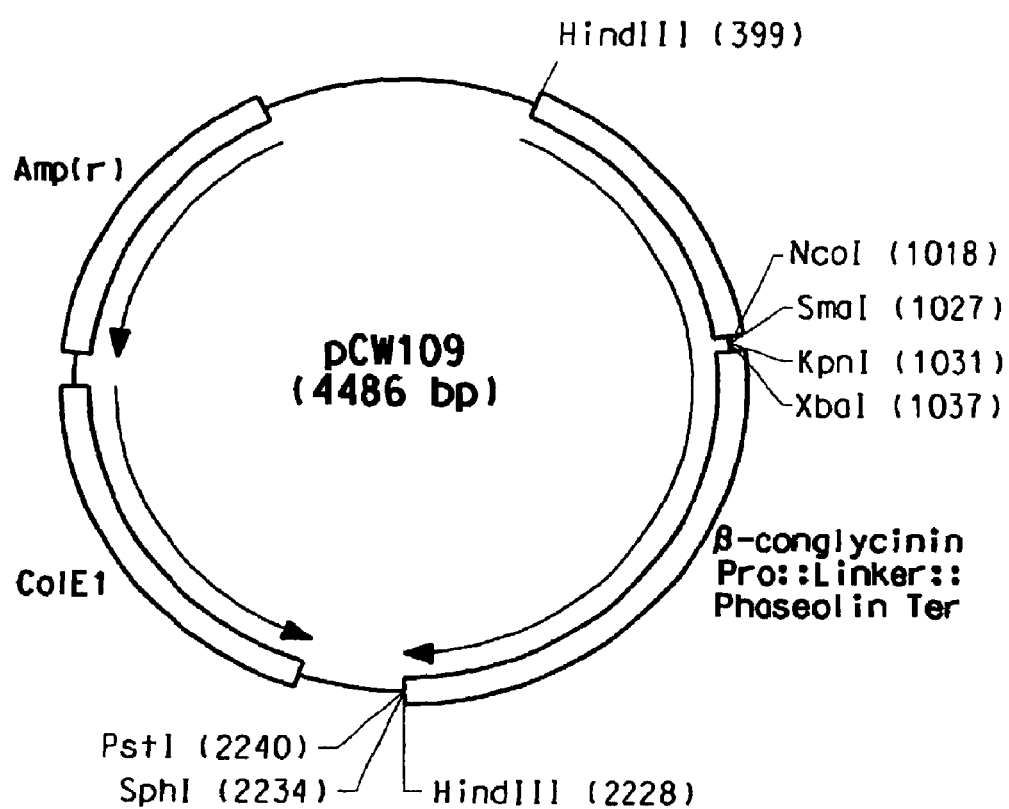
FIG. 3B is a plasmid map of pCW109 carrying the β-conglycinin promoter.
Figure 5A:
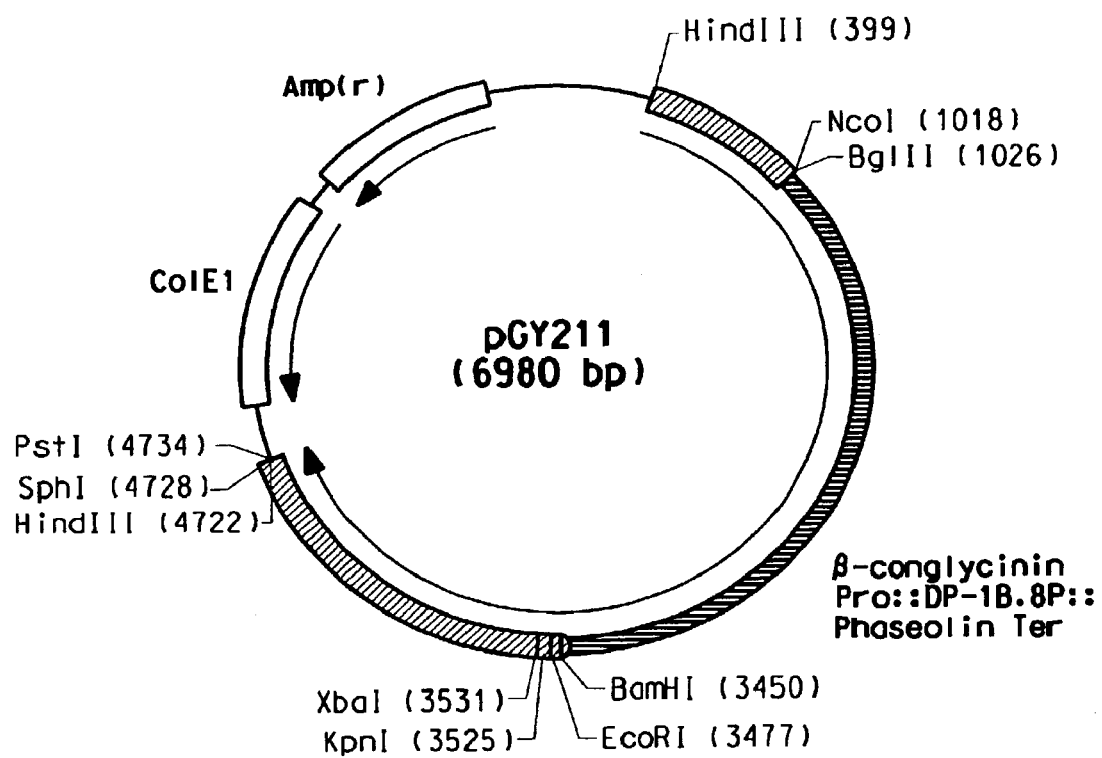
FIG. 5A is a plasmid map of pGY211 carrying the DP-1B.8P under the control of the β-conglycinin promoter.
Figure 5B:
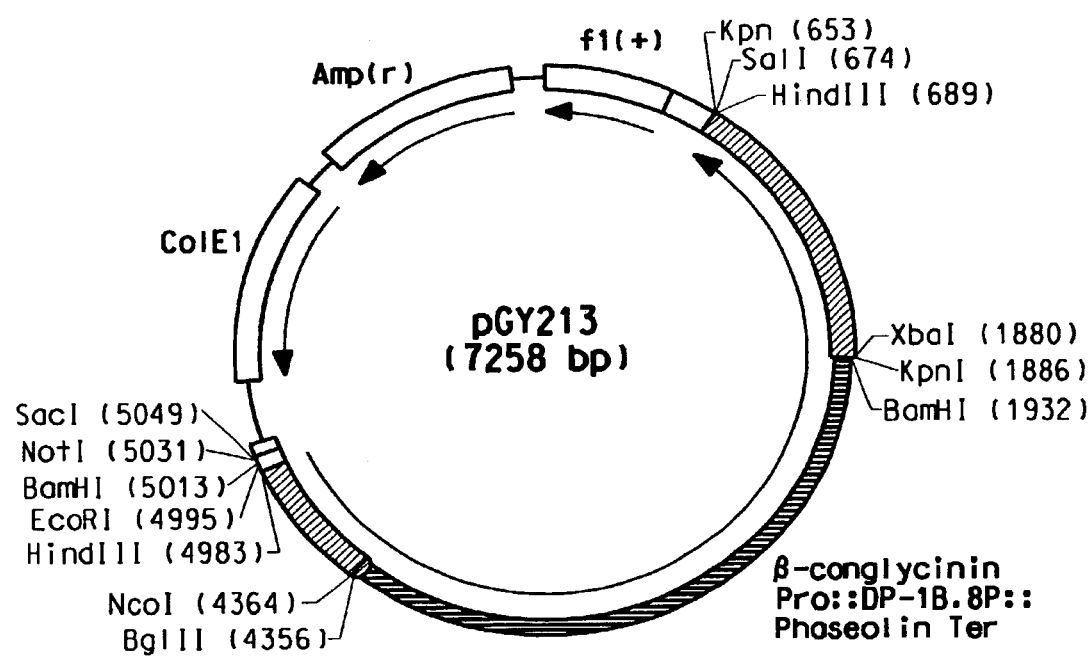
FIG. 5B is a plasmid map of pGY213 carrying the DP-1B.8P under the control of the β-conglycinin promoter having a reduced number of restriction sites.

Sequence of pCW109 indicates that it contains an empty expression cassette with a 5' β-conglycinin promoter and a 3' Phaseolin terminator (FIG. 3B). To insert DP-1B.8P into polylinker region immediately downstream β-conglycinin promoter, pCW109 and pGY101 were digested with restriction enzymes NcoI and KpnI, and then the DNA fragment containing DP-1B.8P from pGY101 was cloned into pCW109 between restriction sites of these two enzymes. The new plasmid was named pGY211 and contained an expression cassette consisting of β-conglycinin Pro::DP-1B.8P::Phaseolin Ter (FIG. 5A). To limit the restriction sites available in the polylinker, 1 μg of pGY211 was digested in a 30 μL reaction mixture with restriction enzymes EcoRI and XhoI at 37° C. for 2 hrs. Then, 2 μL of 2.5 mM dNTP, 17 μL water, and 1 μL Klenow fragment were added to the reaction mixture, and incubated for 10 min at room temperature to make blunt ends. The reaction was cleaned up by using QIAquick PCR Purification Kit. The new plasmid was obtained by self-ligation of one tenth of the reaction. To make more restriction sites available in regions flanking the expression cassette, the HindIII fragment from the plasmid, containing the entire expression cassette, was cloned into the HindIII site of pBluscript SK(+) in a positive orientation. This plasmid was designated pGY213 (FIG. 5B) and its orientation was confirmed by restriction digestion patterns.

Example 3

Construction Of Binary Vector-Based Plasmids

Figure 6:
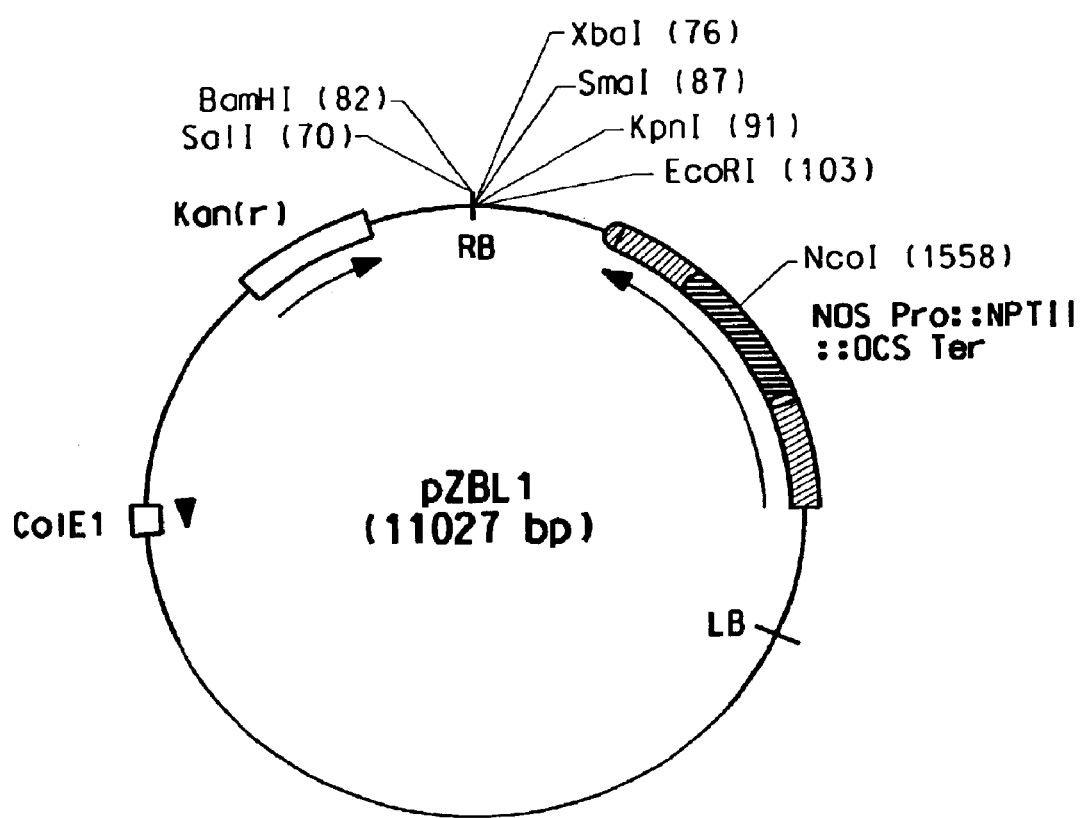
FIG. 6 is a plasmid map of binary vector pZBL1 carrying a T-DNA region with a NOS promoter driven NPTII gene.

The binary vector pZBL1 was provided by DuPont Agriculture Products (Wilmington, Del. 19898) and is fully described in U.S. Pat. No. 5,968,793 and is available from the American Type Culture Collection (ATCC 209128). The vector includes a kanamycin resistance gene outside the T-DNA region for bacteria selection, and a NPTII gene expression cassette (NOS Pro::NPTII::OCS Ter) inside the T-DNA region, between sequences of the right border (RB) and the left border (LB), for kanamycin resistance selection of plant cells (FIG. 6). All plasmids described in this example were generated in XL1-Blue *E. coli* cells except where mentioned.

Figure 7A:
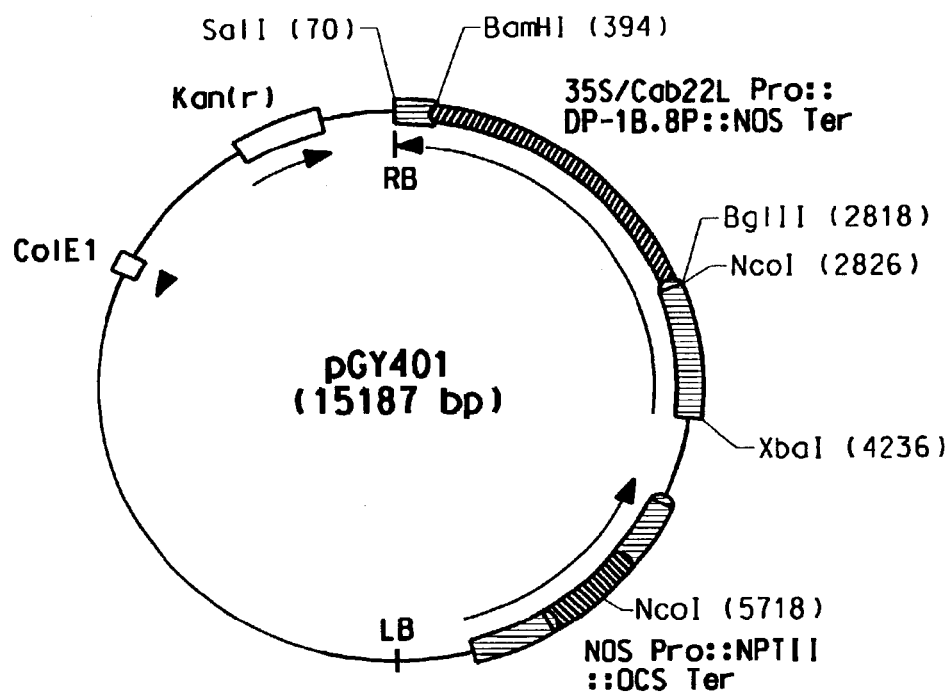
FIG. 7A is a plasmid map of pGY401, in which the T-DNA region includes an expression cassette comprising DP-1B.8P under the control of the 35S/Cab221 promoter in conjunction with the NOS driven NPTII.
Figure 7B:
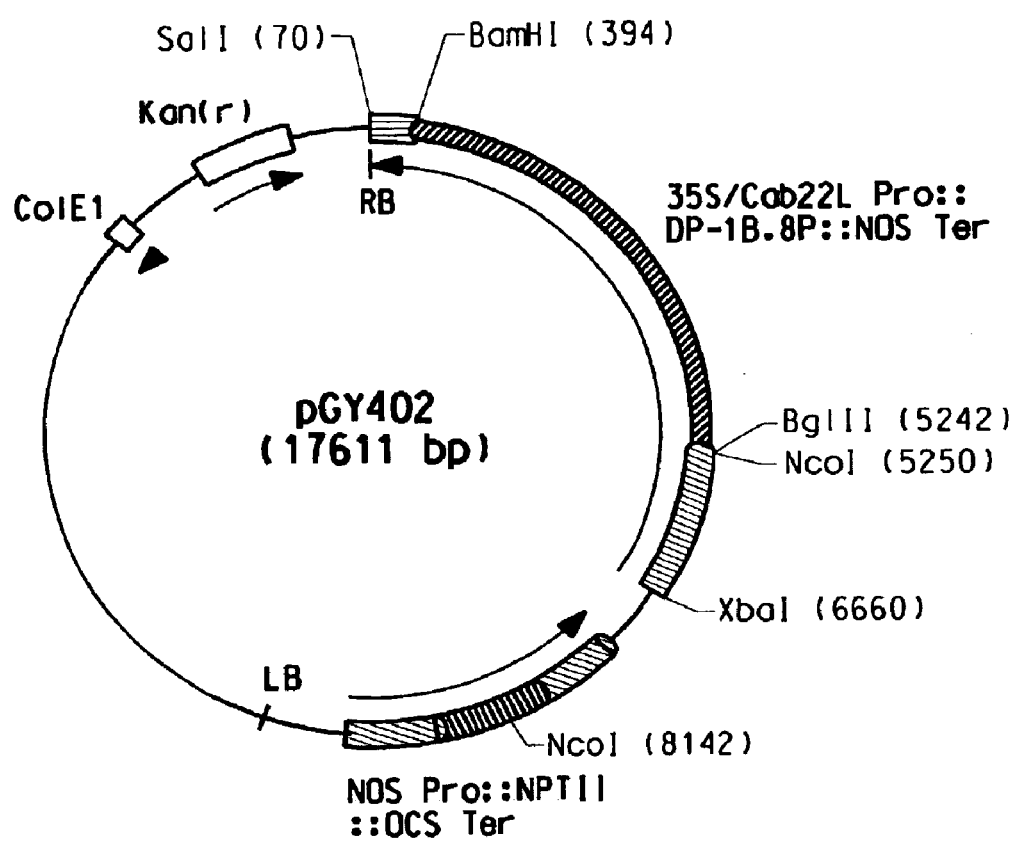
FIG. 7B is a plasmid map of pGY402 harboring an expression cassette containing DP-1B.16.P under the control of the 35S/Cab221 promoter within the T-DNA region.

To construct binary vector-based plasmids for constitutive expression of DP-1B proteins, plasmid pGY201 and pGY202 were digested by restriction enzymes XbaI and SalI. DNA fragments containing the DP-1B.8P and DP-1B.16P expression cassettes were isolated and inserted into the binary vector pZBL1 between restriction sites XbaI and SalI of the polylinker region, upstream of the NPTII expression cassette, respectively. The insertion resulted in plasmids pGY401, harboring an expression cassette 35S/Cab22L Pro::DP-1B.8P::NOS Ter, and pGY402, harboring an expression cassette 35S/Cab22L Pro::DP-1B.16P: :NOS Ter. Structures of both plasmids are detailed in FIGS. 7A and 7B. Their sequences were confirmed by digestion of unique restriction sites.

Figure 8A:
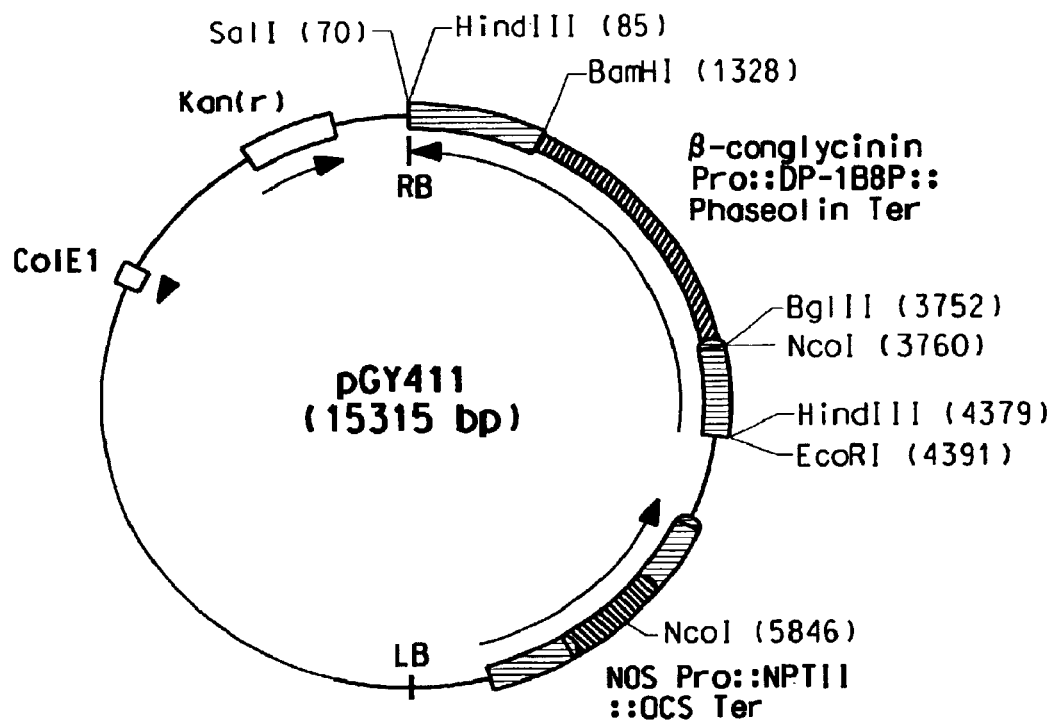
FIG. 8A is a plasmid map of pGY411 in which the T-DNA region includes the DP-1B8.P gene under the control of the β-conglycinin promoter.
Figure 8B:
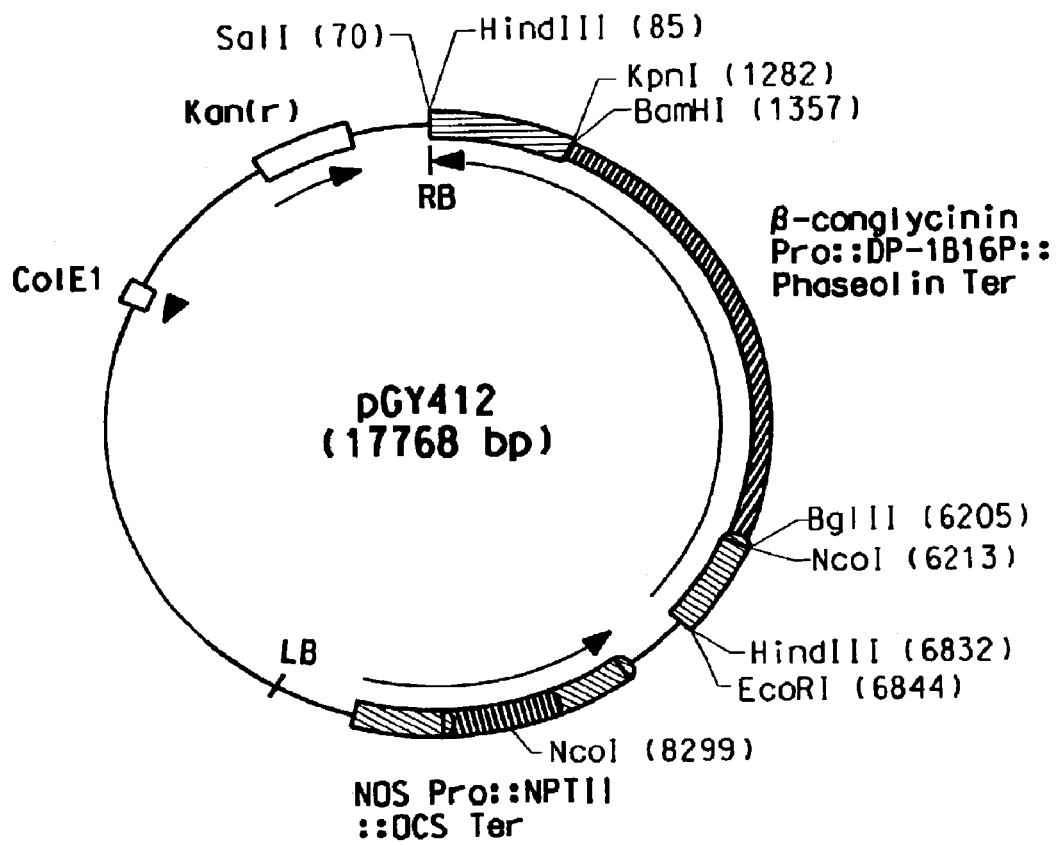
FIG. 8B is a plasmid map of pGY412 carrying the DP-1B16.P gene under the control of the β-conglycinin promoter within the T-DNA region.

Plasmid pGY411 was constructed for seed-specific expression of DP-1B.8P protein using a similar approach as described above. The DNA fragment containing DP-1B.8P expression cassette was obtained from pGY213 by digesting with restriction enzyme EcoRI and SalI and inserted into pZBL1 between these two sites. To make a construct for seed-specific expression of DP-1B.16P, pGY412 was constructed by substitution of the DP-1B.16P coding region (a DNA fragment from restriction site KpnI to BglII in pGY102) for the DP-1B.8P coding region (a DNA fragment between the same restriction sites in pGY411). DNAs for both plasmids were amplified in STBII *E. coli* cells to avoid DNA rearrangement, and the constructs were confirmed by digestion of unique restriction sites. As shown in FIGS. 8A and 8B, pGY411 and pGY412 include seed-specific expression cassettes consisting of β-conglycinin Pro::DP-1B.8P::Phaseolin Ter and β-conglycinin Pro::DP-1B.16P::Phaseolin Ter, respectively. The plasmids are summarized in Table 1.

Example 4

Agrobacterium-Mediated *Arabidopsis* Transformation

Agrobacterium Transformation

To prepare competent agrobacterial cells, a colony of C58C1(pMP90) agrobacterium strain (Koncz et al., *Mol. Gen. Genet.*, (1986) 204 (3), 383–396) were grown in 1 L YEP media, which includes 10 g Bacto peptone, 10 g yeast extract, and 5 g NaCl, until an $OD_{600}$ of 1.0. The culture was chilled on ice and the cells were collected by centrifugation. The competent cells were resuspended in ice cold 20 mM $CaCl_2$ solution and stored in –80° C. in 0.1 mL aliquots.

A freeze-thaw method was used to introduce pGY401, pGY402, pGY411, and pGY412 into agrobacteria. At first, 1 μg plasmid DNA from each of these constructs was added to the frozen aliquoted agrobacterial cells. The mixture was thawed at 37° C. for 5 min, added to 1 mL YEP medium, and then gently shaken at 28° C. for 2 hrs. Cells were collected by centrifugation and grown on a YEP agar plate containing 25 mg/L gentamycin and 50 mg/L kanamycin at 28° C. for 2 to 3 days. Agrobacterial transformants were confirmed by minipreparation and restriction enzyme digestion of plasmid DNA by routine methods, except that lysozyme (Sigma, St. Louis, Mo.) was applied to the cell suspension before DNA preparation to enhance cell lysis. An empty binary vector pZBL1 was also introduced into agrobacteria as a control.

*Arabidopsis* Transformation

*Arabidopsis thaliana* was grown to bolting in 3" square pots of Metro Mix soil (Scotts-Sierra, Maryville, Ohio) at a density of 5 plants per pot, under a controlled temperature of 22° C. and an illumination of 16 hrs light/8 hrs dark. Plants were decapitated 4 days before transformation. Agrobacteria carrying pZBL1(control), pGY401, pGY402, pGY411, or pGY412 plasmids were grown in LB medium (1% bacto-tryptone, 0.5% bacto-yeast extract, 1% NaCl, pH 7.0) containing 25 mg/L gentamycin and 50 mg/L kanamycin at 28° C., until the culture reached an $OD_{600}$ value of 1.2. Cells were collected by centrifugation and resuspended in infiltration medium (½×MS salt, 1×B5 vitamins, 5% sucrose, 0.5 g/L MES, pH 5.7, 0.044 µM benzylaminopurine) to $OD_{600}$ of approx. 0.8.

A vacuum infiltration method was employed to transfect the Arabidopsis plants with the agrobacterium strains which carried the five binary vector-based plasmids described above. Briefly, a 500 mL Magenta Box was filled with infiltration medium suspension of agrobacterium, and covered with a 3" square pot containing 5 Arabidopsis plants in an upside-down position, so that the entire plant was submerged in the suspension. The assembly was placed in an Isotemp Vacuum Oven model 281 (Fisher Scientific, Pittsburgh, Pa.)) and subjected to infiltration for 5 min under 30 mm Hg vacuum. At least 3 pots of plants were infiltrated by each of the agrobacterium strains. Infected plants were then laid on their sides in a Saran wrap sealed flat and incubated overnight at room temperature. The transfected Arabidopsis plants were grown to maturation under normal condition (22° C., 16 hrs light/8 hrs dark). Seeds from the transformed plants are defined as T1 seeds. T1 seeds were collected from plants in each pot, dried for one week, and stored at room temperature.

Example 5

Expression of DP-1B Proteins in Arabidopsis
Selection of Arabidopsis Transformants To select transformants, 1,000 T1 seeds were sterilized in 1 mL of 50% Clorox® (Chloral is ~10% bleach) and 0.02% Triton X-100 solution for 7 min, followed by 5 rinses in sterile distilled water. Seeds were resuspended in 2 mL of 0.1% agarose and spread on the top of a 90×20 mm plate containing primary selective medium (1×MS salt, 1×B5 vitamins, 1% sucrose, 0.5 mg/mL MES, pH 5.7, 30 µg/mL kanamycin, 100 µg/mL carbenicilin, 10 µg/mL benomyl, and 0.8% phytagar). After cold treatment at 4° C. for 3 days, seeds were allowed to germinate for one week at 22° C. under continuous illumination. Due to expression of the NTPII gene, all transformant seeds, which usually account for approximately 1% of the seed collection, germinated and grew into green seedlings. However, non-transformant seeds either did not germinate or their seedlings quickly became bleached. Healthy transformant seedlings, defined as T1 plants, were selected and grown on another 90×20 mm plate containing secondary selective medium, which had the same components as the primary selective medium except 15% phytagar. Transformants were grown for one week to enhance root development. Finally, the seedlings were transferred to individual 1" square pots of Metro Mix soil and grown to maturation at 22° C. and 16 hrs light/8 hrs dark cycle. T2 seeds produced by T1 plants were collected from each individual plant and stored separately.

All the T1 seed collections of pZBL1, pGY401, pGY402, pGY411, and pGY412 were subject to the transformant selection described above. This process resulted in 22 transgenic plants for pZBL1, 44 for pGY401, 69 for pGY402, 21 for pGY411, and 29 for pGY412.

Examination of DP-1B Protein Expression

T1 transgenic plants carrying the pGY401 and pGY402 constructs were selected and grown in soil until bolting as described above. Half of a healthy leaf (approximately 20 mg of leaf tissues) from each plant was ground with 50 µL protein extract buffer (50 mM Tris-HCl, pH 8.0, 12.5 mM $MgCl_2$, 0.1 mM EDTA, 2 mM DTT, 5% glycerol) in 1.5 mL ice-cold Eppendorf tubes. The mixtures were centrifuged and the supernatants were collected as leaf protein extracts for examination of constitutively expressed DP-1B protein. Seed protein extracts were prepared from T2 seeds carrying pGY411 and pGY412 constructs, which had been harvested from the selected T1 transgenic plants as described above. 100 to 200 seeds from each transgenic plant were extracted in 400 µl of protein extract buffer. Seed protein extracts were used to examine seed-specific expression of DP-1B protein. Total protein concentrations in these extracts were determined by using Bio-Rad Protein Assay Reagent (Bio-Rad, Hercules, Calif.).

The protein immuno-blot assay described in Current Protocols in Molecular Biology (F. M. Ausubel et al., edt, Wiley Interscience) was employed to determine expression of DP-1B protein. Proteins in leaf protein extract or seed protein extract were separated in a mini-polyacrylamide gel (5% stack gel and 10% separate gel) using a Bio-Rad mini-gel electrophoresis apparatus. Using a Pharmacia-LKB 2117 multiphor II (Amersham Pharmacia Biotech, Piscataway, N.J.), proteins in the gel were transferred to a 0.2 µM nitrocellulose membrane (Schleicher & Schuell, Keene, N.H.) for 1 hr at 0.8 $mA/cm^2$ using a semi-dry transfer method recommended by the manufacturer. One liter of semi-dry western transfer buffer included 2.93 g glycine, 5.81 g Tris, 0.375 g SDS, and 200 mL methanol. The nitrocellulose membrane-was blocked with 5% non-fat milk TTBS (0.1% Tween-20, 2.42 g Tris, 29.2 g NaCl, pH 7.5), incubated in the primary antibody-TTBS solution for 3 hrs, and then in TTBS containing anti-rabbit IgG HRβ-conjugate (Promega, Madison, Wis.) for 1 hr. Protein-antibody interaction on the membrane was detected by a chemiluminescent substrate solution, which consisted of 100 mM Tris-HCl buffer (pH 8.5) containing 0.2 mM β-coumaric acid, 2.5 mM 3-aminophthalhydrazide and 0.01% $H_2O_2$. The results were visualized by exposure to X-ray film.

Figure 9A:
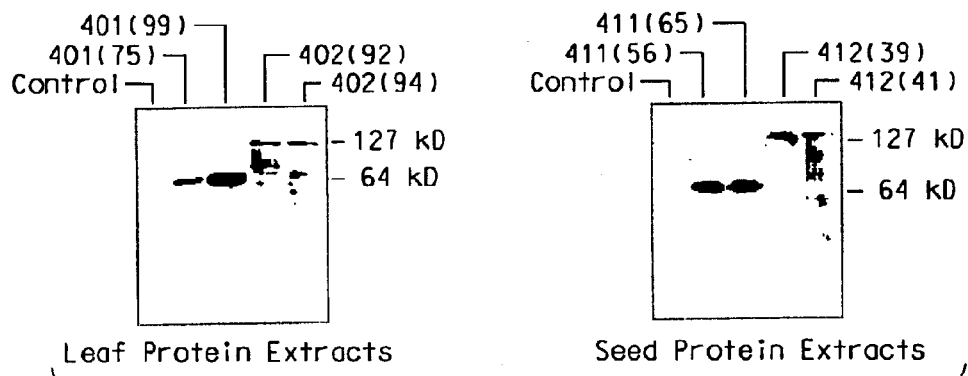
FIG. 9A is an immunoblot showing accumulation of DP-1B protein in leaves and seeds of T1 transgenic Arabidopsis.

To examine expression of DP-1B proteins, 10 µL leaf protein extracts from pGY401 and pGY402 transgenic Arabidopsis and 10 µL seed protein extracts from pGY411 and pGY412 transgenic Arabidopsis were subjected to protein immuno-blot assay. Ten µL leaf and seed protein extracts from pZBL1 transgenic Arabidopsis were also used as controls. The primary antibody, DP-1B Abs, was obtained from DuPont, the preparation of which is fully described in WO 9429450. These antibodies recognize the highly conserved sequence CGAGQGGYGGLGSGGAGRG (SEQ ID NO:25) in the DP-1B molecule, and were used in a 1:1,000 dilution. FIG. 9A illustrates the results from the protein immuno-blot assay, indicating that the 64 kD DP-1B.8P and 127 kD DP-1B.16P proteins were produced and accumulated in leaf tissues of pGY401 and pGY402 transgenic Arabidopsis, and that the both proteins were also produced and accumulated in seeds of pGY411 and pGY412 transgenic Arabidopsis, respectively. A higher ratio of smaller fragment of DP-1B.16P proteins accumulated in leaves of pGY402 plants and seeds of some pGY412 plants indicating that production of DP-1B protein in Arabidopsis prefers the 8-mer to the 16-mer. Using this assay, 163 transgenic Arabidopsis with kananmycin-resistance phenotype (44 for pGY401, 69 for pGY402, 21 for pGY411, and 29 for pGY412) were examined for DP-1B expression. Only 25 pGY401 plants (57%), 4 pGY402 plants (6%), 4 pGY411 plants (19%), and 7 pGY412 plants (24%) produced and accumulated DP-1B protein products with expected molecular masses.

TABLE 1

A Summary for Plasmid Constructs

| Construct | Recipient | Donator | Insertion | Usage |
|---|---|---|---|---|
| pGY001 | pBS-SK(+) | — | Adapter GYS | Adapter |
| pGY101 | pGY001 | pFP717 | 8xDP-1B.33 | DP-1B.8P |
| pGY102 | pGY001 | pFP723 | 16xDP-1B.33 | DP-1B.16P |
| pGY201 | pML63 | pGY101 | DP-1B.8P | 35S/Cab22L Pro:: DP-1B.8P::NOS Ter |
| pGY201 | pML63 | pGY102 | DP-1B.16P | 35S/Cab22L Pro:: DP-1B.16P::NOS Ter |
| pGY211 | pCW109 | pGY101 | DP-1B.8P | Beta-conglycinin Pro:: DP-1B.8P::Phaseolin Ter |
| pGY213 | pBS-SK(+) | pGY211 | DP-1B.8P | Beta-conglycinin Pro:: DP-1B.8P::Phaseoline Ter |
| pGY401 | pZBL1 | pGY201 | 35S Pro::DP-1B.8P:: NOS Ter | Constitutive expression of DP-1B.8P in Arabidopsis |
| pGY402 | pZBL1 | pGY202 | 35S Pro::DP-1B.16P:: NOS Ter | Constitutive expression of DP-1B.16P in Arabidopsis |
| pGY411 | pZBL1 | pGY213 | Cong Pro::DP-1B.8P:: Pha Ter | Seed-specific expression of DP-1B.8P in Arabidopsis |
| pGY412 | pGY411 | pGY102 | Cong Pro::DP-1B.16P:: Pha Ter | Seed-specific expression of DP-1B.8P in Arabidopsis |
| pLS3 | pZBL102 | pGY213 | Cong Pro::DP-1B.8P:: Pha Ter | Expression of DP-1B.8P in Soy somatic embryos |
| pGY220 | pGY213 | pGY412 | Cong Pro::DP-1B.16P:: Pha Ter | Beta-conglycinin Pro:: DP-1B.16P::Phaseolin Ter |
| pLS4 | pZBL102 | pGY220 | Cong Pro::DP-1B.16P:: Pha Ter | Expression of DP-1B.16P in Soy somatic embryos |

The remaining transgenic *Arabidopsis*, which had been selected by their antibiotics-resistance phenotypes, belonged to the following three categories:

(1) Plants showed no visible accumulation of DP-1B protein in the assay;

(2) Plants expressed DP-1B proteins but were sterile or died before maturation;

(3) Plants accumulated DP-1B protein with wrong molecular mass or/and multiple dominant products. The fact that few transgenic plants successfully produced DP-1B proteins reflects the difficulty in getting expression of SLP's in plants, possibly due to high repetitive and high glycine/alanine enriched nature of spider silk.

Anti-His (C-term)-HRP (Invitrogen, Carlsbad, Calif.) was also used as a primary antibody in the protein immuno-blot assay. Because 6xhistidine tag was built into C-terminus of DP-1B protein in all constructs, the anti-His tag conjugate enabled us to determine the quality and estimate the yield of DP-1B proteins conveniently. When using this antibody for immuno-blot, the secondary antibody was not necessary and protein-antibody interaction could be detected directly by chemiluminesent reagents.

Figure 9B:
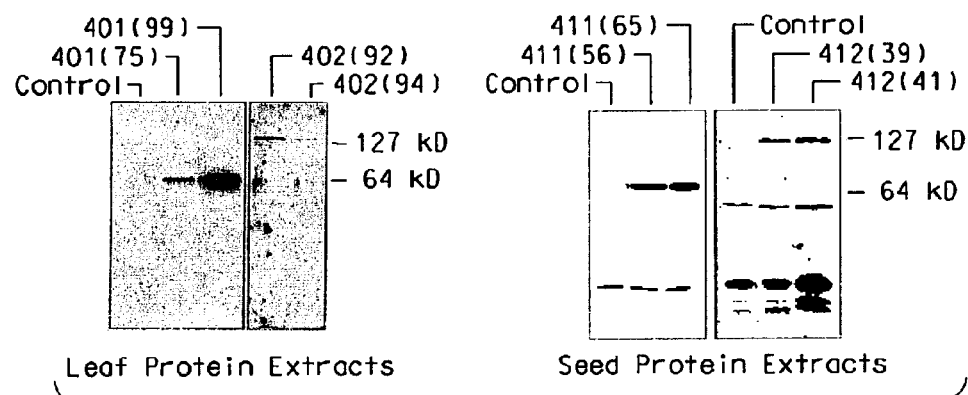
FIG. 9B is an immunoblot showing complete C-terminus of the DP-1B protein.

To determine the quality of DP-1B proteins produced in transgenic *Arabidopsis*, leaf or seed protein extracts from those 40 plants, which demonstrated expected expression of DP-1B proteins, were subjected to immuno-blot assays. Anti-His (C-term)-HRP was used in a 1:4,000 dilution as the primary antibody. FIG. 9B illustrates the results from this assay. The results indicated that expressed DP-1B proteins in those plants had not only the correct molecular masse but also the complete C-termini, since their C-terminal His-tags were recognized by anti-His (C-term)-HRP. Shorter fragment ladders of DP-1B.16P protein, which were detected by DP-1B Abs in some of protein extracts such as 402(92), 402(94), and 412(41) of FIG. 9A, were not recognized by the His-tag Ab, suggesting that some premature terminations might have occurred during the translation of DP-1B. 16P. When interacting with seed proteins, anti-His (C-term)-HRP also recognized a few smaller protein molecules, as shown in the right panel of FIG. 9B. Since these proteins could also be distinguished from the control, it is assumed that they were seed proteins rather than products of transgenes.

In a similar immuno-blot assay using Anti-His (C-term)-HRP, a 14 kD recombinant protein with 6xHis tag at the C-terminus, which was produced in *E. coli* and purified through affinity columns, was used as a standard protein. By comparing signals of the standard protein and protein extracts from the transgenic plants, yields of DP-1B protein in most of those 40 plants were estimated. Yields of DP-1B.8P protein in leaves of pGY401 transgenic plants were between 0.01% and 1.65% of total soluble leaf protein (approximately between 0.002% and 0.33% of dry weight), which represented an average yield of 0.34% of total soluble leaf protein (approximately 0.07% of dry weight). Yields of DP-1B.16P protein in leaves of pGY402 transgenic plants were between 0.01% and 0.06% of total soluble leaf protein (approximately between 0.002% and 0.01% of dry weight), which represented an average yield of 0.03% of total soluble leaf protein (approximately 0.006% of dry weight). Yields of DP-1B.8P protein in seeds of pGY411 transgenic plants were between 1% and 1.4% of total soluble seed protein (approximately between 0.2% and 0.28% of dry weight), which represented an average yield of 1.2% of total soluble seed protein (approximately 0.24% of dry weight). Yields of DP-1B.16P protein in seeds of pGY412 transgenic plants were between 0.5% and 1% of total soluble seed protein (approximately between 0.1% and 0.2% of dry weight), which represented an average yield of 0.78% of total soluble seed protein (approximately 0.16% of dry weight). A summary of the expression results is shown in Table 2.

TABLE 2

DP-1B Yields in Transgenic Arabidopsis Plants

| Transgene | Product | Examined Tissue | Yield Range (%) | | Average Yield (%) | |
|---|---|---|---|---|---|---|
| | | | of total soluble protein | of dry weight | of total soluble protein | of dry weight |
| pGY401 | DP-1B.8P | Leaves | 0.01–1.65 | 0.002–0.33 | 0.34 | 0.07 |
| pGY402 | DP-1B.16P | Leaves | 0.01–0.06 | 0.002–0.01 | 0.03 | 0.006 |
| pGY411 | DP-1B.8P | Seeds | 1–1.4 | 0.2–0.28 | 1.2 | 0.24 |
| pGY412 | DP-1B.16P | Seeds | 0.5–1 | 0.1–0.2 | 0.78 | 0.16 |

After an extended screening of pGY401 transgenic *Arabidopsis*, one plant was identified which accumulated 65 kD DP-1B.8P protein up to 9.2% of total soluble leaf protein (approximately 1.8% of dry weight), not shown in Table 2. These results suggested that, in general, seed-specific expressions (pGY411 and pGY412) led to higher levels of both DP-1B.8P and DP-1B.16P proteins in seeds than constitutive expression (pGY401 and pGY402) in leaves.

Confirmation of T-DNA Insertion into *Arabidopsis* Genomes

Figure 9C:
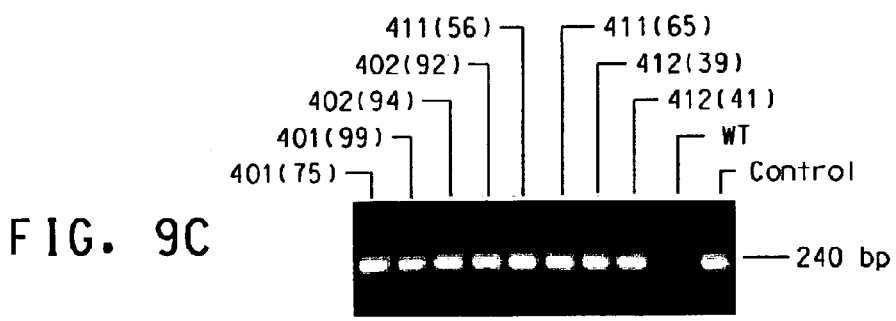
FIG. 9C is a DNA agrose gel showing the transgene in Arabidopsis chromosome.

During *Arabidopsis* transformation, the entire T-DNA sequence, which included NPTII expression cassette and DP-1B.8P or DP-1B. 16P expression cassette was inserted into the plant genome. To further relate the expression of DP-1B proteins in those 40 transgenic *Arabidopsis* to the transgenes, polymerase chain reaction (PCR) was employed to detect a DNA fragment within the T-DNA region from genomic DNA of those plants. For this purpose, 2 leaves (approximately 100 mg) were collected from each transgenic *Arabidopsis*. DNA was then isolated using DNeasy Plant Mini Kit, following a protocol provided by kit manufacturer (Qiagen, Valencia, Calif.), and 50 μL of a DNA solution was obtained. The DNA concentration and purity of each preparation was estimated by measuring $OD_{260}$ and $OD_{280}$ values in a Beckman DU640 Spectrophotometer (Bechman Instruments, Fullerton, Calif.). Since direct amplification of DP-1B coding regions was difficult due to its highly repetitive nature, primer NPTII-F2 (5' GCT,CGA, CGT,TGT,CAC,TGA,AG 3') (SEQ ID NO:26) and NPTII-R2 (5' TCG,TCC,AGA,TCA,TCC,TGA,TC 3')(SEQ ID NO:27) were synthesized by standard means and used to amplify a 240 bp segment of the NPTII gene. One 25 μL PCR reaction included 1 μL DNA, 2.5 μL 10×PCR reaction buffer (Life Technologies, Gaithersburg, Md.), 0.25 mM each of dNTP, 2 mM MgCl2, 10 pmole primer for NPTII-F2, 10 pmole primer for NPTII-R2, and 1.25 units of Taq DNA polymerase (Life Technologies, Gaithersburg, Md.). Reactions were conducted on a GeneAmp PCR System 960 (Perkin-Elmer, Norwalk, Conn.) for 35 cycles of 45 sec at 94° C., 45 sec at 58° C., and 45 sec at 72° C., and then separated on an electrophoretic argrose gel containing ethidium bromide. Results were visualized under UV light. Analysis of the gel indicated that the T-DNAs had been integrated into genomic DNAs of all 40 transgenic *Arabidopsis* as expected. The results are shown in FIG. 9C. Because the DNA sample for the control was prepared from a pZBL1 transgene plant, which carries NPTII gene but not DP-1B gene, a 240 bp NPTII fragment was amplified from it by PCR. Therefore, the DNA sample from wild type (WT) *Arabidopsis* was used in this assay as a negative control.

Demonstration of Transgene Heritability

Figure 10A:
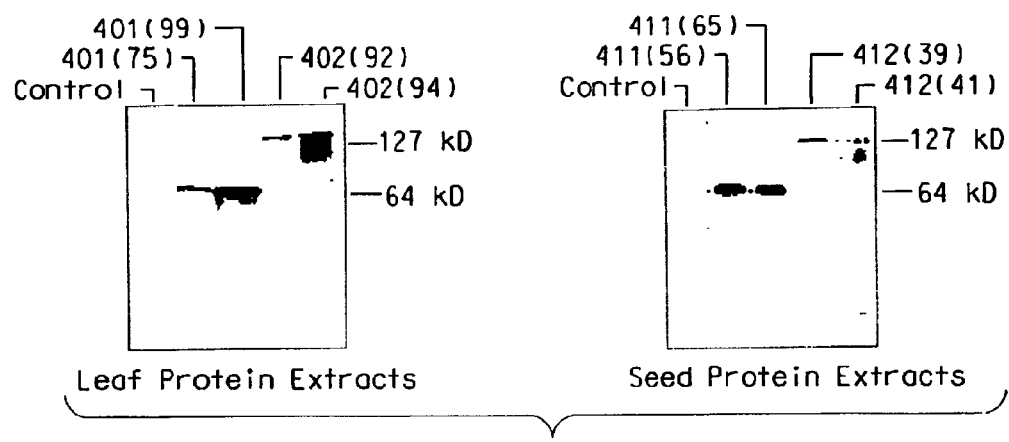
FIG. 10A is an immunoblot showing accumulation of DP-1B protein in leaves and seeds of T2 transgenic Arabidopsis.

To test transgene heritability, two transgenic *Arabidopsis* plants were chosen containing each of pGY401, pGY402, pGY41 1, and pGY412 constructs. T2 seeds were cold-treated for 3 days and then germinated on primary selective medium for 10 days. Thirty healthy kanamycin resistance T2 seedlings, which were expected to contain the transgene, were transferred and grown in Metro Mix soil under the conditions described above. Protein extracts were prepared from leaves of bolting plants of pGY401 and pGY402 and seeds of mature plants from the pGY411 and pGY412 transformants. An immuno-blot assay, using a polyclonal antibody against the highly conserved peptide sequence of DP-1B protein (DP-1B Abs), demonstrated that DP-1B. 8P and DP-1 B.16P proteins were produced and accumulated in T2 progenies of the transgenic plants in a tissue-specific manner (FIG. 10A). Smaller peptide fragments of DP-1B.16P protein also accumulated in T2 plants of 402 (92), 402(94), and 412(41) in similar patterns as seen in their T1 parents.

Figure 10B:
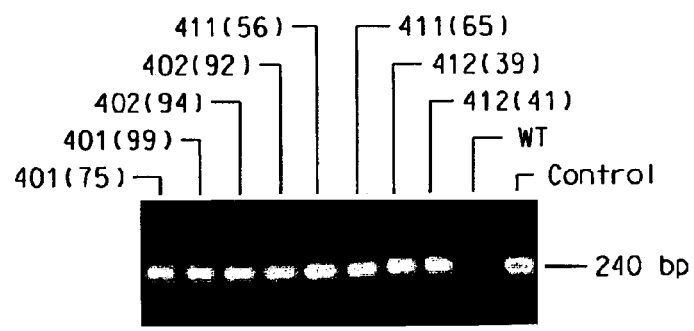
FIG. 10B is a DNA agrose gel showing the transgene in the chromosome of T2 Arabidopsis.

DNA was also isolated from leaves of these T2 progenies. PCR amplification of 240 bp NPTII fragment was carried out for each DNA sample, following the protocol described above. DNA samples from wild-type (WT) *Arabidopsis* was used as a negative control since the control DNA of pZBL1 transgenic plant contained the NTPII sequence. PCR reactions were then subjected to electrophoresis on an argrose gel containing ethidium bromide. The gels were visualized under UV light (FIG. 10B), and indicated that the genomes of all these T2 progenies still carried the transgenes.

Along with examining transgenes expression, the germination and development of these T2 plants were also analyzed. A comparison of the T2 plants with the control plants (pZBL1) during their growth showed no phenotypic abnormality among T2 plants in spite of expression of transgenes.

In conclusion, these results demonstrated that the DP-1B gene, which was introduced into the *Arabidopsis* genome using constructs pGY401, pGY402, pGY411, and pGY412, were heritable and stable through sexual reproduction.

Example 6

Figure 11A:
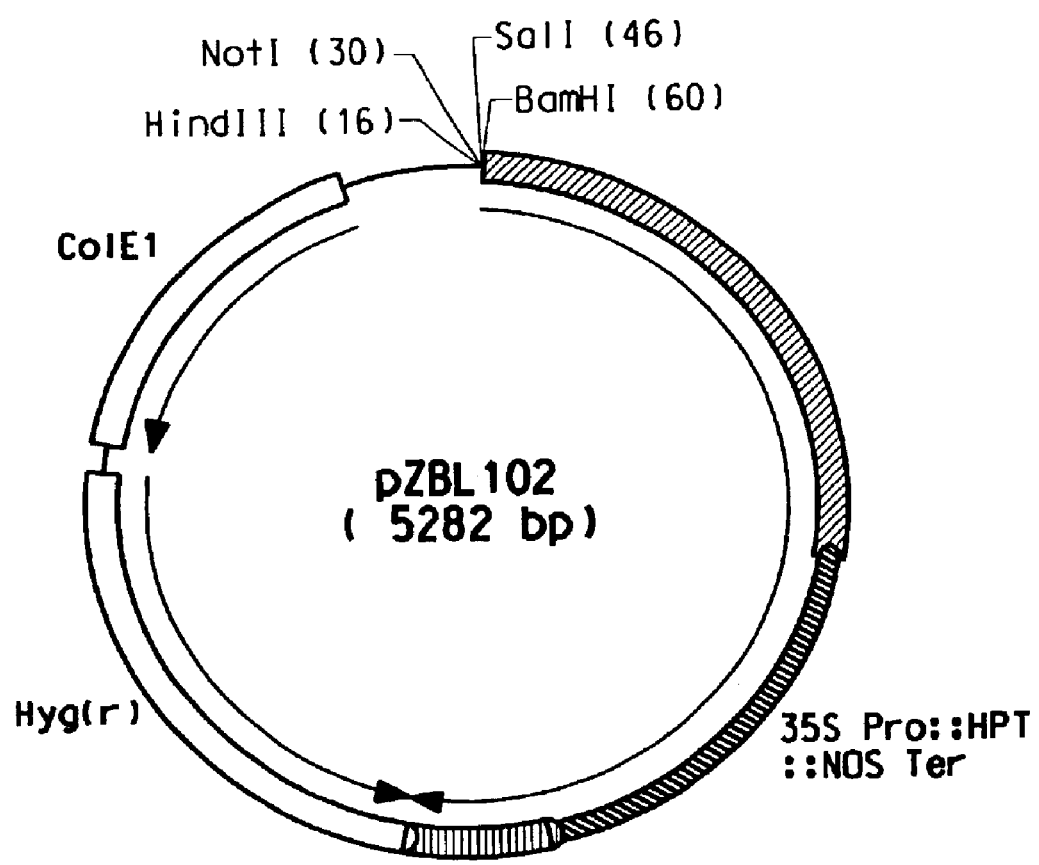
FIG. 11A is a plasmid map of pZBL102 carrying the HPT gene under the control of the 35S promoter.

Construction of Plasmids Containing Synthetic Genes for Analogs of *Nephila clavipes* Spidroin 1 for Expression in Soy Somatic Embryos Plasmid pZBL102 was provided by DuPont Agricultural Products (Wilmington, Del. 19898). This plasmid was used to make constructs for DP-1B protein expression in soy somatic embryos. This pSP72 (Promega, Madison, Wis.)-based plasmid contains an hygromycin B phosphotransferase (HPT) gene directed by T7 promoter (T7 Pro-::HPT::T7 Ter) for hygromycin B resistance in bacterium and an expression cassette of 35S Pro::HPT::NOS Ter for hygromycin B resistance in plant cells, as shown in FIG. 11A. Because of the highly repetitive nature of the DP-1B coding sequences, all plasmids in this example were generated in STBII *E. coli* cells.

Figure 12A:
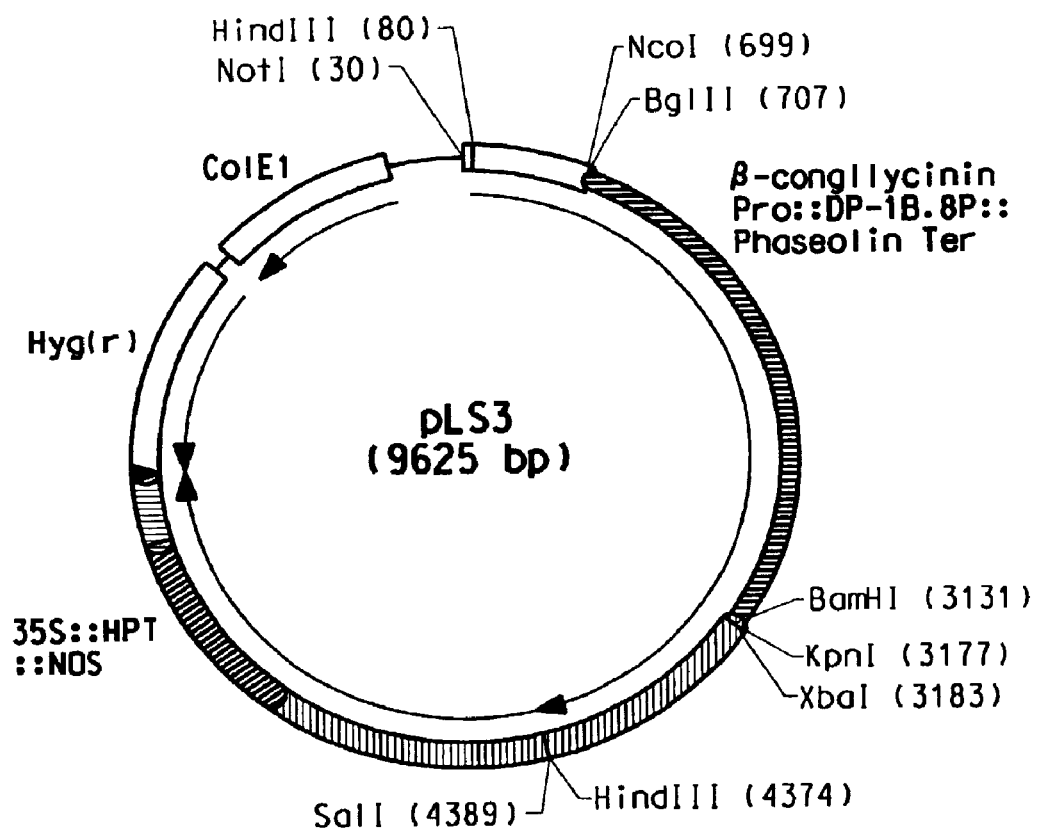
FIG. 12A is a plasmid map of pLS3 carrying the β-conglycinin promoter -DP-1B.8P construct for transformation of soy embryos.

To make a construct for expression of DP-1B.8P protein in soy somatic embryos, plasmid pZBL102 was digested with NotI and SalI. The linearized vector was separated from a short NotI/SalI DNA fragment on an argrose gel and purified using QIAquick Gel Extract Kit. Using the same method, plasmid pGY213 was also digested by NotI and SalI and a 4357 base pair DNA fragment containing a seed-specific expression cassette consisting of β-conglycinin Pro::DP-1B.8P::Phaseolin Pro was isolated. This DNA fragment was ligated with the linearized pZBLT102 between the NotI and SalI sites in an orientation which was the same as that for the 35S Pro::HPT:: NOS Ter expression cassette. The new construct was designated pLS3. Its structure is shown in FIG. 12A.

Figure 11B:
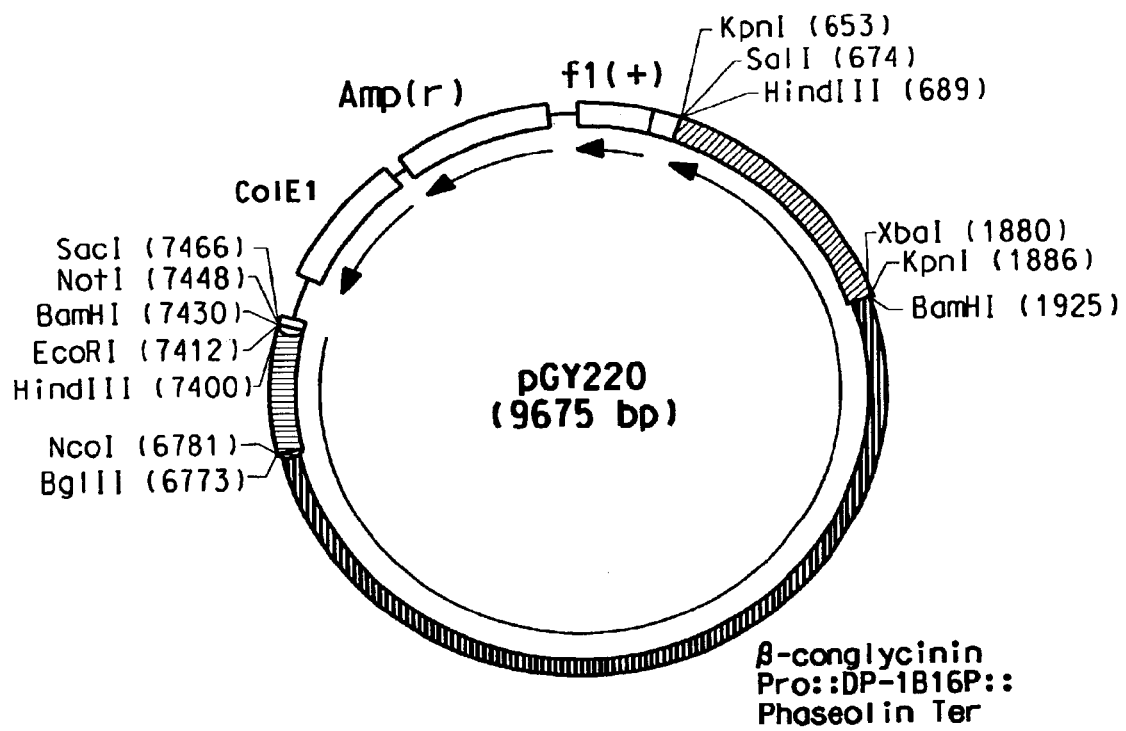
FIG. 11B is a plasmid map of pGY220 carrying the DP-1B.16P under the control of the b-conglycinin promoter.

Construction of a plasmid for expression of DP-1B. 16P protein in soy somatic embryos required a modified plasmid pGY412. For this purpose, the DNA fragment between KpnI (1282) and EcoRI (1330) sites of pGY412 was replaced by a short sequence that only included a SmaI site. This modified pGY412 was then digested with SalI and NcoI, and a DNA fragment containing the DP-1B.16P coding region and the Phaseolin terminator sequence was isolated and ligated into pGY213 between SalI and NcoI sites. This fragment was thus substituted for the DP-1B.8P coding region and resulted in plasmid pGY220. FIG. 11B shows structure of plasmid pGY220, which contains a seed-specific expression cassette consisting of β-conglycinin Pro::DP-1B.16P::Phaseolin Ter.

Figure 12B:
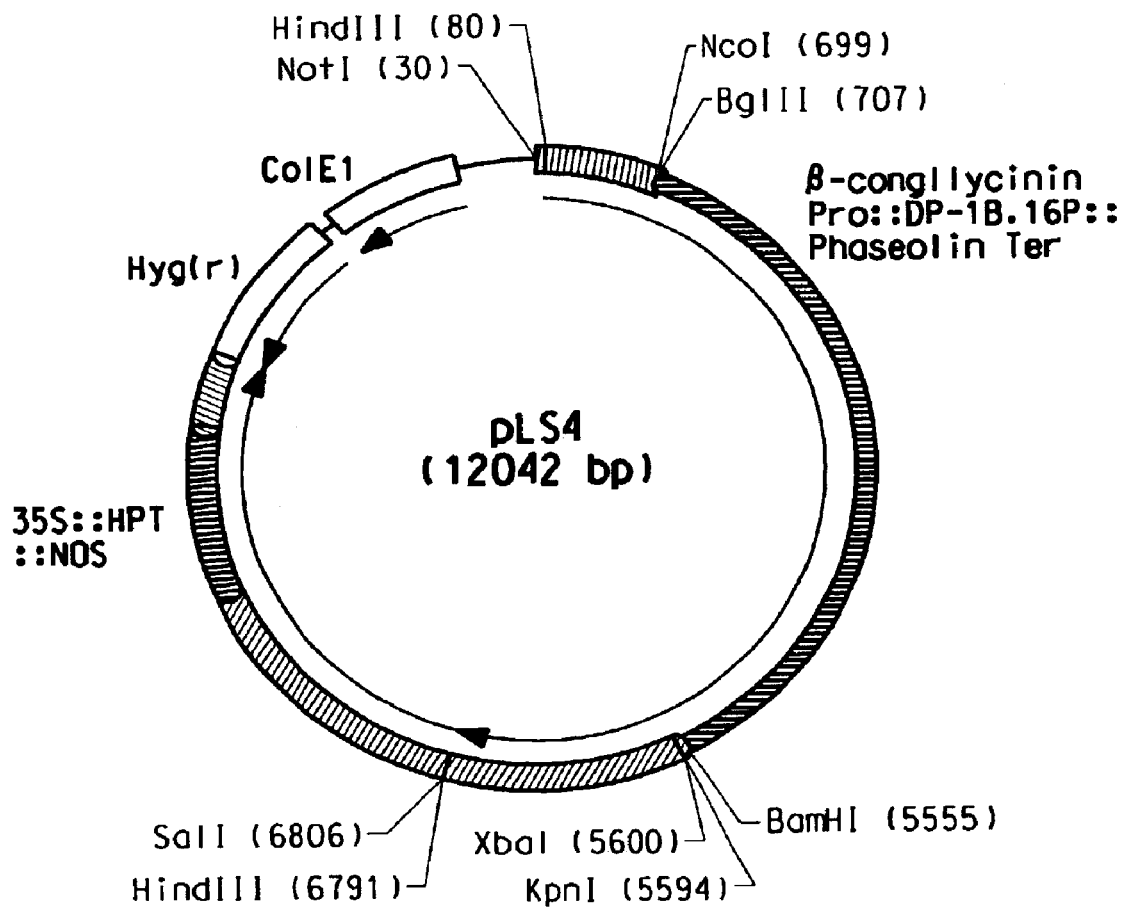
FIG. 12B is a plasmid map of pLS4 carrying the β-conglycinin promoter -DP-1B.16P construct for transformation of soy embryos.

In a similar manner plasmid pGY220 was digested with NotI and SalI. A 6774 base pair DNA fragment containing a seed-specific expression cassette consisting of β-conglycinin Pro::DP-1B.16P::Phasolin Ter was isolated and ligated with the linearized pZBL102 between the NotI and SalI sites. The new plasmid, pLS4, was almost identical to pLS3, except it contained the DP-1B.16P coding region instead of the DP-1B.8P region. Its structure is shown in FIG. 12B.

Example 7

Transformation and Expression of DP-1B Gene in Soy Somatic Embryos Soy Somatic Embryonic Cell Transformation by Particle-Gun Bombardment Plasmids pLS3 and pLS4 were used in soy somatic embryonic cell transformation in order to express the 8-mer and 16-mer DP-1B protein, respectively. Prior to transformation, both plasmids were amplified and purified from STBII E. coli cells on a large scale. STBII cells carrying with pLS3 or pLS4 were grown in 500 mL of LB-hygromycin broth (10 g/L Bacto tryptone, 5 g/L yeast extract, 5 g/L NaCl, 150 mg/L hygromycin B), at 37° C. overnight, and collected by centrifugation. The cells were then resuspended in 6 mL of solution I (25 mM Tris pH 7.5, 10 mM EDTA, 15% sucrose, 2 mg/mL lysozyme), lysed by adding 12 mL of solution II (0.2 M NaOH, 1% SDS), and then neutralized by adding 7.5 mL of 3 M NaAc, pH 4.6. Supernatant of the lysate was collected by centrifugation, and subjected to 50 µg RNase A treatment at 37° C. for 30 min, phenol/chloroform extraction, and ethanol precipitation. The DNA pellet was resuspended in 1 mL $H_2O$ and precipitated again by mixing with 1 mL 1.6 M NaCl and 2 mL 13% PEG-800. Pure DNA was washed with 70% ethanol and resuspended in $H_2O$ with a final concentration of 1 µg/µL.

Two week-old suspension cultures of soy somatic embryonic cells Asgro 2872/821 were transformed with plasmid pLS3 and pLS4 using particle gun bombardment (U.S. Pat. No. 5,955,650). The bombardment was carried out in a DuPont Biolistic PDS1000/HE instrument (helium retrofit) at 1100 psi membrane rupture pressure and 27–28 in. Hg chamber vacuum. Ten plates of cells were transformed for each construct, by double bombardments. Following bombardment, cells were incubated for 11 days in SB172 (4.6 g/L Duchefa MS salt, 1 mL/L 1,000×B5 vitamins, 10 mg/L 2,4-D, 60 g/L sucrose, 667 mg/L asparagine, pH 5.7), and transformant clones were selected over the next 2 months in SB172 containing 50 mg/L hygromycin B. Sixty pLS3 and thirty pLS4 transformant clones were chosen for further maturation of embryonic tissue by sequentially culturing them following a three-step schedule: (1) 1 week on SB166 (34.6 g/L Gibco/BRL MS salts, 1 mL/L 1,000×B5 vitamins, 60 g/L maltose, 750 mg/L $MgCl_2$ hexahydrate, 5 g/L activated charcoal, 2 g/L gelrite, pH 5.7); (2) 3 weeks on SB103 (as same as SB166 but without activated charcoal); (3) 2 weeks on SB148 (as same as SB103 except that 7 g/L agarose were substituted for 2 g/L gelrite). During the course of experiment, tissue cultures in both liquid and solid media were maintained under a controlled condition of 26° C., 16:8 hr day/night photoperiod, and light intensity of 30–35 µE/m2s.

Examination of DP-1B Protein Expression in Soy Somatic Embryos

Mature soy somatic embryo clumps were transformed with pLS3 and pLS4. Each clump represented an independent transformation event and displayed a hygromycin B resistance phenotype. Because it is believed that entire bombarded plasmid will integrate into chromosomes of embryonic cells in most transformation events, the seed-specific DP-1B expression cassettes of pLS3 and pLS4 should be present in those chromosomes and therefore express DP-1B protein.

To examine DP-1B protein expression in the transgenic soy somatic embryos, the protein extracts were prepared from approximately 200 mg of the pLS3 and pLS4 transgenic embryonic tissues by grinding in 200 µL protein extract buffer in a biopulverizer (FastPrep FP120, BIO101, Vista, Calif.). Supernatants were collected by centrifugation and protein concentrations were determined by using Bio-Rad Protein Assay Reagent. Wild-type soy embryonic tissue was employed as a control for the experiment. These protein extracts were used in protein immuno-blot assay to determine qualities and quantities of DP-1B protein expression in the transgenic soy embryonic tissues, following a method described in the *Arabidopsis* transformation section.

For the immuno-blot assay, the soluble proteins from 10 µL of embryonic protein extract were separated by SDS-PAGE, transferred to nitrocellulose membrane, and then detected using DP-1B Abs. Because of cross-reactions between the antibodies and the embryonic proteins many non-DP-1B proteins were detected by the antibodies from protein extracts of the transformants and control. However, the results still clearly indicated that the 65 kD DP-1B.8P protein had accumulated to significant levels in seven pLS3 embryonic transformants. No detectable 127 kD DP-1B. 16P protein had accumulated in any of 30 pLS4 transformants. Additionally, a few of DP-1B.8P transgenic soy somatic embryos also accumulated smaller proteins which were recognized by the DP-1B Abs, suggesting possible DNA recombination or other molecular modifications during transgene expression. Expression levels of DP-1B.8P in those seven pLS3 embryonic transformants were estimated by an immuno-blot assay, probing with anti-His (C-term)-HRP Ab, as described previously. The results are summarized in Table 3.

TABLE 3

DP-1B Yields in Transgenic Soy Embryos

| Transgene | Product | Examined Tissue | Yield Range (%) | | Average Yield (%) | |
|---|---|---|---|---|---|---|
| | | | of total soluble protein | of dry weight | of total soluble protein | of dry weight |
| pLS3 | DP-1B.8P | Embryos | 0.54–1.64 | 0.22–0.66 | 1.0 | 0.4 |
| pLS4 | DP-1B.16P | Embryos | None | None | None | None |

As shown in Table 3, the expression levels of DP-1B.8P ranged from 0.54% to 1.64% of total soluble soy embryonic proteins (approximately from 0.22% to 0.66% of dry weight), with an average yield of 1.0% of total soluble soy embryonic proteins (approximately 0.4% of dry weight). (Author's note: assume that 40% of dry weight is protein and all proteins are soluble in embryonic tissue.)

Figure 13A:
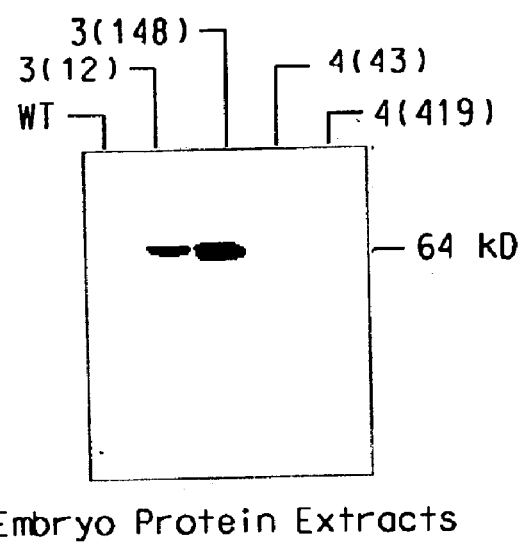
FIG. 13A is an immunoblot showing accumulation of DP-1B protein in transgenic soy somatic embryos.
Figure 13B:
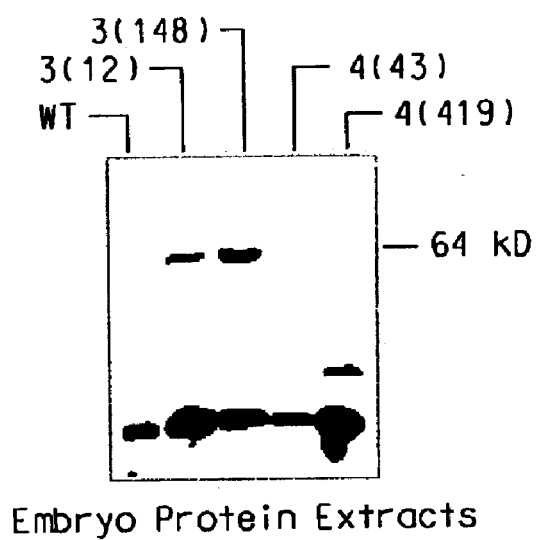
FIG. 13B is an immunoblot showing complete C-terminus of the DP-1B protein.

To overcome the antibody-native protein cross-reactions, the protein extracts of the transgenic and wild-type (control) soy somatic embryonic tissues were partially purified using a Ni-NTA Spin Kit (Qiagen, Valencia, Calif.), prior to immuno-blot assay. Briefly, the protein extract made from 200 mg embryonic tissue was diluted by adding 400 µL lysis buffer and then loaded onto a pre-equilibrated Ni-NTA spin column. DP-1B protein in the extract was bound to the column by a 2 min centrifugation at 700×g, washed twice with 600 µL wash buffer, and finally eluted with 200 µL elution buffer. Twenty µL of the partially purified protein extract was run on a SDS-PAGE and examined by immuno-blot assay. The assay probed with DP-1B Abs confirmed accumulation of 65 kD DP-1B.8P protein in those 7 selected pLS3 transformants of soy somatic embryos. It also confirmed that no 127 kD DP-1B. 16P protein had accumulated to a detectable level in the pLS4 transgenic embryos. The results are shown in FIG. 13A. The immuno-blot assay probed with Anti-His(C-term)-HRP further demonstrated that the all of the accumulated DP-1B.8P consisted of full length molecules since their N-terminal 6×His-tags were recognized (FIG. 13B). Additionally the anti-His (C-term)-HRP also recognized a few smaller protein molecules in the embryo protein extracts, which is shown in the right panel of FIG. 13B. Since these proteins were also detected from the protein extract of wild-type embryo, it is concluded that they must be native embryo proteins rather than the products of the transgenes.

Confirmation of Transgene Insertion into Genomes of Soy Somatic Embryos

Figure 13C:
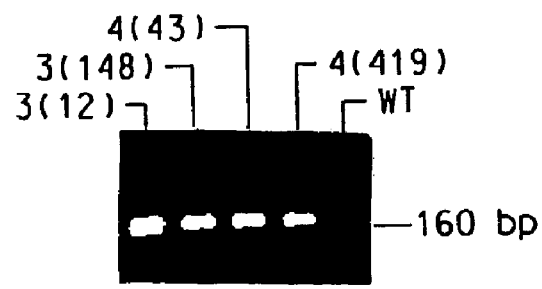
FIG. 13C is a DNA agrose gel showing the transgene in chromosome of soy somatic embryo.

It was expected that most of the soy somatic embryonic colonies surviving hygromycin B selection were transgenic embryos, though many of them did not accumulate DP-1B protein. To further demonstrate that DP-1B.8P and DP-1B.16P transgenes did integrate into chromosome of the embryos, DNA samples were prepared from those embryonic tissues and a control wild-type embryo, using DNeasy Plant Mini Kit (Qiagen, Valencia, Calif.). Preparations used 100 mg embryonic tissue in 100 µL DNA solution by following manufacturer's instruction. DNA concentration and purity of each preparation were estimated by measuring $OD_{260}$ and $OD_{280}$ values in a Beckman DU640 Spectrophotometer. The DNA samples were subjected to PCR reactions, as described earlier. Primer 5' conglycinin-F (5' CCC,GTC, AAA,CTG, CAT,GCC,AC 3') (SEQ ID NO:28) and primer 5' conglycinin-R (5' TAG,CCA,TGG,TTA,GTA, TAT,CTT 3') (SEQ ID NO:29) were used to amplify a 160 bp fragment of the β-conglycinin promoter. The reactions were separated on an agarose gel containing ethidium bromide, and results were visualized under UV light. Results are shown in FIG. 13C. FIG. 13C indicates the expected DNA products and confirmed the integration of DP-1B transgenes.

Example 8

Purification of DP-1B Protein From *Arabidopsis*
Homozygous Plant Selection and Large-scale Growth To obtain large amount of start material, homozygous transgenic plant was selected for direct soil growth. T1 seeds are define as seeds collected from transformed flowers. T1 plant is the plant germinated from T1 seed. T2 seeds are collected from T1 plant. When T2 seeds are germinated, the resulting plants are called T2 plants. At first, T2 seeds were collected from the pGY401 transgenic *Arabidopsis* expressing DP-1B.8P protein in leaf tissue up to 9.2% of total soluble protein, as described in Example 5. Since *Arabidopsis*' self-fertilization nature, heterozygous and homozygous progenies respectively represent 50% and 25% of population among the T2 seed collection. These T2 seeds were germinated as T2 plants on the primary selective medium and twelve of them were grown in Metro Mix soil until maturation in a method described earlier. T3 seeds were harvested from each of twelve plants and germinated on the primary selective media separately. Only homozygous T3 seeds could germinate as T3 plants on the selective medium without showing segregation. Therefore, T4 seeds were collected from those homozygous T3 plants for future use.

For larger scale growth, the T4 homozygous seeds prepared above were germinated and grown on top of Metro Mix soil in 20×10 inch flats, in a density of approximately 1,000 seeds per flat. To ensure larger rosettes, plants were grown in a 22° C. temperature-controlling green house with less than 10 hours natural lighting. The plants were harvested before bolting, treated with liquid nitrogen, and stored in −80° C. DP-1B.8P transgene insertion and protein synthesis in the transgenic plants were confirmed by immunoblot and PCR assays, respectively, as described earlier.

Purification of DP-1B.8P Protein

A DP-1B protein purification protocol was developed. It utilizes SLP's special precipitation properties to separate DP- I B protein from plant native proteins, as described below:

(1) Plant rosettes were homogenized in 5×volume of ice-cold protein extract buffer (50 mM Tris.HCl pH 8.0, 12.5 mM $MgCl_2$, 0.1 mM EDTA, 2 mM DTT, 5% glycerol) using a kitchen blender. Homogenate was filtrated through 6-layers of cheesecloth and then centrifuged at 10,000×g for 10 min at 4° C. Supernatant was kept as protein extract.

(2) The concentrated HCl was slowly added into the stirred protein extract until pH 4.7. The extract was kept in 4° C. for 30 min and then centrifuged at 10,000×g at 4° C. for 30 min to remove protein precipitation. The pH value of the supernatant was adjusted back to 8.0 by slowly adding 10 N NaOH. The resulting solution was saved as pH 4.7 supernatant.

(3) The pH 4.7 supernatant was subjected to heat treatment in a 60° C. waterbath for 60 min and then centrifuged at 10,000×g at 4° C. for 30 min to remove protein precipitation. The supernatant was filtered through one layer of 20 μm nylon mesh and saved. The supernatant were named as "60° C. Supernatant".

(4) (NH$_4$)$_2$SO$_4$ was slowly added and dissolved into the stirred 60° C. Supernatant in an ice-water bath up to 40% saturation. The solution was kept at 4° C. overnight and then centrifuged at 10,000×g at 4° C. for 30 min. The supernatant was named and saved as "(NH$_4$)$_2$SO$_4$ Supernatant". Protein precipitation was resuspended and dialyzed with protein extract buffer, resulted in a DP-1B.8P protein solution in the one fifteenth of original volume.

Figure 14A:
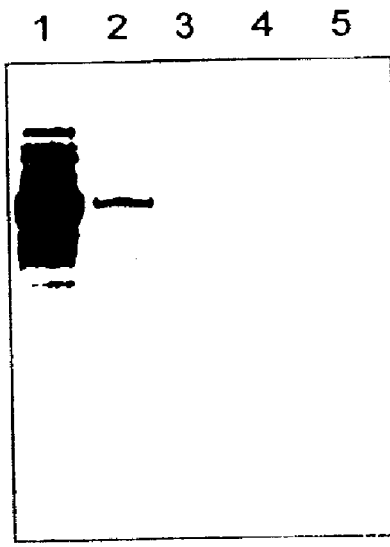
FIG. 14A is a coomassie blue staining of total protein profiles in the purification fractions from *Arabidopsis* plant rosettes used in Example 8.

To examine total protein profiles during the course of purification, protein samples from each step were subjected to SDS-PAGE, which included 20 μL protein extract (FIG. 14A, lane 1), 20 μL pH 4.7 supernatant (FIG. 14A, lane 2), 20 μL 60° C. supernatant (FIG. 14A, lane 3), 10 μL (NH$_4$)$_2$SO$_4$ precipitation resuspension (FIG. 14A, lane 4), and 20 μL (NH$_4$)$_2$SO$_4$ supernatant. The gel was stained with coomassie blue staining solution (0.25% coomassie blue R-250, 20% methanol) overnight and then destained in a solution containing 7% acetic acid and 5% methanol (FIG. 14A).

Due to its unique amino acid composition, DP-1B protein could not be visualized with coomassie blue staining or other conventional staining methods. But FIG. 14A does show that each step in the protocol removes a significant amount of plant native proteins from the extract. In (NH$_4$)$_2$SO$_4$ precipitation fraction (FIG. 14A, lane 4), more than 95% of plant native proteins has been cleaned out.

Figure 14B:
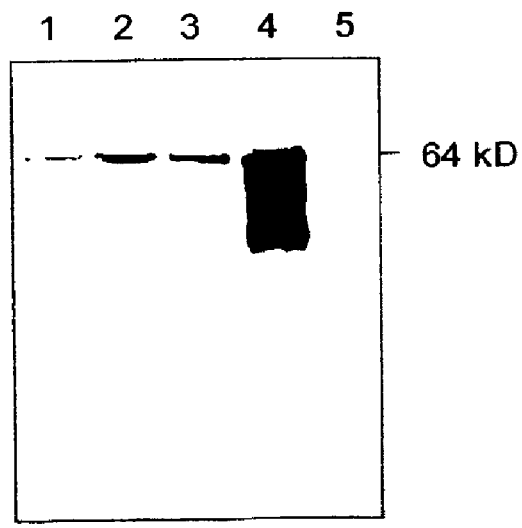
FIG. 14B is an immunoblot detection of DPsensitive and can be spun into semicrystalline fiber. SLP's should also include molecules which are the modified variants of the natural silk proteins and their synthetic analogs defined above.

To monitor DP-1B protein purification, an identical SDS-PAGE was carried out. The gel was transferred to a nitrocellulose membrane and subjected to immunoblot assay in a method described earlier. The DP-1B antibody was used as the primary antibody and the anti-rabbit IgG HRP as the secondary antibody. Result in FIG. 14B shows that the 64 kD DP-1B.8P protein was present in all examined fractions, except (NH$_4$)$_2$SO$_4$ supernatant, during the course of purification. It is extremely enriched in the resuspension of 40% (NH$_4$)$_2$SO$_4$ protein precipitation (FIG. 14B, lane 4). We have also examined pH 6.7 and 60° C. protein precipitation fractions, and no DP-1B.8P protein was detected (data not shown). Thus, DP-1B protein is concentrated into (NH$_4$)$_2$SO$_4$ precipitation fraction.

In conclusion, we have developed a simple DP-1B purification protocol that removes more than 95% of plant native proteins while concentrates DP-1B protein. Due to a 6×histidine tag is attached with C-terminus of DP-1B protein, Ni-column chromatography will possibly further purify the protein to higher purity.

What is claimed is:

1. A plant expressing a silk-like protein (SLP), wherein the plant is transformed with an SLP expression cassette having the following structure:

P-SLP-T wherein:
P is a promoter suitable for driving the expression of a silk-like protein gene;
SLP is a transgene encoding a mature silk-like protein; and T is a 5' terminator;
wherein each of P, SLP and T are operably linked such that expression of the cassette results in translation of the silk-like protein.

2. The plant according to claim 1, wherein the promoter is selected form the group consisting of plant constitutive and plant tissue specific promoters.

3. The plant according to claim 1 wherein the constitutive promoter is selected from the group consisting of CaMV 35S promoter, the nopaline synthase promoter, the octopine synthase promoter, the ribulose-1,5-bisphosphate carboxylase promoter, Adh 1-based pEmu, Act1, SAM synthase promoter, and Ubi promoters and the promoter of the chlorophyll a/b binding protein.

4. The plant method according to claim 1 wherein the tissue specific promoters are those isolated from genes encoding the proteins selected from the group consisting of napin, cruciferin, beta-conglycinin, phaseolin, zein, oleosin, acyl carrier protein, stearoyl-ACP desaturase, fatty acid desaturases, glycinin, Bce4, vicilin, and patatin.

5. The plant according to claim 1 wherein said transgene expresses a silk-like protein derived from silks produced by *Bombyx mori* or *Nephila clavipes*.

6. The plant according to claim 1 wherein the silk-like protein has the general formula:

[ACGQG[GYG]$_b$GLGXQGAGRGGLGGQGAGAnGG]Z (SEQ ID NO: 12)

wherein X=S, G or N; n=0–7, b=0–1, and z=1–75, and wherein the value of z determines the number of repeats in the variant protein and wherein the formula [encompasses] further comprises variations selected from the group consisting of:

(a) when n=0 and z=1, the sequence encompassing AGRGGLGGQGAGAnGG (amino acid residues 15–29 of SEQ ID NO: 12) is deleted;

(b) when n=0 and z=2–75 the sequence encompassing AGRGGLGGQGAGAnGG is deleted creating a first repeat sequence which is preceded by a second repeat sequence wherein n=6;

(c) deletions other than the poly-alanine sequence, will be made in integral multiples of three consecutive residues; and (d) when b=0, GRG is deleted; and wherein the full-length protein is encoded by a gene or genes and wherein said gene or genes are not endogenous to the *Nephila clavipes* genome.

7. The plant of claim 1, wherein the silk-like protein is expressed at levels of about 0.1% to about 9.2%.

8. The plant according to claim 1, wherein the plant is a monocot.

9. The plant according to claim 8 wherein the plant is selected from the group consisting of corn, wheat, barley, oats, sorghum, rice, rye, grasses, and banana.

10. The plant according to claim 1, wherein the plant is a dicot.

11. A method according to claim 10 wherein the plant is selected from the group consisting of soybean, rapeseed, sunflower, cotton, tobacco, alfalfa, *Arabidopsis,* sugar beet, sugar cane, canola, millet, beans, peas, flax, and forage grasses.

* * * * *

SEQUENCE LISTING

```
<160> NUMBER OF SEQ ID NOS: 29
<210> SEQ ID NO 1
<211> LENGTH: 651
<212> TYPE: PRT
<213> ORGANISM: Nephila clavipes

<400> SEQUENCE: 1

Gln Gly Ala Gly Ala Ala Ala Ala Ala Gly Gly Ala Gly Gln Gly
 1               5                  10                  15

Gly Tyr Gly Gly Leu Gly Gly Gln Gly Ala Gly Gln Gly Gly Tyr Gly
                20                  25                  30

Gly Leu Gly Gly Gln Gly Ala Gly Gln Gly Ala Gly Ala Ala Ala Ala
            35                  40                  45

Ala Ala Ala Gly Gly Ala Gly Gln Gly Gly Tyr Gly Gly Leu Gly Ser
        50                  55                  60

Gln Gly Ala Gly Arg Gly Gly Gln Gly Ala Gly Ala Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
            100                 105                 110

Ala Ala Ala Gly Gly Ala Gly Gln Gly Gly Tyr Gly Gly Leu Gly Asn
        115                 120                 125

Gln Gly Ala Gly Arg Gly Gly Gln Gly Ala Ala Ala Ala Ala Ala Gly
    130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala Ala
```

-continued

```
                 165                 170                 175
Gly Gly Ala Gly Gln Gly Gly Tyr Gly Gly Leu Gly Gly Gln Gly Ala
            180                 185                 190
Gly Gln Gly Gly Tyr Gly Gly Leu Gly Ser Gln Gly Ala Gly Arg Gly
            195                 200                 205
Gly Leu Gly Gly Gln Gly Ala Gly Ala Ala Ala Ala Ala Ala Ala Gly
            210                 215                 220
Gly Ala Gly Gln Gly Gly Leu Gly Gly Gln Gly Ala Gly Gln Gly Ala
225                 230                 235                 240
Gly Ala Ser Ala Ala Ala Gly Gly Ala Gly Gln Gly Gly Tyr Gly
            245                 250                 255
Gly Leu Gly Ser Gln Gly Ala Gly Arg Gly Gly Glu Gly Ala Gly Ala
            260                 265                 270
Ala Ala Ala Ala Gly Gly Ala Gly Gln Gly Gly Tyr Gly Gly Leu
            275                 280                 285
Gly Gly Gln Gly Ala Gly Gln Gly Gly Tyr Gly Gly Leu Gly Ser Gln
            290                 295                 300
Gly Ala Gly Arg Gly Gly Leu Gly Gly Gln Gly Ala Gly Ala Ala Ala
305                 310                 315                 320
Ala Gly Gly Ala Gly Gln Gly Gly Leu Gly Gly Gln Gly Ala Gly Gln
            325                 330                 335
Gly Ala Gly Ala Ala Ala Ala Ala Gly Gly Ala Gly Gln Gly Gly
            340                 345                 350
Tyr Gly Gly Leu Gly Ser Gln Gly Ala Gly Arg Gly Gly Leu Gly Gly
            355                 360                 365
Gln Gly Ala Gly Ala Val Ala Ala Ala Ala Gly Gly Ala Gly Gln
            370                 375                 380
Gly Gly Tyr Gly Gly Leu Gly Ser Gln Gly Ala Gly Arg Gly Gly Gln
385                 390                 395                 400
Gly Ala Gly Ala Ala Ala Ala Ala Gly Ala Gly Gln Arg Gly
            405                 410                 415
Tyr Gly Gly Leu Gly Asn Gln Gly Ala Gly Arg Gly Gly Leu Gly Gly
            420                 425                 430
Gln Gly Ala Gly Ala Ala Ala Ala Ala Ala Gly Gly Ala Gly Gln
            435                 440                 445
Gly Gly Tyr Gly Gly Leu Gly Asn Gln Gly Ala Gly Arg Gly Gly Gln
            450                 455                 460
Gly Ala Ala Ala Ala Ala Gly Gly Ala Gly Gln Gly Gly Tyr Gly Gly
465                 470                 475                 480
Leu Gly Ser Gln Gly Ala Gly Arg Gly Gly Gln Gly Ala Gly Ala Ala
            485                 490                 495
Ala Ala Ala Val Gly Ala Gly Gln Glu Gly Ile Arg Gly Gln Gly
            500                 505                 510
Ala Gly Gln Gly Gly Tyr Gly Gly Leu Gly Ser Gln Gly Ser Gly Arg
            515                 520                 525
Gly Gly Leu Gly Gly Gln Gly Ala Gly Ala Ala Ala Ala Ala Gly
            530                 535                 540
Gly Ala Gly Gln Gly Gly Leu Gly Gly Gln Gly Ala Gly Gln Gly Ala
545                 550                 555                 560
Gly Ala Ala Ala Ala Ala Gly Gly Val Arg Gln Gly Gly Tyr Gly
            565                 570                 575
Gly Leu Gly Ser Gln Gly Ala Gly Arg Gly Gly Gln Gly Ala Gly Ala
            580                 585                 590
```

```
Ala Ala Ala Ala Ala Gly Gly Ala Gly Gln Gly Gly Tyr Gly Gly Leu
         595                 600                 605

Gly Gly Gln Gly Val Gly Arg Gly Gly Leu Gly Gly Gln Gly Ala Gly
    610                 615                 620

Ala Ala Ala Ala Gly Gly Ala Gly Gln Gly Gly Tyr Gly Gly Val Gly
625                 630                 635                 640

Ser Gly Ala Ser Ala Ala Ser Ala Ala Ala Ala
                645                 650

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:  SLP repeat

<400> SEQUENCE: 2

Ser Gly Ala Gly Ala Gly
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:  SLP repeat

<400> SEQUENCE: 3

Gly Ala Gly Ala Gly Ser
  1               5

<210> SEQ ID NO 4
<211> LENGTH: 59
<212> TYPE: PRT
<213> ORGANISM: Artificial Sequence
<220> FEATURE:
<223> OTHER INFORMATION: Description of Artificial Sequence:  SLP repeat

<400> SEQUENCE: 4

Gly Ala Gly Ala Gly Ser Gly Ala Gly Ala Gly Ser Gly Ala Gly Ala
  1               5                  10                  15

Gly Ser Gly Ala Gly Ala Gly Ser Gly Ala Gly Ala Gly Ser Gly Ala
                 20                  25                  30

Gly Ala Gly Ser Gly Ala Gly Ala Gly Ser Gly Ala Gly Ala Gly Ser
         35                  40                  45

Gly Ala Gly Ala Gly Ser Gly Ala Ala Gly Tyr
     50                  55

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  SLP repeat

<400> SEQUENCE: 5

Ser Gly Gly Ala Gly Gly Ala Gly Gly
  1               5

<210> SEQ ID NO 6
<211> LENGTH: 10
<212> TYPE: PRT
<213> ORGANISM: Artificial Sequence
```

```
<220> FEATURE:
<223> OTHER INFORMATION: Description of Artificial Sequence:  SLP repeat

<400> SEQUENCE: 6

Gly Pro Gly Gln Gln Gly Pro Gly Gly Tyr
 1               5                  10

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:  SLP repeat

<400> SEQUENCE: 7

Gly Ala Gly Ala Gly Tyr
 1               5

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence:  SLP repeat
<220> FEATURE:
<221> NAME/KEY: UNSURE
<222> LOCATION: (11)
<223> OTHER INFORMATION: X=S, G OR N

<400> SEQUENCE: 8

Ala Gly Gln Gly Gly Tyr Gly Gly Leu Gly Xaa Gln Gly Ala Gly Arg
 1               5                  10                  15

Gly Gly Leu Gly Gly Gln Gly Ala Gly Ala Ala Ala Ala Ala Ala
                20                  25                  30

Gly Gly

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence:  SLP repeat

<400> SEQUENCE: 9

Ala Gly Arg Gly Gly Leu Gly Gly Gln Gly Ala Gly Ala Gly Gly
 1               5                  10                  15

<210> SEQ ID NO 10
<211> LENGTH: 101
<212> TYPE: PRT
<213> ORGANISM: Artificial Sequence
<220> FEATURE:
<223> OTHER INFORMATION: Description of Artificial Sequence:  DP-1A
      monomer

<400> SEQUENCE: 10

Gly Ala Gly Arg Gly Gly Gln Gly Ala Gly Ala Ala Ala Ala Ala
 1               5                  10                  15

Gly Gly Ala Gly Gln Gly Gly Tyr Gly Gly Leu Gly Ser Gln Gly Ala
                20                  25                  30

Gly Arg Gly Gly Leu Gly Gly Gln Gly Ala Gly Ala Ala Ala Ala
           35                  40                  45

Ala Ala Gly Gly Ala Gly Gln Gly Gly Leu Gly Ser Gln Gly Ala Gly
     50                  55                  60
```

-continued

```
Gln Gly Ala Gly Ala Ala Ala Ala Gly Gly Ala Gln Gly
 65                  70                  75                  80

Gly Tyr Gly Gly Leu Gly Ser Gln Ala Gly Gln Gly Tyr Gly
                 85                  90                  95

Gly Leu Gly Ser Gln
            100

<210> SEQ ID NO 11
<211> LENGTH: 101
<212> TYPE: PRT
<213> ORGANISM: Artificial Sequence
<220> FEATURE:
<223> OTHER INFORMATION: Description of Artificial Sequence:  DP-1B
      monomer

<400> SEQUENCE: 11

Gly Ala Gly Gln Gly Gly Tyr Gly Gly Leu Gly Ser Gln Gly Ala Gly
  1               5                  10                  15

Arg Gly Gly Leu Gly Gly Gln Gly Ala Gly Ala Ala Ala Ala Ala
                 20                  25                  30

Ala Gly Gly Ala Gly Gln Gly Gly Leu Gly Ser Gln Gly Ala Gly Gln
             35                  40                  45

Gly Ala Gly Ala Ala Ala Ala Ala Gly Gly Ala Gly Gln Gly Gly
         50                  55                  60

Tyr Gly Gly Leu Gly Ser Gln Gly Ala Gly Arg Gly Gly Leu Gly Ala
 65                  70                  75                  80

Gly Ala Ala Ala Ala Ala Gly Gly Ala Gly Gln Gly Gly Tyr Gly
                 85                  90                  95

Gly Leu Gly Ser Gln
            100

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence:  DP-1B 8mer
<220> FEATURE:
<221> NAME/KEY: UNSURE
<222> LOCATION: (12)
<223> OTHER INFORMATION: X=S,G OR N

<400> SEQUENCE: 12

Ala Cys Gly Gln Gly Gly Tyr Gly Gly Leu Gly Xaa Gln Gly Ala Gly
  1               5                  10                  15

Arg Gly Gly Leu Gly Gly Gln Gly Ala Gly Ala Gly Gly
                 20                  25

<210> SEQ ID NO 13
<211> LENGTH: 809
<212> TYPE: PRT
<213> ORGANISM: Artificial Sequence
<220> FEATURE:
<223> OTHER INFORMATION: Description of Artificial Sequence:  DP-1B
      16mer

<400> SEQUENCE: 13

Arg Ser Gln Gly Ala Gly Gln Gly Gly Tyr Gly Gly Leu Gly Ser Gln
  1               5                  10                  15

Gly Ala Gly Arg Gly Gly Leu Gly Gly Gln Gly Ala Gly Ala Ala Ala
                 20                  25                  30

Ala Ala Ala Ala Gly Gly Ala Gly Gln Gly Gly Leu Gly Ser Gln Gly
```

-continued

```
                35                  40                  45
Ala Gly Gln Gly Ala Gly Ala Ala Ala Ala Gly Gly Ala Gly
         50                  55                  60
Gln Gly Gly Tyr Gly Gly Leu Gly Ser Gln Gly Ala Gly Arg Gly Gly
 65                  70                  75                  80
Gln Gly Ala Gly Ala Ala Ala Ala Gly Gly Ala Gly Gln Gly
         85                  90                  95
Gly Tyr Gly Gly Leu Gly Ser Gln Gly Ala Gly Gln Gly Gly Tyr Gly
             100                 105                 110
Gly Leu Gly Ser Gln Gly Ala Gly Arg Gly Gly Leu Gly Gly Gln Gly
         115                 120                 125
Ala Gly Ala Ala Ala Ala Ala Ala Gly Gly Ala Gly Gln Gly Gly
         130                 135                 140
Leu Gly Ser Gln Gly Ala Gly Gln Gly Ala Gly Ala Ala Ala Ala
145                 150                 155                 160
Ala Gly Gly Ala Gly Gln Gly Gly Tyr Gly Gly Leu Gly Ser Gln Gly
             165                 170                 175
Ala Gly Arg Gly Gly Gln Gly Ala Gly Ala Ala Ala Ala Ala Gly
         180                 185                 190
Gly Ala Gly Gln Gly Gly Tyr Gly Gly Leu Gly Ser Gln Gly Ala Gly
         195                 200                 205
Gln Gly Gly Tyr Gly Gly Leu Gly Ser Gln Gly Ala Gly Arg Gly Gly
 210                 215                 220
Leu Gly Gly Gln Gly Ala Gly Ala Ala Ala Ala Ala Ala Gly Gly
225                 230                 235                 240
Ala Gly Gln Gly Gly Leu Gly Ser Gln Gly Ala Gly Gln Gly Ala Gly
             245                 250                 255
Ala Ala Ala Ala Ala Ala Gly Gly Ala Gly Gln Gly Gly Tyr Gly
         260                 265                 270
Leu Gly Ser Gln Gly Ala Gly Arg Gly Gly Gln Gly Ala Gly Ala Ala
         275                 280                 285
Ala Ala Ala Ala Gly Gly Ala Gly Gln Gly Gly Tyr Gly Gly Leu Gly
 290                 295                 300
Ser Gln Gly Ala Gly Gln Gly Gly Tyr Gly Gly Leu Gly Ser Gln Gly
305                 310                 315                 320
Ala Gly Arg Gly Gly Leu Gly Gly Gln Gly Ala Gly Ala Ala Ala Ala
             325                 330                 335
Ala Ala Ala Gly Gly Ala Gly Gln Gly Gly Leu Gly Ser Gln Gly Ala
         340                 345                 350
Gly Gln Gly Ala Gly Ala Ala Ala Ala Gly Gly Ala Gly Gln
         355                 360                 365
Gly Gly Tyr Gly Gly Leu Gly Ser Gln Gly Ala Gly Arg Gly Gly Gln
 370                 375                 380
Gly Ala Gly Ala Ala Ala Ala Ala Gly Gly Ala Gly Gln Gly Gly
385                 390                 395                 400
Tyr Gly Gly Leu Gly Ser Gln Gly Ala Gly Gln Gly Gly Tyr Gly Gly
             405                 410                 415
Leu Gly Ser Gln Gly Ala Gly Arg Gly Gly Leu Gly Gly Gln Gly Ala
         420                 425                 430
Gly Ala Ala Ala Ala Ala Ala Ala Gly Gly Ala Gly Gln Gly Gly Leu
         435                 440                 445
Gly Ser Gln Gly Ala Gly Gln Gly Ala Gly Ala Ala Ala Ala Ala
         450                 455                 460
```

-continued

```
Gly Gly Ala Gly Gln Gly Gly Tyr Gly Gly Leu Gly Ser Gln Gly Ala
465                 470                 475                 480
Gly Arg Gly Gly Gln Gly Ala Gly Ala Ala Ala Ala Ala Gly Gly
            485                 490                 495
Ala Gly Gln Gly Gly Tyr Gly Gly Leu Gly Ser Gln Gly Ala Gly Gln
        500                 505                 510
Gly Gly Tyr Gly Gly Leu Gly Ser Gln Gly Ala Gly Arg Gly Gly Leu
        515                 520                 525
Gly Gly Gln Gly Ala Gly Ala Ala Ala Ala Ala Ala Gly Gly Ala
        530                 535                 540
Gly Gln Gly Gly Leu Gly Ser Gln Gly Ala Gly Gln Gly Ala Gly Ala
545                 550                 555                 560
Ala Ala Ala Ala Gly Gly Ala Gly Gln Gly Gly Tyr Gly Gly Leu
            565                 570                 575
Gly Ser Gln Gly Ala Gly Arg Gly Gly Gln Gly Ala Gly Ala Ala Ala
            580                 585                 590
Ala Ala Ala Gly Gly Ala Gly Gln Gly Gly Tyr Gly Gly Leu Gly Ser
            595                 600                 605
Gln Gly Ala Gly Gln Gly Gly Tyr Gly Gly Leu Gly Ser Gln Gly Ala
        610                 615                 620
Gly Arg Gly Gly Leu Gly Gly Gln Gly Ala Gly Ala Ala Ala Ala Ala
625                 630                 635                 640
Ala Ala Gly Gly Ala Gly Gln Gly Gly Leu Gly Ser Gln Gly Ala Gly
            645                 650                 655
Gln Gly Ala Gly Ala Ala Ala Ala Ala Gly Gly Ala Gly Gln Gly
            660                 665                 670
Gly Tyr Gly Gly Leu Gly Ser Gln Gly Ala Gly Arg Gly Gly Gln Gly
        675                 680                 685
Ala Gly Ala Ala Ala Ala Ala Gly Gly Ala Gly Gln Gly Gly Tyr
        690                 695                 700
Gly Gly Leu Gly Ser Gln Gly Ala Gly Gln Gly Gly Tyr Gly Gly Leu
705                 710                 715                 720
Gly Ser Gln Gly Ala Gly Arg Gly Gly Leu Gly Gln Gly Ala Gly
            725                 730                 735
Ala Ala Ala Ala Ala Ala Gly Gly Ala Gly Gln Gly Gly Leu Gly
            740                 745                 750
Ser Gln Gly Ala Gly Gln Gly Ala Gly Ala Ala Ala Ala Ala Gly
            755                 760                 765
Gly Ala Gly Gln Gly Gly Tyr Gly Gly Leu Gly Ser Gln Gly Ala Gly
        770                 775                 780
Arg Gly Gly Gln Gly Ala Gly Ala Ala Ala Ala Ala Gly Gly Ala
785                 790                 795                 800
Gly Gln Gly Gly Tyr Gly Gly Leu Gly
            805
```

<210> SEQ ID NO 14
<211> LENGTH: 1617
<212> TYPE: PRT
<213> ORGANISM: Artificial Sequence
<220> FEATURE:
<223> OTHER INFORMATION: Description of Artificial Sequence: Primer

<400> SEQUENCE: 14

```
Arg Ser Gln Gly Ala Gly Gln Gly Gly Tyr Gly Gly Leu Gly Ser Gln
1               5                   10                  15
```

```
Gly Ala Gly Arg Gly Gly Leu Gly Gly Gln Gly Ala Gly Ala Ala Ala
            20                  25                  30

Ala Ala Ala Ala Gly Gly Ala Gly Gln Gly Gly Leu Gly Ser Gln Gly
        35                  40                  45

Ala Gly Gln Gly Ala Gly Ala Ala Ala Ala Ala Gly Gly Ala Gly
    50                  55                  60

Gln Gly Gly Tyr Gly Gly Leu Gly Ser Gln Gly Ala Gly Arg Gly Gly
65                  70                  75                  80

Gln Gly Ala Gly Ala Ala Ala Ala Ala Gly Gly Ala Gly Gln Gly
            85                  90                  95

Gly Tyr Gly Gly Leu Gly Ser Gln Gly Ala Gly Gln Gly Gly Tyr Gly
                100                 105                 110

Gly Leu Gly Ser Gln Gly Ala Gly Arg Gly Gly Leu Gly Gly Gln Gly
            115                 120                 125

Ala Gly Ala Ala Ala Ala Ala Ala Gly Gly Ala Gly Gln Gly Gly
    130                 135                 140

Leu Gly Ser Gln Gly Ala Gly Gln Gly Ala Gly Ala Ala Ala Ala Ala
145                 150                 155                 160

Ala Gly Ala Gly Gln Gly Gly Tyr Gly Gly Leu Gly Ser Gln Gly
            165                 170                 175

Ala Gly Arg Gly Gly Gln Gly Ala Gly Ala Ala Ala Ala Ala Gly
        180                 185                 190

Gly Ala Gly Gln Gly Gly Tyr Gly Gly Leu Gly Ser Gln Gly Ala Gly
            195                 200                 205

Gln Gly Gly Tyr Gly Gly Leu Gly Ser Gln Gly Ala Gly Arg Gly Gly
    210                 215                 220

Leu Gly Gly Gln Gly Ala Gly Ala Ala Ala Ala Ala Ala Gly Gly
225                 230                 235                 240

Ala Gly Gln Gly Gly Leu Gly Ser Gln Gly Ala Gly Gln Gly Ala Gly
            245                 250                 255

Ala Ala Ala Ala Ala Ala Gly Gly Ala Gly Gln Gly Gly Tyr Gly Gly
        260                 265                 270

Leu Gly Ser Gln Gly Ala Gly Arg Gly Gly Gln Gly Ala Gly Ala Ala
    275                 280                 285

Ala Ala Ala Ala Gly Gly Ala Gly Gln Gly Gly Tyr Gly Gly Leu Gly
        290                 295                 300

Ser Gln Gly Ala Gly Gln Gly Gly Tyr Gly Gly Leu Gly Ser Gln Gly
305                 310                 315                 320

Ala Gly Arg Gly Gly Leu Gly Gly Gln Gly Ala Gly Ala Ala Ala Ala
            325                 330                 335

Ala Ala Ala Gly Gly Ala Gly Gln Gly Gly Leu Gly Ser Gln Gly Ala
        340                 345                 350

Gly Gln Gly Ala Gly Ala Ala Ala Ala Ala Gly Gly Ala Gly Gln
    355                 360                 365

Gly Gly Tyr Gly Gly Leu Gly Ser Gln Gly Ala Gly Arg Gly Gly Gln
    370                 375                 380

Gly Ala Gly Ala Ala Ala Ala Ala Gly Gly Ala Gly Gln Gly Gly
385                 390                 395                 400

Tyr Gly Gly Leu Gly Ser Gln Gly Ala Gly Gln Gly Gly Tyr Gly Gly
                405                 410                 415

Leu Gly Ser Gln Gly Ala Gly Arg Gly Gly Leu Gly Gly Gln Gly Ala
            420                 425                 430
```

-continued

```
Gly Ala Ala Ala Ala Ala Ala Gly Gly Ala Gly Gln Gly Gly Leu
            435                 440                 445
Gly Ser Gln Gly Ala Gly Gln Gly Ala Gly Ala Ala Ala Ala Ala
            450                 455                 460
Gly Gly Ala Gly Gln Gly Gly Tyr Gly Gly Leu Gly Ser Gln Gly Ala
465                 470                 475                 480
Gly Arg Gly Gly Gln Gly Ala Gly Ala Ala Ala Ala Ala Gly Gly
            485                 490                 495
Ala Gly Gln Gly Gly Tyr Gly Gly Leu Gly Ser Gln Gly Ala Gly Gln
            500                 505                 510
Gly Gly Tyr Gly Gly Leu Gly Ser Gln Gly Ala Gly Arg Gly Gly Leu
            515                 520                 525
Gly Gly Gln Gly Ala Gly Ala Ala Ala Ala Ala Ala Gly Gly Ala
            530                 535                 540
Gly Gln Gly Gly Leu Gly Ser Gln Gly Ala Gly Gln Gly Ala Gly Ala
545                 550                 555                 560
Ala Ala Ala Ala Gly Gly Ala Gly Gln Gly Gly Tyr Gly Gly Leu
            565                 570                 575
Gly Ser Gln Gly Ala Gly Arg Gly Gly Gln Gly Ala Gly Ala Ala Ala
            580                 585                 590
Ala Ala Ala Gly Gly Ala Gly Gln Gly Gly Tyr Gly Gly Leu Gly Ser
            595                 600                 605
Gln Gly Ala Gly Gln Gly Gly Tyr Gly Gly Leu Gly Ser Gln Gly Ala
            610                 615                 620
Gly Arg Gly Gly Leu Gly Gly Gln Gly Ala Gly Ala Ala Ala Ala Ala
625                 630                 635                 640
Ala Ala Gly Gly Ala Gly Gln Gly Gly Leu Gly Ser Gln Gly Ala Gly
            645                 650                 655
Gln Gly Ala Gly Ala Ala Ala Ala Ala Gly Gly Ala Gly Gln Gly
            660                 665                 670
Gly Tyr Gly Gly Leu Gly Ser Gln Gly Ala Gly Arg Gly Gly Gln Gly
            675                 680                 685
Ala Gly Ala Ala Ala Ala Ala Gly Gly Ala Gly Gln Gly Gly Tyr
            690                 695                 700
Gly Gly Leu Gly Ser Gln Gly Ala Gly Gln Gly Gly Tyr Gly Gly Leu
705                 710                 715                 720
Gly Ser Gln Gly Ala Gly Arg Gly Gly Leu Gly Gly Gln Gly Ala Gly
            725                 730                 735
Ala Ala Ala Ala Ala Ala Gly Gly Ala Gly Gln Gly Gly Leu Gly
            740                 745                 750
Ser Gln Gly Ala Gly Gln Gly Ala Gly Ala Ala Ala Ala Ala Gly
            755                 760                 765
Gly Ala Gly Gln Gly Gly Tyr Gly Gly Leu Gly Ser Gln Gly Ala Gly
            770                 775                 780
Arg Gly Gly Gln Gly Ala Gly Ala Ala Ala Ala Ala Gly Gly Ala
785                 790                 795                 800
Gly Gln Gly Gly Tyr Gly Gly Leu Gly Ser Gln Gly Ala Gly Gln Gly
            805                 810                 815
Gly Tyr Gly Gly Leu Gly Ser Gln Gly Ala Gly Arg Gly Gly Leu Gly
            820                 825                 830
Gly Gln Gly Ala Gly Ala Ala Ala Ala Ala Ala Gly Gly Ala Gly
            835                 840                 845
Gln Gly Gly Leu Gly Ser Gln Gly Ala Gly Gln Gly Ala Gly Ala Ala
```

-continued

```
            850                 855                 860
Ala Ala Ala Ala Gly Gly Ala Gly Gln Gly Gly Tyr Gly Gly Leu Gly
865                 870                 875                 880

Ser Gln Gly Ala Gly Arg Gly Gly Gln Gly Ala Gly Ala Ala Ala Ala
                885                 890                 895

Ala Ala Gly Gly Ala Gly Gln Gly Gly Tyr Gly Gly Leu Gly Ser Gln
            900                 905                 910

Gly Ala Gly Gln Gly Gly Tyr Gly Gly Leu Gly Ser Gln Gly Ala Gly
            915                 920                 925

Arg Gly Gly Leu Gly Gly Gln Gly Ala Gly Ala Ala Ala Ala Ala
    930                 935                 940

Ala Gly Gly Ala Gly Gln Gly Gly Leu Gly Ser Gln Gly Ala Gly Gln
945                 950                 955                 960

Gly Ala Gly Ala Ala Ala Ala Ala Gly Gly Ala Gly Gln Gly Gly
                965                 970                 975

Tyr Gly Gly Leu Gly Ser Gln Gly Ala Gly Arg Gly Gly Gln Gly Ala
            980                 985                 990

Gly Ala Ala Ala Ala Ala Ala Gly Gly Ala Gly Gln Gly Gly Tyr Gly
            995                 1000                1005

Gly Leu Gly Ser Gln Gly Ala Gly Gln Gly Gly Tyr Gly Gly Leu Gly
    1010                1015                1020

Ser Gln Gly Ala Gly Arg Gly Gly Leu Gly Gly Gln Gly Ala Gly Ala
1025                1030                1035                1040

Ala Ala Ala Ala Ala Ala Gly Gly Ala Gly Gln Gly Gly Leu Gly Ser
                1045                1050                1055

Gln Gly Ala Gly Gln Gly Ala Gly Ala Ala Ala Ala Ala Gly Gly
            1060                1065                1070

Ala Gly Gln Gly Gly Tyr Gly Gly Leu Gly Ser Gln Gly Ala Gly Arg
            1075                1080                1085

Gly Gly Gln Gly Ala Gly Ala Ala Ala Ala Ala Gly Gly Ala Gly
    1090                1095                1100

Gln Gly Gly Tyr Gly Gly Leu Gly Ser Gln Gly Ala Gly Gln Gly Gly
1105                1110                1115                1120

Tyr Gly Gly Leu Gly Ser Gln Gly Ala Gly Arg Gly Gly Leu Gly Gly
            1125                1130                1135

Gln Gly Ala Gly Ala Ala Ala Ala Ala Ala Gly Gly Ala Gly Gln
            1140                1145                1150

Gly Gly Leu Gly Ser Gln Gly Ala Gly Gln Gly Ala Gly Ala Ala Ala
    1155                1160                1165

Ala Ala Ala Gly Gly Ala Gly Gln Gly Gly Tyr Gly Gly Leu Gly Ser
    1170                1175                1180

Gln Gly Ala Gly Arg Gly Gly Gln Gly Ala Gly Ala Ala Ala Ala
1185                1190                1195                1200

Ala Gly Gly Ala Gly Gln Gly Gly Tyr Gly Gly Leu Gly Ser Gln Gly
            1205                1210                1215

Ala Gly Gln Gly Gly Tyr Gly Gly Leu Gly Ser Gln Gly Ala Gly Arg
            1220                1225                1230

Gly Gly Leu Gly Gly Gln Gly Ala Gly Ala Ala Ala Ala Ala Ala
        1235                1240                1245

Gly Gly Ala Gly Gln Gly Gly Leu Gly Ser Gln Gly Ala Gly Gln Gly
    1250                1255                1260

Ala Gly Ala Ala Ala Ala Ala Ala Gly Gly Ala Gly Gln Gly Gly Tyr
1265                1270                1275                1280
```

Gly Gly Leu Gly Ser Gln Gly Ala Gly Arg Gly Gly Gln Gly Ala Gly
            1285                1290                1295

Ala Ala Ala Ala Ala Ala Gly Gly Ala Gly Gln Gly Gly Tyr Gly Gly
        1300                1305                1310

Leu Gly Ser Gln Gly Ala Gly Gln Gly Gly Tyr Gly Gly Leu Gly Ser
        1315                1320                1325

Gln Gly Ala Gly Arg Gly Gly Leu Gly Gly Gln Gly Ala Gly Ala Ala
        1330                1335                1340

Ala Ala Ala Ala Ala Gly Gly Ala Gly Gln Gly Gly Leu Gly Ser Gln
1345                1350                1355                1360

Gly Ala Gly Gln Gly Ala Gly Ala Ala Ala Ala Ala Ala Gly Gly Ala
            1365                1370                1375

Gly Gln Gly Gly Tyr Gly Gly Leu Gly Ser Gln Gly Ala Gly Arg Gly
            1380                1385                1390

Gly Gln Gly Ala Gly Ala Ala Ala Ala Ala Gly Gly Ala Gly Gln
            1395                1400                1405

Gly Gly Tyr Gly Gly Leu Gly Ser Gln Gly Ala Gly Gln Gly Gly Tyr
        1410                1415                1420

Gly Gly Leu Gly Ser Gln Gly Ala Gly Arg Gly Gly Leu Gly Gly Gln
1425                1430                1435                1440

Gly Ala Gly Ala Ala Ala Ala Ala Ala Gly Gly Ala Gly Gln Gly
            1445                1450                1455

Gly Leu Gly Ser Gln Gly Ala Gly Gln Gly Ala Gly Ala Ala Ala Ala
        1460                1465                1470

Ala Ala Gly Gly Ala Gly Gln Gly Gly Tyr Gly Gly Leu Gly Ser Gln
        1475                1480                1485

Gly Ala Gly Arg Gly Gly Gln Gly Ala Gly Ala Ala Ala Ala Ala
        1490                1495                1500

Gly Gly Ala Gly Gln Gly Gly Tyr Gly Gly Leu Gly Ser Gln Gly Ala
1505                1510                1515                1520

Gly Gln Gly Gly Tyr Gly Gly Leu Gly Ser Gln Gly Ala Gly Arg Gly
            1525                1530                1535

Gly Leu Gly Gly Gln Gly Ala Gly Ala Ala Ala Ala Ala Ala Gly
            1540                1545                1550

Gly Ala Gly Gln Gly Gly Leu Gly Ser Gln Gly Ala Gly Gln Gly Ala
            1555                1560                1565

Gly Ala Ala Ala Ala Ala Ala Gly Gly Ala Gly Gln Gly Gly Tyr Gly
        1570                1575                1580

Gly Leu Gly Ser Gln Gly Ala Gly Arg Gly Gly Gln Gly Ala Gly Ala
1585                1590                1595                1600

Ala Ala Ala Ala Gly Gly Ala Gly Gln Gly Gly Tyr Gly Gly Leu
            1605                1610                1615

Gly

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 15
gatctccatg gctagatcta gaggatccca tcaccatcac catcactaag        50

```
<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 16
aattcttagt gatggtgatg gtgatgggat cctctagatc tagccatgga        50

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: SPL repeat

<400> SEQUENCE: 17

Ala Arg Ser Arg Gly Ser
 1               5

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 18
gatctccatg gctagatcta gaggatccca tcaccatcac catcactaag        50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 19
aggtaccgat ctagatctcc tagggtagtg gtagtggtag tgattcttaa        50

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Adapter
      peptide

<400> SEQUENCE: 20

Met Ala Arg Ser Arg Gly Ser His His His His His His
 1               5                  10

<210> SEQ ID NO 21
<211> LENGTH: 2457
<212> TYPE: DNA
<213> ORGANISM: Artificial Sequence
<220> FEATURE:
<223> OTHER INFORMATION: Description of Artificial Sequence: DP-1B
      8mer coding region with His tab

<400> SEQUENCE: 21
atggctagat ctcaaggagc cggtcaaggt ggttacggag gtctgggatc tcaaggtgct        60
ggacgtggtg gtcttggtgg tcagggtgcc ggtgccgccg ctgccgccgc cgctggtggt       120
```

```
gctggacaag gtggtttggg atctcaggga gctggtcaag gtgccggtgc tgctgccgct      180
gctgccggag gtgccggtca gggtggatac ggtggacttg gatctcaggg tgctggtaga      240
ggtggacaag gtgccggagc tgccgctgcc gctgccggtg gtgctggtca aggaggttac      300
ggtggtcttg gatctcaagg agccggtcaa ggtggttacg gaggtctggg atctcaaggt      360
gctggacgtg gtggtcttgg tggtcagggt gccggtgccg ccgctgccgc cgccgctggt      420
ggtgctggac aaggtggttt gggatctcag ggagctggtc aaggtgccgg tgctgctgcc      480
gctgctgccg gaggtgccgg tcaggtggga tacggtggac ttggatctca gggtgctggt      540
agaggtggac aaggtgccgg agctgccgct gccgctgccg gtggtgctgg tcaaggaggt      600
tacggtggtc ttggatctca aggagccggt caaggtggtt acggaggtct gggatctcaa      660
ggtgctggac gtggtggtct tggtggtcag ggtgccggtg ccgccgctgc cgccgccgct      720
ggtggtgctg gacaaggtgg tttgggatct cagggagctg gtcaaggtgc cggtgctgct      780
gccgctgctg ccgaggtgcc ggtcaggtgg gatacggtg gacttggatc tcaggtgct      840 ggtagaggtg gacaaggtgc cggagctgcc gctgccgctg ccggtggtgc tggtcaagga      900
ggttacggtg gtcttggatc tcaaggagcc ggtcaaggtg gttacggagg tctgggatct      960
caaggtgctg gacgtggtgg tcttggtggt cagggtgccg gtgccgccgc tgccgccgcc     1020
gctggtggtg ctggacaagg tggtttggga tctcagggag ctggtcaagg tgccggtgct     1080
gctgccgctg ctgccggagg tgccggtcag gtggatacg gtggacttgg atctcaggt     1140 gctggtagag gtggacaagg tgccggagct gccgctgccg ctgccggtgg tgctggtcaa     1200
ggaggttacg gtggtcttgg atctcaagga gccggtcaag gtggttacgg aggtctggga     1260
tctcaaggtg ctggacgtgg tggtcttggt ggtcagggtg ccggtgccgc cgctgccgcc     1320
gccgctggtg gtgctggaca aggtggtttg gatctcagg gagctggtca aggtgccggt     1380
gctgctgccg ctgctgccgg aggtgccggt caggtggat acggtggact tggatctcag     1440
ggtgctggta gaggtggaca aggtgccgga gctgccgctg ccgctgccgg tggtgctggt     1500
caaggaggtt acggtggtct tggatctcaa ggagccggtc aaggtggtta cggaggtctg     1560
ggatctcaag gtgctggacg tggtggtctt ggtggtcagg gtgccggtgc cgccgctgcc     1620
gccgccgctg gtgtgctgg acaaggtggt ttgggatctc agggagctgg tcaaggtgcc     1680
ggtgctgctc ccgctgctgc cggaggtgcc ggtcaggtg gatacggtgg acttggatct     1740
cagggtgctg gtagaggtgg acaaggtgcc ggagctgccg ctgccgctgc cggtggtgct     1800
ggtcaaggag gttacggtgg tcttggatct caaggagccg tcaaggtgg ttacggaggt     1860 ctgggatctc aaggtgctgg acgtggtggt cttggtggtc aggtgccgg tgccgccgct     1920 gccgccgccg ctggtggtgc tggacaaggt ggtttgggat ctcagggagc tggtcaaggt     1980
gccggtgctg ctgccgctgc tgccggaggt gccggtcagg tggatacgg tggacttgga     2040 tctcagggtg ctggtagagg tggacaaggt gccggagctg ccgctgccgc tgccggtggt     2100
gctggtcaag gaggttacgg tggtcttgga tctcaaggag ccggtcaagg tggttacgga     2160
ggtctgggat ctcaaggtgc tggacgtggt ggtcttggtg tcagggtgc cggtgccgcc     2220 gctgccgccg ccgctggtgg tgctggacaa ggtggtttgg gatctcaggg agctggtcaa     2280
ggtgccggtg ctgctgccgc tgctgccgga ggtgccggtc aggtggata cggtggactt     2340 ggatctcagg gtgctggtag aggtggacaa ggtgccggag ctgccgctgc cgctgccggt     2400
ggtgctggtc aaggaggtta cggtggtctt ggatcccatc accatcacca tcactaa      2457
```

-continued

<210> SEQ ID NO 22
<211> LENGTH: 818
<212> TYPE: PRT
<213> ORGANISM: Artificial Sequence
<220> FEATURE:
<223> OTHER INFORMATION: Description of Artificial Sequence: DP-1B 8mer
      with His Tag

<400> SEQUENCE: 22

```
Met Ala Arg Ser Gln Gly Ala Gly Gln Gly Gly Tyr Gly Gly Leu Gly
  1               5                  10                  15

Ser Gln Gly Ala Gly Arg Gly Gly Leu Gly Gly Gln Gly Ala Gly Ala
             20                  25                  30

Ala Ala Ala Ala Ala Gly Gly Ala Gly Gln Gly Gly Leu Gly Ser
         35                  40                  45

Gln Gly Ala Gly Gln Gly Ala Gly Ala Ala Ala Ala Ala Gly Gly
     50                  55                  60

Ala Gly Gln Gly Gly Tyr Gly Gly Leu Gly Ser Gln Gly Ala Gly Arg
 65                  70                  75                  80

Gly Gly Gln Gly Ala Gly Ala Ala Ala Ala Ala Gly Gly Ala Gly
             85                  90                  95

Gln Gly Gly Tyr Gly Gly Leu Gly Ser Gln Gly Ala Gly Gln Gly Gly
            100                 105                 110

Tyr Gly Gly Leu Gly Ser Gln Gly Ala Gly Arg Gly Gly Leu Gly Gly
            115                 120                 125

Gln Gly Ala Gly Ala Ala Ala Ala Ala Ala Gly Gly Ala Gly Gln
        130                 135                 140

Gly Gly Leu Gly Ser Gln Gly Ala Gly Gln Gly Ala Gly Ala Ala Ala
145                 150                 155                 160

Ala Ala Ala Gly Gly Ala Gly Gln Gly Gly Tyr Gly Gly Leu Gly Ser
                165                 170                 175

Gln Gly Ala Gly Arg Gly Gly Gln Gly Ala Gly Ala Ala Ala Ala Ala
            180                 185                 190

Ala Gly Gly Ala Gly Gln Gly Gly Tyr Gly Gly Leu Gly Ser Gln Gly
        195                 200                 205

Ala Gly Gln Gly Gly Tyr Gly Gly Leu Gly Ser Gln Gly Ala Gly Arg
    210                 215                 220

Gly Gly Leu Gly Gly Gln Gly Ala Gly Ala Ala Ala Ala Ala Ala
225                 230                 235                 240

Gly Gly Ala Gly Gln Gly Gly Leu Gly Ser Gln Gly Ala Gly Gln Gly
                245                 250                 255

Ala Gly Ala Ala Ala Ala Ala Ala Gly Gly Ala Gly Gln Gly Gly Tyr
            260                 265                 270

Gly Gly Leu Gly Ser Gln Gly Ala Gly Arg Gly Gly Gln Gly Ala Gly
        275                 280                 285

Ala Ala Ala Ala Ala Gly Gly Ala Gly Gln Gly Gly Tyr Gly Gly
    290                 295                 300

Leu Gly Ser Gln Gly Ala Gly Gln Gly Gly Tyr Gly Gly Leu Gly Ser
305                 310                 315                 320

Gln Gly Ala Gly Arg Gly Gly Leu Gly Gly Gln Gly Ala Gly Ala Ala
            325                 330                 335

Ala Ala Ala Ala Gly Gly Ala Gly Gln Gly Gly Leu Gly Ser Gln
        340                 345                 350

Gly Ala Gly Gln Gly Ala Gly Ala Ala Ala Ala Ala Gly Gly Ala
    355                 360                 365
```

-continued

```
Gly Gln Gly Gly Tyr Gly Gly Leu Gly Ser Gln Gly Ala Gly Arg Gly
    370                 375                 380
Gly Gln Gly Ala Gly Ala Ala Ala Ala Ala Gly Gly Ala Gly Gln
385                 390                 395                 400
Gly Gly Tyr Gly Gly Leu Gly Ser Gln Gly Ala Gly Gln Gly Gly Tyr
                405                 410                 415
Gly Gly Leu Gly Ser Gln Gly Ala Gly Arg Gly Gly Leu Gly Gly Gln
            420                 425                 430
Gly Ala Gly Ala Ala Ala Ala Ala Ala Gly Gly Ala Gly Gln Gly
        435                 440                 445
Gly Leu Gly Ser Gln Gly Ala Gly Gln Gly Ala Gly Ala Ala Ala
    450                 455                 460
Ala Ala Gly Gly Ala Gly Gln Gly Gly Tyr Gly Gly Leu Gly Ser Gln
465                 470                 475                 480
Gly Ala Gly Arg Gly Gly Gln Gly Ala Gly Ala Ala Ala Ala Ala
                485                 490                 495
Gly Gly Ala Gly Gln Gly Gly Tyr Gly Gly Leu Gly Ser Gln Gly Ala
            500                 505                 510
Gly Gln Gly Gly Tyr Gly Gly Leu Gly Ser Gln Gly Ala Gly Arg Gly
        515                 520                 525
Gly Leu Gly Gly Gln Gly Ala Gly Ala Ala Ala Ala Ala Ala Gly
    530                 535                 540
Gly Ala Gly Gln Gly Gly Leu Gly Ser Gln Gly Ala Gly Gln Gly Ala
545                 550                 555                 560
Gly Ala Ala Ala Ala Ala Gly Gly Ala Gly Gln Gly Gly Tyr Gly
                565                 570                 575
Gly Leu Gly Ser Gln Gly Ala Gly Arg Gly Gly Gln Gly Ala Gly Ala
            580                 585                 590
Ala Ala Ala Ala Gly Gly Ala Gly Gln Gly Gly Tyr Gly Gly Leu
        595                 600                 605
Gly Ser Gln Gly Ala Gly Gln Gly Gly Tyr Gly Gly Leu Gly Ser Gln
    610                 615                 620
Gly Ala Gly Arg Gly Gly Leu Gly Gly Gln Gly Ala Gly Ala Ala Ala
625                 630                 635                 640
Ala Ala Ala Ala Gly Gly Ala Gly Gln Gly Gly Leu Gly Ser Gln Gly
                645                 650                 655
Ala Gly Gln Gly Ala Gly Ala Ala Ala Ala Ala Gly Gly Ala Gly
            660                 665                 670
Gln Gly Gly Tyr Gly Gly Leu Gly Ser Gln Gly Ala Gly Arg Gly Gly
        675                 680                 685
Gln Gly Ala Gly Ala Ala Ala Ala Ala Gly Gly Ala Gly Gln Gly
    690                 695                 700
Gly Tyr Gly Gly Leu Gly Ser Gln Gly Ala Gly Gln Gly Gly Tyr Gly
705                 710                 715                 720
Gly Leu Gly Ser Gln Gly Ala Gly Arg Gly Gly Leu Gly Gly Gln Gly
                725                 730                 735
Ala Gly Ala Ala Ala Ala Ala Ala Gly Gly Ala Gly Gln Gly Gly
            740                 745                 750
Leu Gly Ser Gln Gly Ala Gly Gln Gly Ala Gly Ala Ala Ala Ala
        755                 760                 765
Ala Gly Gly Ala Gly Gln Gly Gly Tyr Gly Gly Leu Gly Ser Gln Gly
    770                 775                 780
Ala Gly Arg Gly Gly Gln Gly Ala Gly Ala Ala Ala Ala Ala Ala Gly
```

785                 790                 795                 800
Gly Ala Gly Gln Gly Gly Tyr Gly Gly Leu Gly Ser His His His His
                        805                 810                 815
His His

<210> SEQ ID NO 23
<211> LENGTH: 4881
<212> TYPE: DNA
<213> ORGANISM: Artificial Sequence
<220> FEATURE:
<223> OTHER INFORMATION: Description of Artificial Sequence:  DP-1B 16
      mere coding region with His Tag

<400> SEQUENCE: 23

| | |
|---|---|
| atggctagat ctcaaggagc cggtcaaggt ggttacggag gtctgggatc tcaaggtgct | 60 |
| ggacgtggtg gtcttggtgg tcagggtgcc ggtgccgccg ctgccgccgc cgctggtggt | 120 |
| gctggacaag gtggtttggg atctcaggga gctggtcaag gtgccggtgc tgctgccgct | 180 |
| gctgccggag gtgccggtca gggtggatac ggtggacttg gatctcaggg tgctggtaga | 240 |
| ggtggacaag gtgccggagc tgccgctgcc gctgccggtg gtgctggtca aggaggttac | 300 |
| ggtggtcttg gatctcaagg agccggtcaa ggtggttacg gaggtctggg atctcaaggt | 360 |
| gctggacgtg gtggtcttgg tggtcagggt gccggtgccg ccgctgccgc cgctggtggt | 420 |
| ggtgctggac aaggtggttt gggatctcag ggagctggtc aaggtgccgg tgctgctgcc | 480 |
| gctgctgccg gaggtgccgg tcaggtgtgga tacggtggac ttggatctca gggtgctggt | 540 |
| agaggtggac aaggtgccgg agctgccgct gccgctgccg gtggtgctgg tcaaggaggt | 600 |
| tacggtggtc ttggatctca aggagccggt caaggtggtt acggaggtct gggatctcaa | 660 |
| ggtgctggac gtggtggtct tggtggtcag ggtgccggtg ccgccgctgc cgccgccgct | 720 |
| ggtggtgctg gacaaggtgg tttgggatct caggagctg gtcaaggtgc cggtgctgct | 780 |
| gccgctgctg ccggaggtgc cggtcagggt ggatacggtg gacttggatc tcagggtgct | 840 |
| ggtagaggtg gacaaggtgc cggagctgcc gctgccgctg ccggtggtgc tggtcaagga | 900 |
| ggttacggtg gtcttggatc tcaaggagcc ggtcaaggtg gttacggagg tctgggatct | 960 |
| caaggtgctg gacgtggtgg tcttggtggt caggtgccg gtgccgccgc tgccgccgcc | 1020 |
| gctggtggtg ctggacaagg tggtttggga tctcaggag ctggtcaagg tgccggtgct | 1080 |
| gctgccgctg ctgccggagg tgccggtcag gtggatacg gtggacttgg atctcaggt | 1140 |
| gctggtagag gtggacaagg tgccggagct gccgctgccc tgccggtgg tgctggtcaa | 1200 |
| ggaggttacg gtggtcttgg atctcaagga gccggtcaag gtggttacgg aggtctggga | 1260 |
| tctcaaggtg ctggacgtgg tggtcttggt ggtcaggtg ccggtgccgc cgctgccgcc | 1320 |
| gccgctggtg gtgctggaca aggtggtttg ggatctcagg gagctggtca aggtgccggt | 1380 |
| gctgctgccg ctgctgccgg aggtgccggt cagggtggat acgtggact tggatctcag | 1440 |
| ggtgctggta gaggtggaca aggtgccgga gctgccgctg ccgctgccgg tggtgctggt | 1500 |
| caaggaggtt acggtggtct tggatctcaa ggagccggtc aaggtggtta cggaggtctg | 1560 |
| ggatctcaag gtgctggacg tggtggtctt ggtggtcagg gtgccggtgc cgccgctgcc | 1620 |
| gccgccgctg gtggtgctgg acaaggtggt ttgggatctc agggagctgg tcaaggtgcc | 1680 |
| ggtgctgctg ccgctgctgc cggaggtgcc ggtcagggtg atacggtgg acttggatct | 1740 |
| cagggtgctg gtagaggtgg acaaggtgcc ggagctgccg ctgccgctgc cggtggtgct | 1800 |
| ggtcaaggag gttacggtgg tcttggatct caaggagccg gtcaaggtgg ttacggaggt | 1860 |

-continued

```
ctgggatctc aaggtgctgg acgtggtggt cttggtggtc agggtgccgg tgccgccgct       1920
gccgccgccg ctggtggtgc tggacaaggt ggtttgggat ctcagggagc tggtcaaggt       1980
gccggtgctg ctgccgctgc tgccggaggt gccggtcagg gtggatacgg tggacttgga       2040
tctcagggtg ctggtagagg tggacaaggt gccggagctg ccgctgccgc tgccggtggt       2100
gctggtcaag gaggttacgg tggtcttgga tctcaaggag ccggtcaagg tggttacgga       2160
ggtctgggat ctcaaggtgc tggacgtggt ggtcttggtg gtcagggtgc cggtgccgcc       2220
gctgccgccg ccgctggtgg tgctggacaa ggtggtttgg gatctcaggg agctggtcaa       2280
ggtgccggtg ctgctgccgc tgctgccgga ggtgccggtc agggtggata cggtggactt       2340
ggatctcagg gtgctggtag aggtggacaa ggtgccggag ctgccgctgc cgctgccggt       2400
ggtgctggtc aaggaggtta cggtggtctt ggatctcaag gagccggtca aggtggttac       2460
ggaggtctgg gatctcaagg tgctggacgt ggtggtcttg gtggtcaggg tgccggtgcc       2520
gccgctgccg ccgccgctgg tggtgctgga caaggtggtt tgggatctca gggagctggt       2580
caaggtgccg gtgctgctgc cgctgctgcc ggaggtgccg tcagggtgg atacggtgga        2640
cttggatctc aggtgctggg tagaggtgga caaggtgccg gagctgccgc tgccgctgcc       2700
ggtggtgctg gtcaaggagg ttacggtggt cttggatctc aaggagccgg tcaaggtggt       2760
tacggaggtc tgggatctca aggtgctgga cgtggtggtc ttggtggtca gggtgccggt       2820
gccgccgctg ccgccgccgc tggtggtgct ggacaaggtg gtttgggatc tcagggagct       2880
ggtcaaggtg ccggtgctgc tgccgctgct gccggaggtg ccggtcaggg tggatacggt       2940
ggacttggat ctcagggtgc tggtagaggt ggacaaggtg ccggagctgc cgctgccgct       3000
gccggtggtg ctggtcaagg aggttacggt ggtcttggat ctcaaggagc cggtcaaggt       3060
ggttacggag gtctgggatc tcaaggtgct ggacgtggtg gtcttggtgg tcagggtgcc       3120
ggtgccgccg ctgccgccgc cgctggtggt gctggacaag gtggtttggg atctcaggga       3180
gctggtcaag gtgccggtgc tgctgccgct gctgccggag gtgccggtca gggtggatac       3240
ggtggacttg gatctcaggg tgctggtaga ggtggacaag gtgccggagc tgccgctgcc       3300
gctgccggtg gtgctggtca aggaggttac ggtggtcttg gatctcaagg agccggtcaa       3360
ggtggttacg gaggtctggg atctcaaggt gctggacgtg gtggtcttgg tggtcagggt       3420
gccggtgccg ccgctgccgc cgccgctggt ggtgctggac aaggtggttt gggatctcag       3480
ggagctggtc aaggtgccgg tgctgctgcc gctgctgccg gaggtgccgg tcaggtgga        3540
tacggtggac ttggatctca gggtgctggt agaggtggac aaggtgccgg agctgccgct       3600
gccgctgccg gtggtgctgg tcaaggaggt tacggtggtc ttggatctca aggagccggt       3660
caaggtggtt acggaggtct gggatctcaa ggtgctggac gtggtggtct tggtggtcag       3720
ggtgccggtg ccgccgctgc cgccgccgct ggtggtgctg gacaaggtgg tttgggatct       3780
cagggagctg gtcaaggtgc cggtgctgct gccgctgctg ccgaggtgc cggtcagggt        3840
ggatacggtg gacttggatc tcagggtgct ggtagaggtg gacaaggtgc cggagctgcc       3900
gctgccgctg ccgtggtgc tggtcaagga ggttacggtg gtcttggatc tcaaggagcc        3960
ggtcaaggtg gttacggagg tctgggatct caaggtgctg gacgtggtgg tcttggtggt       4020
cagggtgccg gtgccgccgc tgccgccgcc gctggtggtg ctggacaagg tggtttggga       4080
tctcagggag ctggtcaagg tgccggtgct gctgccgctg ctgccggagg tgccggtcag       4140
ggtggatacg gtggacttgg atctcagggt gctggtagag gtggacaagg tgccggagct       4200
```

```
gccgctgccg ctgccggtgg tgctggtcaa ggaggttacg gtggtcttgg atctcaagga    4260
gccggtcaag gtggttacgg aggtctggga tctcaaggtg ctggacgtgg tggtcttggt    4320
ggtcagggtg ccggtgccgc cgctgccgcc gccgctggtg gtgctggaca aggtggtttg    4380
ggatctcagg gagctggtca aggtgccggt gctgctgccg ctgctgccgg aggtgccggt    4440
cagggtggat acggtggact tggatctcag ggtgctggta gaggtggaca aggtgccgga    4500
gctgccgctg ccgctgccgg tggtgctggt caaggaggtt acggtggtct tggatctcaa    4560
ggagccggtc aaggtggtta cggaggtctg ggatctcaag gtgctggacg tggtggtctt    4620
ggtggtcagg gtgccggtgc cgccgctgcc gccgccgctg gtggtgctgg acaaggtggt    4680
ttgggatctc agggagctgg tcaaggtgcc ggtgctgctg ccgctgctgc cggaggtgcc    4740
ggtcagggtg gatacggtgg acttggatct caggggtgctg gtagaggtgg acaaggtgcc    4800
ggagctgccg ctgccgctgc cggtggtgct ggtcaaggag gttacggtgg tcttggatcc    4860
catcaccatc accatcacta a                                              4881
```

<210> SEQ ID NO 24
<211> LENGTH: 1626
<212> TYPE: PRT
<213> ORGANISM: Artificial Sequence
<220> FEATURE:
<223> OTHER INFORMATION: Description of Artificial Sequence: DP-1B
      16mer with His Tag

<400> SEQUENCE: 24

```
Met Ala Arg Ser Gln Gly Ala Gly Gln Gly Gly Tyr Gly Gly Leu Gly
  1               5                  10                  15

Ser Gln Gly Ala Gly Arg Gly Gly Leu Gly Gly Gln Gly Ala Gly Ala
             20                  25                  30

Ala Ala Ala Ala Ala Ala Gly Gly Ala Gly Gln Gly Gly Leu Gly Ser
         35                  40                  45

Gln Gly Ala Gly Gln Gly Gly Ala Gly Ala Ala Ala Ala Ala Gly Gly
     50                  55                  60

Ala Gly Gln Gly Gly Tyr Gly Gly Leu Gly Ser Gln Gly Ala Gly Arg
 65                  70                  75                  80

Gly Gly Gln Gly Ala Gly Ala Ala Ala Ala Gly Gly Ala Gly
                 85                  90                  95

Gln Gly Gly Tyr Gly Gly Leu Gly Ser Gln Gly Ala Gly Gln Gly Gly
                100                 105                 110

Tyr Gly Gly Leu Gly Ser Gln Gly Ala Gly Arg Gly Gly Leu Gly Gly
            115                 120                 125

Gln Gly Ala Gly Ala Ala Ala Ala Ala Ala Gly Gly Ala Gly Gln
        130                 135                 140

Gly Gly Leu Gly Ser Gln Gly Ala Gly Gln Gly Ala Gly Ala Ala Ala
145                 150                 155                 160

Ala Ala Ala Gly Gly Ala Gly Gln Gly Gly Tyr Gly Gly Leu Gly Ser
                165                 170                 175

Gln Gly Ala Gly Arg Gly Gly Gln Gly Ala Gly Ala Ala Ala Ala
            180                 185                 190

Ala Gly Gly Ala Gly Gln Gly Gly Tyr Gly Gly Leu Gly Ser Gln Gly
        195                 200                 205

Ala Gly Gln Gly Gly Tyr Gly Gly Leu Gly Ser Gln Gly Ala Gly Arg
    210                 215                 220

Gly Gly Leu Gly Gly Gln Gly Ala Gly Ala Ala Ala Ala Ala Ala
225                 230                 235                 240
```

```
Gly Gly Ala Gly Gln Gly Gly Leu Gly Ser Gln Gly Ala Gly Gln Gly
            245                 250                 255

Ala Gly Ala Ala Ala Ala Ala Gly Gly Ala Gly Gln Gly Gly Tyr
        260                 265                 270

Gly Gly Leu Gly Ser Gln Gly Ala Gly Arg Gly Gly Gln Gly Ala Gly
            275                 280                 285

Ala Ala Ala Ala Ala Ala Gly Gly Ala Gly Gln Gly Gly Tyr Gly Gly
        290                 295                 300

Leu Gly Ser Gln Gly Ala Gly Gln Gly Gly Tyr Gly Gly Leu Gly Ser
305                 310                 315                 320

Gln Gly Ala Gly Arg Gly Gly Leu Gly Gly Gln Gly Ala Gly Ala Ala
                325                 330                 335

Ala Ala Ala Ala Ala Gly Gly Ala Gly Gln Gly Gly Leu Gly Ser Gln
            340                 345                 350

Gly Ala Gly Gln Gly Ala Gly Ala Ala Ala Ala Ala Gly Gly Ala
            355                 360                 365

Gly Gln Gly Gly Tyr Gly Gly Leu Gly Ser Gln Gly Ala Gly Arg Gly
        370                 375                 380

Gly Gln Gly Ala Gly Ala Ala Ala Ala Ala Gly Gly Ala Gly Gln
385                 390                 395                 400

Gly Gly Tyr Gly Gly Leu Gly Ser Gln Gly Ala Gly Gln Gly Gly Tyr
            405                 410                 415

Gly Gly Leu Gly Ser Gln Gly Ala Gly Arg Gly Gly Leu Gly Gly Gln
            420                 425                 430

Gly Ala Gly Ala Ala Ala Ala Ala Ala Gly Gly Ala Gly Gln Gly
            435                 440                 445

Gly Leu Gly Ser Gln Gly Ala Gly Gln Gly Gly Ala Gly Ala Ala Ala
        450                 455                 460

Ala Ala Gly Gly Ala Gly Gln Gly Gly Tyr Gly Gly Leu Gly Ser Gln
465                 470                 475                 480

Gly Ala Gly Arg Gly Gly Gln Gly Ala Gly Ala Ala Ala Ala Ala
            485                 490                 495

Gly Gly Ala Gly Gln Gly Gly Tyr Gly Gly Leu Gly Ser Gln Gly Ala
            500                 505                 510

Gly Gln Gly Gly Tyr Gly Gly Leu Gly Ser Gln Gly Ala Gly Arg Gly
        515                 520                 525

Gly Leu Gly Gly Gln Gly Ala Gly Ala Ala Ala Ala Ala Ala Gly
        530                 535                 540

Gly Ala Gly Gln Gly Gly Leu Gly Ser Gln Gly Ala Gly Gln Gly Ala
545                 550                 555                 560

Gly Ala Ala Ala Ala Ala Gly Gly Ala Gly Gln Gly Gly Tyr Gly
            565                 570                 575

Gly Leu Gly Ser Gln Gly Ala Gly Arg Gly Gly Gln Gly Ala Gly Ala
            580                 585                 590

Ala Ala Ala Ala Gly Gly Ala Gly Gln Gly Gly Tyr Gly Gly Leu
595                 600                 605

Gly Ser Gln Gly Ala Gly Gln Gly Gly Tyr Gly Gly Leu Gly Ser Gln
        610                 615                 620

Gly Ala Gly Arg Gly Gly Leu Gly Gly Gln Gly Ala Gly Ala Ala Ala
625                 630                 635                 640

Ala Ala Ala Ala Gly Gly Ala Gly Gln Gly Gly Leu Gly Ser Gln Gly
            645                 650                 655
```

-continued

```
Ala Gly Gln Gly Ala Gly Ala Ala Ala Ala Ala Gly Gly Ala Gly
            660                 665                 670
Gln Gly Gly Tyr Gly Gly Leu Gly Ser Gln Gly Ala Gly Arg Gly Gly
        675                 680                 685
Gln Gly Ala Gly Ala Ala Ala Ala Ala Gly Gly Ala Gly Gln Gly
        690                 695                 700
Gly Tyr Gly Gly Leu Gly Ser Gln Gly Ala Gln Gly Gly Tyr Gly
705                 710                 715                 720
Gly Leu Gly Ser Gln Gly Ala Gly Arg Gly Gly Leu Gly Gly Gln Gly
            725                 730                 735
Ala Gly Ala Ala Ala Ala Ala Gly Gly Ala Gly Gln Gly Gly
        740                 745                 750
Leu Gly Ser Gln Gly Ala Gly Gln Gly Ala Gly Ala Ala Ala Ala
        755                 760                 765
Ala Gly Gly Ala Gly Gln Gly Gly Tyr Gly Gly Leu Gly Ser Gln Gly
        770                 775                 780
Ala Gly Arg Gly Gly Gln Gly Ala Gly Ala Ala Ala Ala Ala Gly
785                 790                 795                 800
Gly Ala Gly Gln Gly Gly Tyr Gly Gly Leu Gly Ser Gln Gly Ala Gly
            805                 810                 815
Gln Gly Gly Tyr Gly Gly Leu Gly Ser Gln Gly Ala Gly Arg Gly Gly
        820                 825                 830
Leu Gly Gly Gln Gly Ala Gly Ala Ala Ala Ala Ala Gly Gly
        835                 840                 845
Ala Gly Gln Gly Gly Leu Gly Ser Gln Gly Ala Gly Gln Gly Ala Gly
        850                 855                 860
Ala Ala Ala Ala Ala Gly Gly Ala Gly Gln Gly Gly Tyr Gly Gly
865                 870                 875                 880
Leu Gly Ser Gln Gly Ala Gly Arg Gly Gly Gln Gly Ala Gly Ala Ala
            885                 890                 895
Ala Ala Ala Gly Gly Ala Gly Gln Gly Gly Tyr Gly Gly Leu Gly
        900                 905                 910
Ser Gln Gly Ala Gly Gln Gly Gly Tyr Gly Gly Leu Gly Ser Gln Gly
        915                 920                 925
Ala Gly Arg Gly Gly Leu Gly Gly Gln Gly Ala Gly Ala Ala Ala Ala
        930                 935                 940
Ala Ala Ala Gly Gly Ala Gly Gln Gly Gly Leu Gly Ser Gln Gly Ala
945                 950                 955                 960
Gly Gln Gly Ala Gly Ala Ala Ala Ala Ala Gly Gly Ala Gly Gln
            965                 970                 975
Gly Gly Tyr Gly Gly Leu Gly Ser Gln Gly Ala Gly Arg Gly Gly Gln
        980                 985                 990
Gly Ala Gly Ala Ala Ala Ala Ala Gly Gly Ala Gly Gln Gly Gly
        995                 1000                1005
Tyr Gly Gly Leu Gly Ser Gln Gly Ala Gly Gln Gly Gly Tyr Gly Gly
        1010                1015                1020
Leu Gly Ser Gln Gly Ala Gly Arg Gly Gly Leu Gly Gly Gln Gly Ala
1025                1030                1035                1040
Gly Ala Ala Ala Ala Ala Ala Gly Gly Ala Gly Gln Gly Gly Leu
            1045                1050                1055
Gly Ser Gln Gly Ala Gly Gln Gly Ala Gly Ala Ala Ala Ala Ala
        1060                1065                1070
Gly Gly Ala Gly Gln Gly Gly Tyr Gly Gly Leu Gly Ser Gln Gly Ala
```

-continued

```
            1075                1080                1085
Gly Arg Gly Gly Gln Gly Ala Gly Ala Ala Ala Ala Ala Gly Gly
            1090                1095                1100
Ala Gly Gln Gly Gly Tyr Gly Gly Leu Gly Ser Gln Gly Ala Gly Gln
1105                1110                1115                1120
Gly Gly Tyr Gly Gly Leu Gly Ser Gln Gly Ala Gly Arg Gly Gly Leu
            1125                1130                1135
Gly Gly Gln Gly Ala Gly Ala Ala Ala Ala Ala Ala Gly Gly Ala
            1140                1145                1150
Gly Gln Gly Gly Leu Gly Ser Gln Gly Ala Gly Gln Gly Ala Gly Ala
            1155                1160                1165
Ala Ala Ala Ala Gly Gly Ala Gly Gln Gly Gly Tyr Gly Gly Leu
            1170                1175                1180
Gly Ser Gln Gly Ala Gly Arg Gly Gly Gln Gly Ala Gly Ala Ala Ala
1185                1190                1195                1200
Ala Ala Ala Gly Gly Ala Gly Gln Gly Gly Tyr Gly Gly Leu Gly Ser
            1205                1210                1215
Gln Gly Ala Gly Gln Gly Gly Tyr Gly Gly Leu Gly Ser Gln Gly Ala
1220                1225                1230
Gly Arg Gly Gly Leu Gly Gly Gln Gly Ala Gly Ala Ala Ala Ala
            1235                1240                1245
Ala Ala Gly Gly Ala Gly Gln Gly Gly Leu Gly Ser Gln Gly Ala Gly
1250                1255                1260
Gln Gly Ala Gly Ala Ala Ala Ala Ala Ala Gly Gly Ala Gly Gln Gly
1265                1270                1275                1280
Gly Tyr Gly Gly Leu Gly Ser Gln Gly Ala Gly Arg Gly Gly Gln Gly
            1285                1290                1295
Ala Gly Ala Ala Ala Ala Ala Ala Gly Gly Ala Gly Gln Gly Gly Tyr
            1300                1305                1310
Gly Gly Leu Gly Ser Gln Gly Ala Gly Gln Gly Gly Tyr Gly Gly Leu
            1315                1320                1325
Gly Ser Gln Gly Ala Gly Arg Gly Gly Leu Gly Gly Gln Gly Ala Gly
            1330                1335                1340
Ala Ala Ala Ala Ala Ala Ala Gly Gly Ala Gly Gln Gly Gly Leu Gly
1345                1350                1355                1360
Ser Gln Gly Ala Gly Gln Gly Ala Gly Ala Ala Ala Ala Ala Ala Gly
            1365                1370                1375
Gly Ala Gly Gln Gly Gly Tyr Gly Gly Leu Gly Ser Gln Gly Ala Gly
            1380                1385                1390
Arg Gly Gly Gln Gly Ala Gly Ala Ala Ala Ala Ala Gly Gly Ala
            1395                1400                1405
Gly Gln Gly Gly Tyr Gly Gly Leu Gly Ser Gln Gly Ala Gly Gln Gly
            1410                1415                1420
Gly Tyr Gly Gly Leu Gly Ser Gln Gly Ala Gly Arg Gly Gly Leu Gly
1425                1430                1435                1440
Gly Gln Gly Ala Gly Ala Ala Ala Ala Ala Ala Gly Gly Ala Gly
            1445                1450                1455
Gln Gly Gly Leu Gly Ser Gln Gly Ala Gly Gln Gly Ala Gly Ala Ala
            1460                1465                1470
Ala Ala Ala Gly Gly Ala Gly Gln Gly Gly Tyr Gly Gly Leu Gly
            1475                1480                1485
Ser Gln Gly Ala Gly Arg Gly Gly Gln Gly Ala Gly Ala Ala Ala Ala
            1490                1495                1500
```

```
Ala Ala Gly Gly Ala Gly Gln Gly Gly Tyr Gly Gly Leu Gly Ser Gln
1505                1510                1515                1520

Gly Ala Gly Gln Gly Gly Tyr Gly Gly Leu Gly Ser Gln Gly Ala Gly
            1525                1530                1535

Arg Gly Gly Leu Gly Gly Gln Gly Ala Gly Ala Ala Ala Ala Ala
        1540                1545                1550

Ala Gly Gly Ala Gly Gln Gly Gly Leu Gly Ser Gln Gly Ala Gly Gln
        1555                1560                1565

Gly Ala Gly Ala Ala Ala Ala Ala Gly Gly Ala Gly Gln Gly Gly
    1570                1575                1580

Tyr Gly Gly Leu Gly Ser Gln Gly Ala Gly Arg Gly Gly Gln Gly Ala
1585                1590                1595                1600

Gly Ala Ala Ala Ala Ala Gly Gly Ala Gly Gln Gly Gly Tyr Gly
            1605                1610                1615

Gly Leu Gly Ser His His His His His His
            1620                1625

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence:DP-1B
      immunogenic region

<400> SEQUENCE: 25

Cys Gly Ala Gly Gln Gly Gly Tyr Gly Gly Leu Gly Ser Gly Gly Ala
  1               5                  10                  15

Gly Arg Gly

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 26
gctcgacgtt gtcactgaag                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 27
tcgtccagat catcctgatc                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 28
cccgtcaaac tgcatgccac                                              20

<210> SEQ ID NO 29
```

```
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
tagccatggt tagtatatct t                                              21
```